US008012168B2

(12) United States Patent
Modesitt

(10) Patent No.: US 8,012,168 B2
(45) Date of Patent: *Sep. 6, 2011

(54) ACCESS AND CLOSURE DEVICE AND METHOD

(75) Inventor: D. Bruce Modesitt, San Carlos, CA (US)

(73) Assignee: Arstasis, Inc., San Carlos, CA (US)

( * ) Notice: Subject to any disclaimer, the term of this patent is extended or adjusted under 35 U.S.C. 154(b) by 263 days.

This patent is subject to a terminal disclaimer.

(21) Appl. No.: 11/544,149

(22) Filed: Oct. 6, 2006

(65) Prior Publication Data
US 2007/0032802 A1  Feb. 8, 2007

Related U.S. Application Data

(63) Continuation of application No. 10/844,247, filed on May 12, 2004.

(51) Int. Cl.
A61B 17/08 (2006.01)

(52) U.S. Cl. .......................... 606/213; 606/215

(58) Field of Classification Search .................. 606/213, 606/215, 216, 221; 604/164.01, 44, 158, 604/115
See application file for complete search history.

(56) References Cited

U.S. PATENT DOCUMENTS

| 2,857,925 A | 6/1955 | Higginbotham |
| 3,727,614 A | 4/1973 | Kniazuk |
| 3,730,185 A | 5/1973 | Cook et al. |
| 4,006,747 A | 2/1977 | Kronenthal et al. |
| 4,744,364 A * | 5/1988 | Kensey ............ 606/213 |
| 4,774,949 A | 10/1988 | Fogarty |
| 4,850,960 A * | 7/1989 | Grayzel ............ 604/510 |
| 4,890,611 A | 1/1990 | Monfort et al. |
| 4,921,484 A | 5/1990 | Hillstead |
| 4,955,897 A | 9/1990 | Ship |
| 4,962,755 A | 10/1990 | King et al. |
| 5,183,464 A | 2/1993 | Dubrul et al. |
| 5,271,415 A | 12/1993 | Foerster et al. |
| 5,304,184 A | 4/1994 | Hathaway et al. |
| 5,336,221 A | 8/1994 | Anderson |
| 5,358,507 A | 10/1994 | Daily |
| 5,364,359 A | 11/1994 | van den Haak |
| 5,364,389 A | 11/1994 | Anderson |
| 5,368,601 A | 11/1994 | Sauer et al. |
| 5,380,290 A | 1/1995 | Makower et al. |

(Continued)

FOREIGN PATENT DOCUMENTS
EP 0637431 2/1995
(Continued)

OTHER PUBLICATIONS

International Search Report, mailed Aug. 20, 2007, for PCT Application No. PCT/US06/18915 filed on May 12, 2006, 2 pages.

(Continued)

Primary Examiner — Darwin P Erezo
Assistant Examiner — Melissa Ryckman
(74) Attorney, Agent, or Firm — Vista IP Law Group LLP

(57) ABSTRACT

Devices and methods for accessing and closing vascular sites are disclosed. Self-sealing closure devices and methods are disclosed. A device that can make a steep and controlled access path into a vascular lumen is disclosed. Methods for using the device are also disclosed.

13 Claims, 36 Drawing Sheets

U.S. PATENT DOCUMENTS

| | | | |
|---|---|---|---|
| 5,383,897 A | 1/1995 | Wholey | |
| 5,391,182 A | 2/1995 | Chin | |
| 5,391,183 A | 2/1995 | Janzen et al. | |
| 5,403,329 A | 4/1995 | Hinchcliffe | |
| 5,415,657 A | 5/1995 | Taymor-Luria | |
| 5,417,699 A | 5/1995 | Klein et al. | |
| 5,437,665 A | 8/1995 | Munro | |
| 5,439,469 A | 8/1995 | Heaven et al. | |
| 5,451,230 A | 9/1995 | Steinert | |
| 5,462,561 A | 10/1995 | Voda | |
| 5,467,786 A | 11/1995 | Allen et al. | |
| 5,470,338 A | 11/1995 | Whitfield et al. | |
| 5,474,568 A | 12/1995 | Scott | |
| 5,476,470 A | 12/1995 | Fitzgibbons, Jr. | |
| 5,489,288 A | 2/1996 | Buelna | |
| 5,496,332 A | 3/1996 | Sierra et al. | |
| 5,496,334 A | 3/1996 | Klundt et al. | |
| 5,503,634 A | 4/1996 | Christy | |
| 5,507,744 A | 4/1996 | Tay et al. | |
| 5,527,321 A | 6/1996 | Hinchliffe | |
| 5,527,322 A | 6/1996 | Klein et al. | |
| 5,536,255 A | 7/1996 | Moss | |
| 5,571,169 A | 11/1996 | Plaia et al. | |
| 5,613,974 A | 3/1997 | Andreas et al. | |
| 5,620,461 A | 4/1997 | Muijs Van De Moer et al. | |
| 5,622,188 A | 4/1997 | Plaia et al. | |
| 5,645,566 A | 7/1997 | Brenneman et al. | |
| 5,653,717 A | 8/1997 | Ko et al. | |
| 5,695,504 A | 12/1997 | Gifford, III et al. | |
| 5,700,273 A | 12/1997 | Buelna et al. | |
| 5,709,224 A | 1/1998 | Behl et al. | |
| 5,746,755 A | 5/1998 | Wood et al. | |
| 5,762,066 A | 6/1998 | Law et al. | |
| 5,766,183 A | 6/1998 | Sauer | |
| 5,772,673 A | 6/1998 | Cuny et al. | |
| 5,779,719 A | 7/1998 | Klein et al. | |
| 5,792,152 A | 8/1998 | Klein et al. | |
| 5,797,929 A | 8/1998 | Andreas et al. | |
| 5,810,810 A | 9/1998 | Tay et al. | |
| 5,817,108 A | 10/1998 | Poncet | |
| 5,830,232 A | 11/1998 | Hasson | |
| 5,836,955 A | 11/1998 | Buelna et al. | |
| 5,846,253 A | 12/1998 | Buelna et al. | |
| 5,860,990 A | 1/1999 | Nobles et al. | |
| 5,860,991 A | 1/1999 | Klein et al. | |
| 5,868,762 A | 2/1999 | Cragg et al. | |
| 5,882,302 A | 3/1999 | Driscoll, Jr. et al. | |
| 5,902,311 A | 5/1999 | Andreas et al. | |
| 5,921,994 A | 7/1999 | Andreas et al. | |
| 5,941,897 A | 8/1999 | Myers | |
| 5,954,732 A | 9/1999 | Hart et al. | |
| 5,972,005 A | 10/1999 | Stalker et al. | |
| 5,972,013 A | 10/1999 | Schmidt | |
| 5,980,539 A | 11/1999 | Kontos | |
| 5,984,917 A | 11/1999 | Fleischman et al. | |
| 5,984,948 A | 11/1999 | Hasson | |
| 5,984,950 A | 11/1999 | Cragg et al. | |
| 6,033,401 A | 3/2000 | Edwards et al. | |
| 6,036,699 A | 3/2000 | Andreas et al. | |
| 6,036,721 A | 3/2000 | Harren et al. | |
| 6,042,601 A | 3/2000 | Smith | |
| 6,063,085 A | 5/2000 | Tay et al. | |
| 6,071,292 A | 6/2000 | Makower et al. | |
| 6,071,300 A | 6/2000 | Brenneman et al. | |
| 6,077,276 A | 6/2000 | Kontos | |
| 6,080,175 A | 6/2000 | Hogendijk | |
| 6,093,173 A | 7/2000 | Balceta et al. | |
| 6,117,144 A | 9/2000 | Nobles et al. | |
| 6,117,145 A | 9/2000 | Wood et al. | |
| 6,136,010 A | 10/2000 | Modesitt et al. | |
| 6,139,560 A | 10/2000 | Kremer | |
| 6,143,004 A | 11/2000 | Davis et al. | |
| 6,146,397 A | 11/2000 | Harkrider, Jr. | |
| 6,152,918 A | 11/2000 | Padilla et al. | |
| 6,159,232 A | 12/2000 | Nowakowski | |
| 6,171,317 B1 | 1/2001 | Jackson et al. | |
| 6,179,832 B1 | 1/2001 | Jones et al. | |
| 6,190,396 B1 | 2/2001 | Whitin et al. | |
| 6,197,042 B1 | 3/2001 | Ginn et al. | |
| 6,203,554 B1 | 3/2001 | Roberts | |
| 6,206,893 B1 | 3/2001 | Klein et al. | |
| 6,206,895 B1 | 3/2001 | Levinson | |
| 6,245,079 B1 | 6/2001 | Nobles et al. | |
| 6,258,084 B1 | 7/2001 | Goldman et al. | |
| 6,302,898 B1 | 10/2001 | Edwards et al. | |
| 6,358,244 B1 | 3/2002 | Newman et al. | |
| 6,358,556 B1 | 3/2002 | Ding et al. | |
| 6,371,975 B2 | 4/2002 | Cruise et al. | |
| 6,383,208 B1 | 5/2002 | Sancoff et al. | |
| 6,395,015 B1 | 5/2002 | Borst et al. | |
| 6,398,782 B1 | 6/2002 | Pecor et al. | |
| 6,454,777 B1 | 9/2002 | Green | |
| 6,457,182 B1 | 10/2002 | Szczesuil et al. | |
| 6,458,147 B1 | 10/2002 | Cruise et al. | |
| 6,468,228 B1 | 10/2002 | Topel et al. | |
| 6,475,182 B1 | 11/2002 | Hnojewyj et al. | |
| 6,506,210 B1 | 1/2003 | Kanner | |
| 6,517,553 B2 | 2/2003 | Klein et al. | |
| 6,524,321 B2 | 2/2003 | Kanesaka | |
| 6,524,326 B1 | 2/2003 | Zhu et al. | |
| 6,533,795 B1 | 3/2003 | Tran et al. | |
| 6,562,059 B2 | 5/2003 | Edwards et al. | |
| 6,565,583 B1 | 5/2003 | Deaton et al. | |
| 6,569,012 B2 | 5/2003 | Lydon et al. | |
| 6,623,510 B2 | 9/2003 | Carley et al. | |
| 6,626,855 B1 | 9/2003 | Weng et al. | |
| 6,641,592 B1 | 11/2003 | Sauer et al. | |
| 6,656,136 B1 | 12/2003 | Weng et al. | |
| 6,663,655 B2 | 12/2003 | Ginn et al. | |
| 6,676,685 B2 | 1/2004 | Pedros et al. | |
| 6,682,489 B2 | 1/2004 | Tenerz et al. | |
| 6,689,152 B2 | 2/2004 | Balceta et al. | |
| 6,719,694 B2 | 4/2004 | Weng et al. | |
| 6,719,750 B2 | 4/2004 | Varner et al. | |
| 6,733,515 B1 * | 5/2004 | Edwards et al. | 606/214 |
| 6,743,195 B2 | 6/2004 | Zucker et al. | |
| 6,749,621 B2 | 6/2004 | Pantages et al. | |
| 6,749,622 B2 | 6/2004 | McGuckin, Jr. et al. | |
| 6,767,356 B2 | 7/2004 | Kanner et al. | |
| 6,773,699 B1 | 8/2004 | Soltz et al. | |
| 6,780,197 B2 | 8/2004 | Roe et al. | |
| 6,790,220 B2 | 9/2004 | Morris et al. | |
| 6,802,822 B1 | 10/2004 | Dodge | |
| 6,818,008 B1 | 11/2004 | Cates et al. | |
| 6,840,952 B2 | 1/2005 | Saker et al. | |
| 6,843,792 B2 | 1/2005 | Nishtala et al. | |
| 6,846,319 B2 | 1/2005 | Ginn et al. | |
| 6,846,320 B2 | 1/2005 | Ashby et al. | |
| 6,846,321 B2 | 1/2005 | Zucker | |
| 6,860,895 B1 | 3/2005 | Akerfeldt et al. | |
| 6,863,680 B2 | 3/2005 | Ashby | |
| 6,890,342 B2 | 5/2005 | Zhu et al. | |
| 6,890,343 B2 | 5/2005 | Ginn et al. | |
| 6,890,344 B2 | 5/2005 | Levinson | |
| 6,893,431 B2 | 5/2005 | Naimark et al. | |
| 6,896,692 B2 | 5/2005 | Ginn et al. | |
| 6,929,655 B2 | 8/2005 | Egnelöv et al. | |
| 6,936,053 B1 | 8/2005 | Weiss | |
| 6,939,348 B2 | 9/2005 | Malecki et al. | |
| 6,939,357 B2 | 9/2005 | Navarro et al. | |
| 6,939,363 B2 | 9/2005 | Åkerfeldt | |
| 6,939,364 B1 | 9/2005 | Soltz et al. | |
| 6,942,674 B2 | 9/2005 | Belef et al. | |
| 6,949,080 B2 | 9/2005 | Wolf et al. | |
| 6,949,107 B2 | 9/2005 | McGuckin, Jr. et al. | |
| 6,949,114 B2 | 9/2005 | Milo et al. | |
| 6,964,668 B2 | 11/2005 | Modesitt et al. | |
| 6,969,397 B2 | 11/2005 | Ginn | |
| 6,981,983 B1 | 1/2006 | Rosenblatt et al. | |
| 6,994,686 B2 | 2/2006 | Cruise et al. | |
| 7,001,400 B1 | 2/2006 | Modesitt et al. | |
| 7,008,440 B2 | 3/2006 | Sing et al. | |
| 7,008,442 B2 | 3/2006 | Brightbill | |
| 7,025,746 B2 | 4/2006 | Tal | |
| 7,025,776 B1 | 4/2006 | Houser et al. | |
| 7,029,489 B1 | 4/2006 | Ashby et al. | |
| 7,037,322 B1 | 5/2006 | Sing et al. | |

| | | |
|---|---|---|
| 7,037,323 B2 | 5/2006 | Sing et al. |
| 7,041,119 B2 | 5/2006 | Green |
| 7,074,232 B2 | 7/2006 | Kanner et al. |
| 7,077,848 B1 | 7/2006 | de Juan, Jr. et al. |
| 7,083,628 B2 | 8/2006 | Bachmen |
| 7,141,055 B2 | 11/2006 | Abrams et al. |
| 7,186,251 B2 | 3/2007 | Malecki et al. |
| 7,226,467 B2 | 6/2007 | Lucatero et al. |
| 7,235,087 B2 | 6/2007 | Modesitt et al. |
| 7,247,162 B1 | 7/2007 | Thornton |
| 7,250,028 B2 | 7/2007 | Julian et al. |
| 7,335,220 B2 | 2/2008 | Khosravi et al. |
| 7,361,180 B2 | 4/2008 | Saadat et al. |
| 7,381,201 B2 | 6/2008 | Gilbert et al. |
| 7,390,329 B2 | 6/2008 | Westra et al. |
| 7,470,237 B2 | 12/2008 | Beckman et al. |
| 7,609,673 B2 | 10/2009 | Bergenlid et al. |
| 7,621,925 B2 | 11/2009 | Saadat et al. |
| 7,635,329 B2 | 12/2009 | Goldfarb et al. |
| 7,704,264 B2 | 4/2010 | Ewers et al. |
| 2001/0031922 A1 | 10/2001 | Weng et al. |
| 2001/0047165 A1 | 11/2001 | Makower et al. |
| 2002/0016614 A1 | 2/2002 | Klein et al. |
| 2002/0062146 A1 | 5/2002 | Makower et al. |
| 2002/0156495 A1 | 10/2002 | Brenneman et al. |
| 2003/0093093 A1 | 5/2003 | Modesitt et al. |
| 2003/0100921 A1 | 5/2003 | Addis et al. |
| 2003/0158578 A1 | 8/2003 | Pantages et al. |
| 2003/0233120 A1 | 12/2003 | Akerfeldt |
| 2004/0044350 A1 | 3/2004 | Martin et al. |
| 2004/0086951 A1 | 5/2004 | Archakov et al. |
| 2004/0092964 A1 | 5/2004 | Modesitt et al. |
| 2004/0093024 A1 | 5/2004 | Lousararian et al. |
| 2004/0097978 A1 | 5/2004 | Modesitt et al. |
| 2004/0122449 A1 | 6/2004 | Modesitt et al. |
| 2004/0138522 A1 | 7/2004 | Haarstad et al. |
| 2004/0143290 A1 | 7/2004 | Brightbill |
| 2004/0153123 A1 | 8/2004 | Palermo et al. |
| 2004/0158287 A1 | 8/2004 | Cragg et al. |
| 2004/0172058 A1 | 9/2004 | Edwards et al. |
| 2004/0176758 A1 | 9/2004 | Yassinzadeh |
| 2004/0215232 A1 | 10/2004 | Belhe et al. |
| 2004/0220594 A1 | 11/2004 | de Canniere |
| 2004/0220604 A1 | 11/2004 | Fogarty et al. |
| 2004/0267307 A1 | 12/2004 | Bagaoisan et al. |
| 2004/0267308 A1 | 12/2004 | Bagaoisan et al. |
| 2005/0033361 A1 | 2/2005 | Galdonik et al. |
| 2005/0049634 A1 | 3/2005 | Chopra |
| 2005/0075653 A1 | 4/2005 | Saadat et al. |
| 2005/0085773 A1 | 4/2005 | Forsberg |
| 2005/0085851 A1 | 4/2005 | Fiehler et al. |
| 2005/0085852 A1 | 4/2005 | Ditter |
| 2005/0085854 A1 | 4/2005 | Ginn |
| 2005/0085855 A1 | 4/2005 | Forsberg |
| 2005/0085856 A1 | 4/2005 | Ginn |
| 2005/0090860 A1 | 4/2005 | Paprocki |
| 2005/0096697 A1 | 5/2005 | Forsberg et al. |
| 2005/0107826 A1 | 5/2005 | Zhu et al. |
| 2005/0125030 A1 | 6/2005 | Forsberg et al. |
| 2005/0143761 A1 | 6/2005 | Modesitt et al. |
| 2005/0149065 A1 | 7/2005 | Modesitt |
| 2005/0228443 A1 | 10/2005 | Yassinzadeh |
| 2005/0234507 A1 | 10/2005 | Geske et al. |
| 2005/0251189 A1 | 11/2005 | Saadat et al. |
| 2005/0267520 A1 | 12/2005 | Modesitt |
| 2005/0267522 A1 | 12/2005 | Yassinzadeh et al. |
| 2005/0277980 A1 | 12/2005 | Yassinzadeh |
| 2006/0009802 A1 | 1/2006 | Modesitt |
| 2006/0064159 A1 | 3/2006 | Porter et al. |
| 2006/0079914 A1 | 4/2006 | Modesitt et al. |
| 2006/0111741 A1 | 5/2006 | Nardella |
| 2006/0135990 A1 | 6/2006 | Johnson |
| 2006/0135991 A1 | 6/2006 | Kawaura et al. |
| 2006/0136035 A1 | 6/2006 | Hermann et al. |
| 2006/0142785 A1 | 6/2006 | Modesitt et al. |
| 2006/0167476 A1 | 7/2006 | Burdulis, Jr. et al. |
| 2006/0206125 A1 | 9/2006 | Fogarty et al. |
| 2006/0235449 A1 | 10/2006 | Schubart et al. |
| 2006/0259017 A1 | 11/2006 | Heil, Jr. |
| 2006/0264975 A1 | 11/2006 | Pipenhagen et al. |
| 2006/0271078 A1 | 11/2006 | Modesitt |
| 2007/0027454 A1 | 2/2007 | Modesitt |
| 2007/0027455 A1 | 2/2007 | Modesitt |
| 2007/0032802 A1 | 2/2007 | Modesitt |
| 2007/0032803 A1 | 2/2007 | Modesitt |
| 2007/0032804 A1 | 2/2007 | Modesitt |
| 2007/0106246 A1 | 5/2007 | Modesitt |
| 2007/0167959 A1 | 7/2007 | Modesitt et al. |
| 2007/0255313 A1 | 11/2007 | Modesitt |
| 2009/0105744 A1 | 4/2009 | Modesitt et al. |
| 2009/0318889 A1 | 12/2009 | Modesitt |
| 2010/0016786 A1 | 1/2010 | Drews et al. |
| 2010/0016810 A1 | 1/2010 | Drews et al. |
| 2010/0125296 A1 | 5/2010 | Modesitt |

FOREIGN PATENT DOCUMENTS

| | | |
|---|---|---|
| WO | WO-03/082363 A1 | 10/2003 |
| WO | WO-2005/112791 A2 | 12/2005 |
| WO | WO-2006/017023 A2 | 2/2006 |
| WO | WO-2006/124896 A2 | 11/2006 |
| WO | WO 2008/042034 | 4/2008 |
| WO | WO 2008/070238 | 6/2008 |
| WO | WO 2008/097955 | 8/2008 |

OTHER PUBLICATIONS

Franklin, I.J. et al. (1999). "Uptake of Tetracycline by Aortic Aneurysm Wall and Its Effect on Inflammation and Proteolysis, " *Brit. J. Surgery* 86(6):771-775.

Pyo, R. et al. (Jun. 2000). "Targeted Gene Disruption of Matrix Metalloproteinase-9 (Gelatinase B) Suppresses Development of Experimental Abdominal Aortic Aneurysms," *J. Clinical Investigation* 105(11):1641-1649.

Tambiah, J. et al. (2001). "Provocation of Experimental Aortic Inflammation and Dilatation by Inflammatory Mediators and *Chlamydia pneumoniae,*" *Brit. J. Surgery* 88(7):935-940.

Walton, L.J. et al. (Jul. 6, 1999). "Inhibition of Prostaglandin $E_2$ Synthesis in Abdominal Aortic Aneurysms," *Circulation* 100:48-54.

Xu, Q. et al. (Aug. 11, 2000). "Sp1 Increases Expression of Cyclooxygenase-2 in Hypoxic Vascular Endothelium," *J. Biological Chemistry* 275(32):24583-24589.

Non-Final Office Action mailed Oct. 29, 2008, for U.S. Appl. No. 11/788,509, filed Apr. 19, 2007, eight pages.

Non-Final Office Action mailed Nov. 12, 2008, for U.S. Appl. No. 10/844,247, filed May 12, 2004, nine pages.

Non-Final Office Action mailed Jul. 31, 2008, for U.S. Appl. No. 10/888,682, filed Jul. 10, 2004, 12 pages.

International Search Report mailed Jun. 5, 2008, for PCT Application No. PCT/US05/23107 filed Jun. 30, 2005, two pages.

International Search Report mailed Aug. 8, 2008, for PCT Application No. PCT/US05/16623 filed May 12, 2005, three pages.

Non-Final Office Action mailed Oct. 8, 2008, for U.S. Appl. No. 11/432,982, filed May 12, 2006, seven pages.

Non-Final Office Action mailed Jan. 9, 2009, for U.S. Appl. No. 11/544,317, filed Oct. 6, 2006, 11 pages.

International Preliminary Report on Patentability mailed on Mar. 5, 2009, for PCT Application No. PCT/US2005/016623, filed on May 12, 2005, five pages.

Final Office Action mailed on Jun. 11, 2009, for U.S. Appl. No. 11/432,982, filed May 12, 2006, seven pages.

Final Office Action mailed on May 6, 2009, for U.S. Appl. No. 10/888,682, filed Jul. 10, 2004, eight pages.

International Preliminary Report on Patentability issued on Mar. 3, 2009, for PCT Application No. PCT/US2005/023107, filed on Jun. 30, 2005, five pages.

International Preliminary Report on Patentability issued on Nov. 14, 2007, for PCT Application No. PCT/US2006/018915, filed on May 12, 2006, five pages.

Non-Final Office Action mailed on Feb. 18, 2009, for U.S. Appl. No. 11/545,272, filed Oct. 6, 2006, seven pages.

Non-Final Office Action mailed on Feb. 23, 2009, for U.S. Appl. No. 11/544,196, filed Oct. 6, 2006, seven pages.

Non-Final Office Action mailed on Feb. 23, 2009, for U.S. Appl. No. 11/544,365, filed Oct. 6, 2006, six pages.

Non-Final Office Action mailed on Feb. 24, 2009, for U.S. Appl. No. 11/544,177, filed Oct. 6, 2006, seven pages.
European Search Report mailed on Jun. 26, 2009, for EP Patent Application No. 08011884.7, filed on May 12, 2005, five pages.
Final Office Action mailed on Jul. 6, 2009, for U.S. Appl. No. 10/844,247, filed May 12, 2004, nine pages.
Final Office Action mailed on Aug. 21, 2009, for U.S. Appl. No. 11/788,509, filed Apr. 19, 2007, ten pages.
Final Office Action mailed on Aug. 14, 2009, for U.S. Appl. No. 11/544,317, filed Oct. 6, 2006, eight pages.
International Search Report mailed on Sep. 3, 2009, for PCT Application No. PCT/US2009/051317, filed on Jul. 21, 2009, three pages.
Invitation to Pay Additional Fees mailed on Sep. 10, 2009, for PCT Application No. PCT/US09/51320, filed on Jul. 21, 2009, two pages.
Written Opinion mailed on Aug. 20, 2007, for PCT Application No. PCT/US06/18915, filed on May 12, 2006, four pages.
Written Opinion mailed on Jun. 5, 2008, for PCT Application No. PCT/US05/23107, filed on Jun. 30, 2005, four pages.
Written Opinion mailed on Aug. 8, 2008, for PCT Application No. PCT/US05/16623, filed on May 12, 2005, three pages.
Written Opinion mailed on Sep. 3, 2009, for PCT Application No. PCT/US2009/051317, filed on Jul. 21, 2009, seven pages.
Final Office Action mailed on Nov. 18, 2009, for U.S. Appl. No. 11/544,365, filed Oct. 6, 2006, 6 pages.
Final Office Action mailed on Nov. 25, 2009, for U.S. Appl. No. 11/544,177, filed Oct. 6, 2006, 8 pages.
Final Office Action mailed on Nov. 25, 2009, for U.S. Appl. No. 11/545,272, filed Oct. 6, 2006, 6 pages.
Final Office Action mailed on Nov. 27, 2009, for U.S. Appl. No. 11/544,196, filed Oct. 6, 2006, 6 pages.
Non-Final Office Action mailed on Apr. 15, 2010, for U.S. Appl. No. 11/432,982, filed May 12, 2006, eight pages.
Notice of Allowance mailed on Nov. 3, 2009, for U.S. Appl. No. 10/888,682, filed Jul. 10, 2004, 9 pages.
Non-final office action dated May 28, 2011, for related U.S. Appl. No. 12/467,251, Inventor D. Bruce Modesitt, filed May 15, 2009, (11 pages).
Office action for related AU Patent Application No. 2006247355, dated Mar. 16, 2011, (16 pages).
File history for related U.S. Appl. No. 10/844,247, filed May 12, 2004, Inventor D. Bruce Modesitt, including (211 pages total): Amendment Response to Final Office Action mailed Jul. 6, 2009, for U.S. Appl. No. 10/844,247, submitted on Dec. 7, 2009; Examiner Interview Summary Record for U.S. Appl. No. 10/844,247, mailed Sep. 30, 2009; Final Office Action for U.S. Appl. No. 10/844,247, mailed Jul. 6, 2009; Applicants Arguments/Remarks Made in an Amendment in Response to Examiner Interview Summary Record mailed Mar. 24, 2009, for U.S. Appl. No. 10/844,247, submitted on Apr. 9, 2009; Examiner Interview Summary Record for U.S. Appl. No. 10/844,247, mailed Mar. 24, 2009; Amendment Response to Non Final Office Action mailed Nov. 12, 2008, for U.S. Appl. No. 10/844,247, submitted on Mar. 12, 2009; Non Final Office Action for U.S. Appl. No. 10/844,247, mailed Nov. 12, 2008; Response to Election/Restriction mailed Jun. 16, 2008 for U.S. Appl. No. 10/844,247, submitted on Jul. 16, 2008; Requirement for Restriction/Election for U.S. Appl. No. 10/844,247, mailed Jun. 16, 2008; Examiner Interview Summary Record for U.S. Appl. No. 10/844,247, mailed Oct. 9, 2007; Amendment Response to Final Office Action mailed Jun. 28, 2007, for U.S. Appl. No. 10/844,247, submitted on Sep. 27, 2007; Final Office Action for U.S. Appl. No. 10/844,247, mailed Jun. 28, 2007; Amendment Response to Non Final Office Action mailed Jan. 4, 2007, for U.S. Appl. No. 10/844,247, submitted on Apr. 4, 2007; Non Final Office Action for U.S. Appl. No. 10/844,247, mailed Jan. 4, 2007; Response to Election/Restriction mailed Sep. 28, 2006 for U.S. Appl. No. 10/844,247, submitted on Oct. 31, 2006; Requirement for Restriction/Election for U.S. Appl. No. 10/844,247, mailed Sep. 28, 2006; Application for U.S. Appl. No. 10/844,247, filed May 12, 2004.
File history for related U.S. Appl. No. 11/544,196, filed Oct. 6, 2006, Inventor D. Bruce Modesitt, including (126 pages total): Terminal Disclaimer for U.S. Appl. No. 11/544,196, submitted Mar. 18, 2011; Amendment Response to Non Final Office Action mailed Jun. 23, 2010, for U.S. Appl. No. 11/544,196, submitted on Dec. 23, 2010; Examiner Interview Summary Record for U.S. Appl. No. 11/544,196, mailed Dec. 16, 2010; Non Final Office Action for U.S. Appl. No. 11/544,196, mailed Jun. 23, 2010; Amendment Response to Final Office Action mailed Nov. 27, 2009, for U.S. Appl. No. 11/544,196, submitted on May 7, 2010; Examiner Interview Summary Record for U.S. Appl. No. 11/544,196, mailed Feb. 16, 2010; Final Office Action for U.S. Appl. No. 11/544,196, mailed Nov. 27, 2009; Examiner Interview Summary Record for U.S. Appl. No. 11/544,196, mailed Aug. 6, 2009; Supplemental Amendment Response to Non Final Office Action mailed Sep. 2, 2003, for U.S. Appl. No. 11/544,196, submitted on Aug. 3, 2009; Amendment Response to Non Final Office Action mailed Sep. 2, 2003, for U.S. Appl. No. 11/544,196, submitted on Jun. 23, 2009; Non Final Office Action for U.S. Appl. No. 11/544,196, mailed Feb. 23, 2009; Preliminary Amendment for U.S. Appl. No. 11/544,196, submitted Oct. 6, 2006; Application for U.S. Appl. No. 11/544,196, filed Oct. 6, 2006.
File history for related U.S. Appl. No. 11/545,272, filed Oct. 6, 2006, Inventor D. Bruce Modesitt, including (154 pages total): Terminal Disclaimer for U.S. Appl. No. 11/545,272, submitted Dec. 23, 2010; Amendment Response to Non Final Office Action mailed Jun. 23, 2010, for U.S. Appl. No. 11/545,272, submitted on Dec. 23, 2010; Examiner Interview Summary Record for U.S. Appl. No. 11/545,272, mailed Dec. 16, 2010; Non Final Office Action for U.S. Appl. No. 11/545,272, mailed Jun. 23, 2010; Amendment Response to Final Office Action mailed Nov. 25, 2009, for U.S. Appl. No. 11/545,272, submitted on May 7, 2010; Examiner Interview Summary Record for U.S. Appl. No. 11/545,272, mailed Feb. 16, 2010; Final Office Action for U.S. Appl. No. 11/545,272, mailed Nov. 25, 2009; Examiner Interview Summary Record for U.S. Appl. No. 11/545,272, mailed Aug. 3, 2009; Supplemental Amendment Response to Non Final Office Action mailed Feb. 18, 2009, for U.S. Appl. No. 11/545,272, submitted on Aug. 3, 2009; Amendment Response to Non Final Office Action mailed Feb. 18, 2009, for U.S. Appl. No. 11/545,272, submitted on Jun. 18, 2009; Non Final Office Action for U.S. Appl. No. 11/545,272, mailed Feb. 18, 2009; Preliminary Amendment for U.S. Appl. No. 11/545,272, submitted Oct. 6, 2006; Application for U.S. Appl. No. 11/545,272, filed Oct. 6, 2006.
File history for related U.S. Appl. No. 11/544,365, filed Oct. 6, 2006, Inventor D. Bruce Modesitt, including (152 pages total): Terminal Disclaimer for U.S. Appl. No. 11/544,365, submitted Dec. 23, 2010; Amendment Response to Non Final Office Action mailed Jun. 25, 2010, for U.S. Appl. No. 11/544,365, submitted on Dec. 23, 2010; Examiner Interview Summary Record for U.S. Appl. No. 11/544,365, mailed Dec. 16, 2010; Non Final Office Action for U.S. Appl. No. 11/544,365, mailed Jun. 25, 2010; Amendment Response to Final Office Action mailed Nov. 18, 2009, for U.S. Appl. No. 11/544,365, submitted on May 7, 2010; Examiner Interview Summary Record for U.S. Appl. No. 11/544,365, mailed Feb. 16, 2010; Final Office Action for U.S. Appl. No. 11/544,365, mailed Nov. 18, 2009; Examiner Interview Summary Record for U.S. Appl. No. 11/544,365, mailed Aug. 6, 2009; Supplemental Amendment Response to Non Final Office Action mailed Feb. 23, 2009, for U.S. Appl. No. 11/544,365, submitted on Aug. 6, 2009; Amendment Response to Non Final Office Action mailed Feb. 23, 2009, for U.S. Appl. No. 11/544,365, submitted on Jun. 22, 2009; Non Final Office Action for U.S. Appl. No. 11/544,365, mailed Feb. 23, 2009; Preliminary Amendment for U.S. Appl. No. 11/544,365, submitted Oct. 6, 2006; Application for U.S. Appl. No. 11/544,365, filed Oct. 6, 2006.
File history for related U.S. Appl. No. 11/544,177, filed Oct. 6, 2006, Inventor D. Bruce Modesitt, including (167 pages total): Terminal Disclaimer for U.S. Appl. No. 11/544,177, submitted Mar. 18, 2011; Amendment Response to Non Final Office Action mailed Jun. 22, 2010, for U.S. Appl. No. 11/544,177, submitted on Dec. 22, 2010; Terminal Disclaimer for U.S. Appl. No. 11/544,177, submitted Dec. 22, 2011; Non Final Office Action for U.S. Appl. No. 11/544,177, mailed Jun. 22, 2010; Amendment Response to Final Office Action mailed Nov. 25, 2009, for U.S. Appl. No. 11/544,177, submitted on May 7, 2010; Examiner Interview Summary Record for U.S. Appl. No. 11/544,177, mailed Feb. 16, 2010; Final Office Action for U.S. Appl. No. 11/544,177, mailed Nov. 25, 2009; Examiner Interview Summary Record for U.S. Appl. No. 11/544,177, mailed Aug. 6, 2009; Supplemental Amendment Response to Non Final Office Action mailed Feb. 24, 2009, for U.S. Appl. No. 11/544,177, submitted on Aug. 6, 2009; Amendment Response to Non Final Office Action mailed Feb. 24, 2009, for U.S. Appl. No. 11/544,177, submitted on Jun. 24, 2009; Non Final Office Action for U.S. Appl. No. 11/544,177, mailed Feb. 24, 2009; Preliminary Amendment for U.S. Appl. No. 11/544,177, submitted Oct. 6, 2006; Application for U.S. Appl. No. 11/544,177, filed Oct. 6, 2006.

File history for related U.S. Appl. No. 10/888,682, filed Jul. 10, 2004, Inventor D. Bruce Modesitt, including (141 pages total): Supplemental Amendment Response to Final Office Action mailed May 6, 2009 for U.S. Appl. No. 10/888,682, submitted on Aug. 28, 2009 Amendment Response to Final Office Action dated May 6, 2009 for U.S. Appl. No. 10/888,682, submitted on Jul. 1, 2009 Final Office Action for U.S. Appl. No. 10/888,682, mailed May 6, 2009 Amendment Response to Non Final Office Action mailed Jul. 31, 2008 for U.S. Appl. No. 10/888,682, submitted on Nov. 26, 2008 Non Final Office Action for U.S. Appl. No. 10/888,682, mailed Jul. 31, 2008 Response to Restriction and Election mailed Feb. 15, 2008 for U.S. Appl. No. 10/888,682, submitted on Apr. 30, 2008 Requirement for Restriction and Election for U.S. Appl. No. 10/888,682, mailed on Feb. 15, 2008 Application for U.S. Appl. No. 10/888,682, filed Jul. 10, 2004.

File history for related U.S. Appl. No. 12/693,395, filed Jan. 25, 2010, Inventor D. Bruce Modesitt, including (61 pages): Amendment Response to Application filed Jan. 25, 2010 for U.S. Appl. No. 12/693,395, submitted on Jan. 25, 2010 Application for U.S. Appl. No. 12/693,395, filed Jan. 25, 2010.

File history for related application U.S. Appl. No. 11/432,982, filed May 12, 2006, Inventor D. Bruce Modesitt, including (128 pages): Examiner Interview Summary Record for U.S. Appl. No. 11/432,982, dated Mar. 14, 2011 Notice Regarding Non-Responsive Amendment for U.S. Appl. No. 11/432,982, dated Jan. 5, 2011 Amendment Response to Non Final Office Action mailed Apr. 15, 2010 for U.S. Appl. No. 11/432,982, submitted on Oct. 15, 2010 Non Final Office Action for U.S. Appl. No. 11/432,982, mailed Apr. 15, 2010 Amendment Response to Final Office Action mailed Jun. 11, 2009 for U.S. Appl. No. 11/432,982, submitted on Aug. 27, 2009 Final Office Action for U.S. Appl. No. 11/432,982, mailed Jun. 11, 2009 Amendment Response to Non Final Office Action mailed Oct. 8, 2008 for U.S. Appl. No. 11/432,982, submitted on Jan. 6, 2009 Non Final Office Action for U.S. Appl. No. 11/432,982, mailed Oct. 8, 2008 Application for U.S. Appl. No. 11/432,982, filed May 12, 2006.

File history for related U.S. Appl. No. 11/544,317, filed Oct. 6, 2006, Inventor D. Bruce Modesitt, including (163 pages): Terminal Disclaimer Decision for U.S. Appl. No. 11/544,317, mailed on Mar. 15, 2011 Amendment Response to Non Final Office Action mailed Jun. 24, 2010 for U.S. Appl. No. 11/544,317, submitted on Dec. 23, 2010 Terminal Disclaimer for U.S. Appl. No. 11/544,317, filed Dec. 23, 2010 Non Final Office Action for U.S. Appl. No. 11/544,317, mailed Jun. 24, 2010 Amendment Response to Final Office Action mailed on Aug. 14, 2009 for U.S. Appl. No. 11/544,317, submitted on Feb. 12, 2010 Final Office Action for U.S. Appl. No. 11/544,317, mailed Aug. 14, 2009 Amendment Response to Non Final Office Action mailed Jan. 9, 2009 for U.S. Appl. No. 11/544,317, submitted on May 11, 2009 Non Final Office Action for U.S. Appl. No. 11/544,317, mailed Jan. 9, 2009 Amendment Response to Application filed on Oct. 6, 2006 for U.S. Appl. No. 11/544,317, submitted on Oct. 6, 2006 Application for U.S. Appl. No. 11/544,317, filed Oct. 6, 2006.

File history for related U.S. Appl. No. 11/788,509, filed Apr. 19, 2007, Inventor D. Bruce Modesitt, including (288 pages): Terminal Disclaimer Decision for U.S. Appl. No. 11/788,509, mailed on Mar. 21, 2011 Terminal Disclaimer for U.S. Appl. No. 11/788,509, filed Mar. 18, 2011 Terminal Disclaimer Decision for U.S. Appl. No. 11/788,509, mailed on Mar. 11, 2011 Amendment Response to Non Final Office Action mailed Jun. 24, 2010 for U.S. Appl. No. 11/788,509, submitted on Dec. 23, 2010 Terminal Disclaimer for U.S. Appl. No. 11/788,509, filed Dec. 23, 2010 Non Final Office Action for U.S. Appl. No. 11/788,509, mailed Jun. 24, 2010 Supplemental Amendment Response to Final Office Action mailed Aug. 21, 2009 for U.S. Appl. No. 11/788,509, submitted on Apr. 29, 2010 Amendment Response to Final Office Action mailed Aug. 21, 2009 for U.S. Appl. No. 11/788,509, submitted on Feb. 19, 2010 Final Office Action for U.S. Appl. No. 11/788,509, mailed Aug. 21, 2009 Amendment Response to Notice Regarding Non-Responsive Amendment dated Apr. 15, 2009 for U.S. Appl. No. 11/788,509, submitted on May 14, 2009 Notice Regarding Non-Responsive Amendment for U.S. Appl. No. 11/788,509, dated Apr. 15, 2009 Amendment Response to Non Final Office Action mailed Oct. 29, 2008 for U.S. Appl. No. 11/788,509, submitted on Jan. 6, 2009 Non Final Office Action for U.S. Appl. No. 11/788,509, mailed Oct. 29, 2008 Response to PTO Notice to Applicant mailed May 15, 2007 for U.S. Appl. No. 11/788,509, submitted on Jul. 16, 2007 PTO Notice to Applicant for U.S. Appl. No. 11/788,509, mailed May 15, 2007 Amendment Response to Application as filed on Apr. 19, 2007 for U.S. Appl. No. 11/788,509, submitted on Apr. 19, 2007 Application for U.S. Appl. No. 11/788,509, filed Apr. 19, 2007.

File history for related U.S. Appl. No. 12/467,251, filed May 15, 2009, Inventor D. Bruce Modesitt, including (46 pages): Amendment Response to Application as filed on May 15, 2009 for U.S. Appl. No. 12/467,251, submitted on May 15, 2009 Application for U.S. Appl. No. 12/467,251, filed May 15, 2009.

File history for related U.S. Appl. No. 11/873,957, filed Oct. 17, 2007, Inventor D. Bruce Modesitt, et al., including (90 pages): Amendment Response to Notice Regarding Non-Responsive Amendment dated Feb. 7, 2011 for U.S. Appl. No. 11/873,957, submitted on Mar. 2, 2011 Examiner Interview Summary Record for U.S. Appl. No. 11/873,957, dated Feb. 7, 2011 Notice Regarding Non-Responsive Amendment for U.S. Appl. No. 11/873,957, dated Feb. 7, 2011 Amendment Response to Non Final Office Action mailed Aug. 2, 2010 for U.S. Appl. No. 11/873,957, submitted on Feb. 2, 2011 Terminal Disclaimer for U.S. Appl. No. 11/873,957, filed Feb. 2, 2011 Non Final Office Action for U.S. Appl. No. 11/873,957, mailed Aug. 2, 2010 Application for U.S. Appl. No. 11/873,957, filed Oct. 17, 2007.

File history for related U.S. Appl. No. 12/507,038, filed Jul. 21, 2009, Inventor Michael Drews, et al., including (90 pages): Application for U.S. Appl. No. 12/507,038, filed Jul. 21, 2009.

File history for related U.S. Appl. No. 12/507,043, filed Jul. 21, 2009, Inventor Michael Drews, et al., including (97 pages): Application for U.S. Appl. No. 12/507,043, filed Jul. 21, 2009.

File history for related U.S. Appl. No. 12/780,768, filed May 14, 2010, Inventor Michael Drews, et al., including (97 pages): Application for U.S. Appl. No. 12/780,768, filed May 14, 2010.

File History for related U.S. Appl. No. 12/888,209, filed Sep. 22, 2010, Inventor D. Bruce Modesitt, et al., including ( pages): Application for U.S. Appl. No. 12/888,309, filed Sep. 22, 2010.

File history for related U.S. Appl. No. 13/004,848, filed Jan. 11, 2011, Inventor D. Bruce Modesitt, et al., including (91 pages): Application for U.S. Appl. No. 13/004,848, filed Jan. 11, 2011.

Office Action dated Apr. 13, 2010, for Australian Patent Application No. 2005244834, with a filing date of May 12, 2005. (3 pages).

Office Action dated Jun. 3, 2010, for Chinese Patent Application No. 200580023327.X, with a filing date of May 12, 2005, with English translation provided by Chinese associate. (7 pages).

Further Office Action dated Sep. 6, 2010, for Israeli Patent Application No. 179173, with a filing date of Jun. 30, 2005, with English translation provided by Israeli associate. (9 pages).

Response to Office Action submitted Jul. 13, 2010, for Israeli Patent Application No. 179173, with a filing date of Jun. 30, 2005. (1 page).

Initial Office Action dated Jan. 25, 2010, for Israeli Patent Application No. 179173, with a filing date of Jun. 30, 2005, with English translation provided by Israeli associate. (5 pages).

Office Action dated Jun. 4, 2010, for Australian Patent Application No. 2005272102, with a filing date of Jun. 30, 2005. (3 pages).

Office Action dated Jun. 4, 2010, for Chinese Patent Application No. 2005800293656, with a filing date of Jun. 30, 2005, with English translation provided by Chinese associate. (10 pages).

European Search Report from European Patent Office for EP application No. EP05787529.6, Applicant Arstasis, Inc., EPO Forms 1507, 1503, and P0459, dated Nov. 5, 2010. (5 pages).

Further Office Action dated May 24, 2010, for Israeli Patent Application No. 180497, with a filing date of May 12, 2005, with English translation provided by Israeli associate. (5 pages).

Response to Office Action submitted May 23, 2010, for Israeli Patent Application No. 180497, with a filing date of May 12, 2005, with English translation provided by Israeli associate. (7 pages).

Initial Office Action dated Jan. 24, 2010, for Israeli Patent Application No. 180497, with a filing date of May 12, 2005, with English translation provided by Israeli associate. (5 pages).

PCT International Search Report and Written Opinion for PCT/US2006/018915, Applicant Arstasis, Inc., Forms PCT/ISA/210 and 237 dated Aug. 20, 2007. (6 pages).

Office Action dated May 22, 2009, for Chinese Patent Application No. 2006800252468, with a filing date of May 12, 2006, with English translation provided by Chinese associate. (7 pages).

PCT International Preliminary Report on Patentability for PCT/US2009/051320, Applicant Arstasis, Inc., Forms PCT/IB/373 and PCT/ISA/237 dated Jan. 25, 2011. (7 pages).

PCT International Search Report and Written Opinion for PCT/US2009/051320, Applicant Arstasis, Inc., Forms PCT/ISA/210, 220, and 237 dated Nov. 6, 2009. (11 pages).

PCT International Search Report and Written Opinion for PCT/US2010/035001, Applicant Arstasis, Inc., Forms PCT/ISA/210, 220, and 237 dated Jul. 19, 2010. (11 pages).

PCT International Search Report and Written Opinion for PCT/US2010/049859, Applicant Arstasis, Inc., Forms PCT/ISA/210, 220, and 237 dated Nov. 5, 2010. (14 pages).

Office Action dated Jan. 24, 2011, for Japanese Patent Application No. 2007-513356, with a filing date of May 12, 2005, and with English translation provided by Japanese associate, (7 pages).

Office Action dated Jan. 24, 2011, for Japanese Patent Application No. 2008-123950, with a filing date of May 12, 2005, and with English translation provided by Japanese associate, (4 pages).

Response to Office Action submitted Oct. 18, 2010, for Chinese Patent Application No. 2005800293656, with English instructions to respond provided to Chinese associate, (27 pages).

Office Action dated Feb. 14, 2011, for European Patent Application No. 05787529.6, with a filing date of Jun. 30, 2005, (15 pages).

Office Action dated Dec. 8, 2010, for Japanese Patent Application No. 2007-0520363, with a filing date of Jun. 30, 2005, and with English translation provided by Japanese associate, (5 pages).

Response to Office Action submitted Nov. 6, 2010, for Chinese Patent Application No. 2006800252468, with English instructions to respond provided to Chinese associate. (29 pages).

* cited by examiner

ACCESS AND CLOSURE DEVICE AND METHOD

CROSS-REFERENCE TO RELATED APPLICATION

This application is a continuation of U.S. Ser. No. 10/844,247, filed May 12, 2004, which is hereby incorporated by reference in its entirety.

BACKGROUND OF THE INVENTION

1. Field of the Invention

The present invention relates to the field of accessing a biological lumen and closing the access port thereby created.

2. Description of the Related Art

A number of diagnostic and interventional vascular procedures are now performed translumenally, where a catheter is introduced to the vascular system at a convenient access location—such as the femoral, brachial, or subclavian arteries—and guided through the vascular system to a target location to perform therapy or diagnosis. When vascular access is no longer required, the catheter and other vascular access devices must be removed from the vascular entrance and bleeding at the puncture site must be stopped.

One common approach for providing hemostasis is to apply external force near and upstream from the puncture site, typically by manual compression. This method is time-consuming, frequently requiring one-half hour or more of compression before hemostasis. This procedure is uncomfortable for the patient and frequently requires administering analgesics. Excessive pressure can also present the risk of total occlusion of the blood vessel, resulting in ischemia and/or thrombosis.

After hemostasis is achieved by manual compression, the patient is required to remain recumbent for six to eighteen hours under observation to assure continued hemostasis. During this time bleeding from the vascular access wound can restart, potentially resulting in major complications. These complications may require blood transfusion and/or surgical intervention.

Bioabsorbable fasteners have also been used to stop bleeding. Generally, these approaches rely on the placement of a thrombogenic and bioabsorbable material, such as collagen, at the superficial arterial wall over the puncture site. This method generally presents difficulty locating the interface of the overlying tissue and the adventitial surface of the blood vessel. Implanting the fastener too far from the desired location can result in failure to provide hemostasis. If, however, the fastener intrudes into the vascular lumen, thrombus can form on the fastener. Thrombus can embolize downstream and/or block normal blood flow at the thrombus site. Implanted fasteners can also cause infection and auto-immune reactions/rejections of the implant.

Suturing methods are also used to provide hemostasis after vascular access. The suture-applying device is introduced through the tissue tract with a distal end of the device located at the vascular puncture. Needles in the device draw suture through the blood vessel wall on opposite sides of the punctures, and the suture is secured directly over the adventitial surface of the blood vessel wall to close the vascular access wound.

To be successful, suturing methods need to be performed with a precise control. The needles need to be properly directed through the blood vessel wall so that the suture is well anchored in tissue to provide for tight closure. Suturing methods also require additional steps for the surgeon.

Due to the deficiencies of the above methods and devices, a need exists for a more reliable vascular closure method and device. There also exists a need for a vascular closure device and method that does not implant a foreign substance and is self-sealing. There also exists a need for a vascular closure device and method requiring no or few extra steps to close the vascular site.

BRIEF SUMMARY OF THE INVENTION

A device for accessing a biological lumen is disclosed. The biological lumen has a lumen wall having a longitudinal lumen wall axis. The device has an elongated member that has a longitudinal member axis. The member is configured to access the lumen at a first angle. The first angle is defined by the longitudinal lumen wall axis and the longitudinal member axis. The first angle is less than about 19 degrees.

The first angle can be less than about 15 degrees. The first angle can be less than about 10 degrees. The device can also have an anchor. The anchor can be configured to hold the elongated member at a fixed angle with respect to the longitudinal lumen wall axis.

The device can also have a retainer. The retainer can be configured to hold the elongated member at a fixed angle with respect to the longitudinal lumen axis.

Another device for accessing a biological lumen is disclosed. The biological lumen has a lumen wall and a longitudinal lumen wall axis. The device has a first elongated member and a second elongated member. The first elongated member has a first elongated member axis. The second elongated member has a second elongated member axis. The second elongated member is configured so that the second elongated member axis is parallel to the longitudinal lumen wall axis.

The second elongated member can have a retainer. The retainer can have an inflatable member. The retainer can have a resilient member. The second elongated member can extend substantially adjacent to the lumen wall.

Also disclosed is a device for closing an opening on a biological lumen wall. The device has a longitudinal axis, a first force-applying member, a second force-applying member, and a resilient member. The resilient member provides to the first and the second force-applying members a force that is radially outward with respect to the longitudinal axis.

A method of accessing a blood vessel through a blood vessel wall is also disclosed. The blood vessel wall has a longitudinal wall axis. The method includes entering the vessel at an angle of less than about 19 degrees with respect to the longitudinal wall axis. The method also includes inserting a lumenal tool into the vessel.

Also disclosed is a method for accessing a biological lumen. The biological lumen has a lumen wall and a longitudinal lumen wall axis. The method includes inserting in the biological lumen a second elongated member. The second elongated member has a second elongated member axis. The method also includes aligning the second elongated member so that the second elongated member axis is substantially parallel to the longitudinal lumen wall axis. Further, the method includes inserting in the biological lumen a first elongated member comprising a first elongated member axis.

Additionally disclosed is a method of closing a vascular opening. The vascular opening has an inside surface and a longitudinal axis. The method includes inserting a device in the opening and applying a force to the inside surface. The force is directed in at least one radially outward direction from the longitudinal axis.

The method can include maintaining the force. The applying a force can include the device applying at least a part of the force. The applying of a force can include the device applying all of the force.

Also disclosed is a method for accessing and closing a blood vessel having a vessel wall. The vessel wall can have an inside surface and an outside surface. The method includes forming an arteriotomy and deploying a closure augmentation device in the arteriotomy. The closure augmentation device produces pressure on the inside surface and the outside surface.

DETAILED DESCRIPTION

Figure 1:
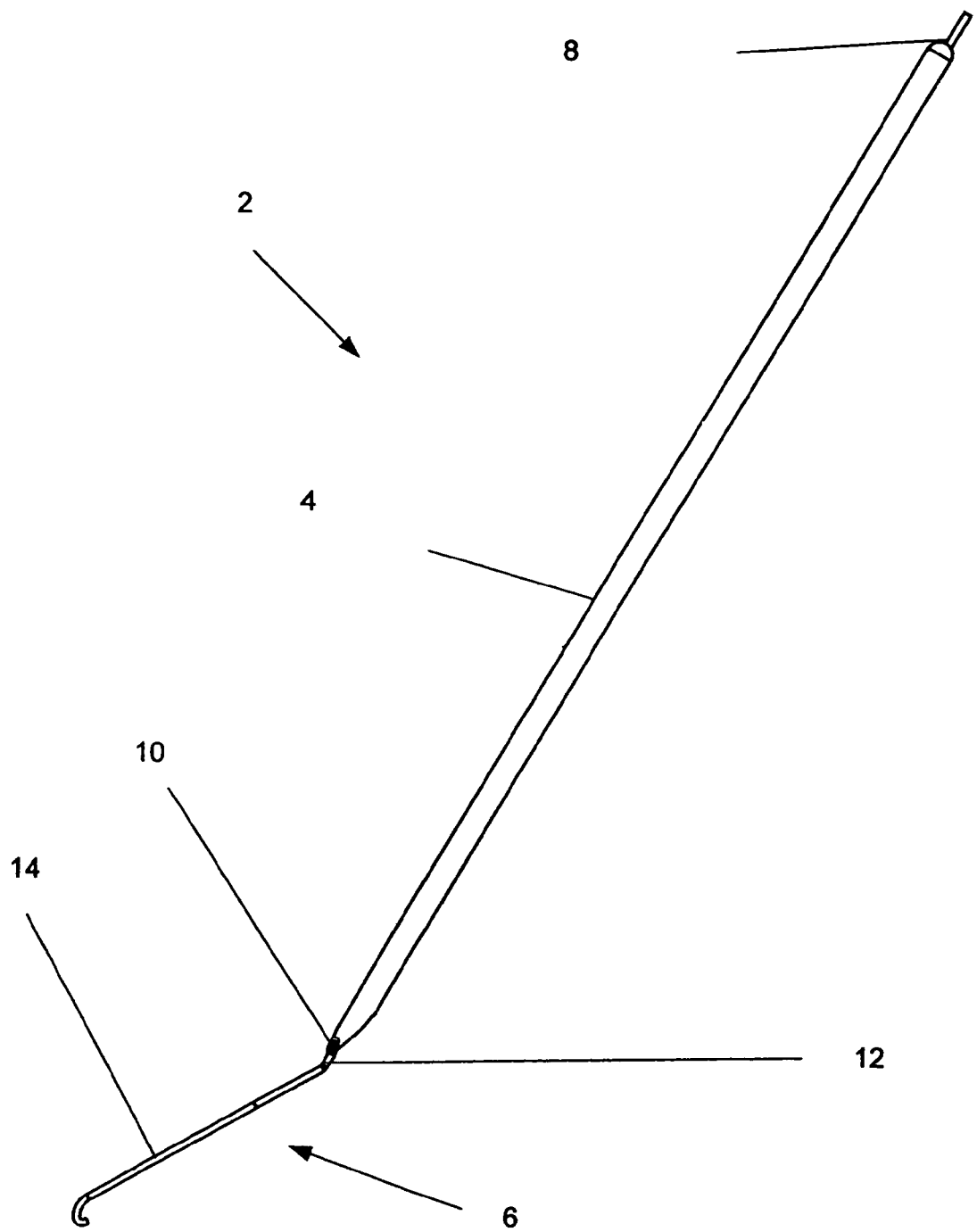
FIG. 1 is a front perspective view of an embodiment of the arteriotomy device.
Figure 2:
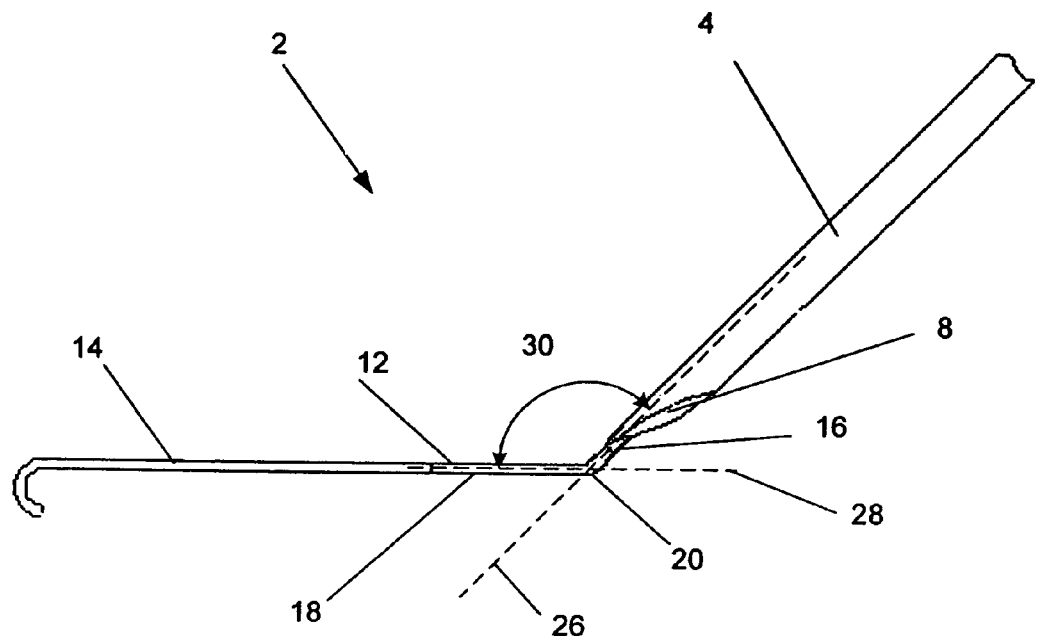
FIG. 2 is a side view of the arteriotomy device of FIG. 1.
Figure 3:
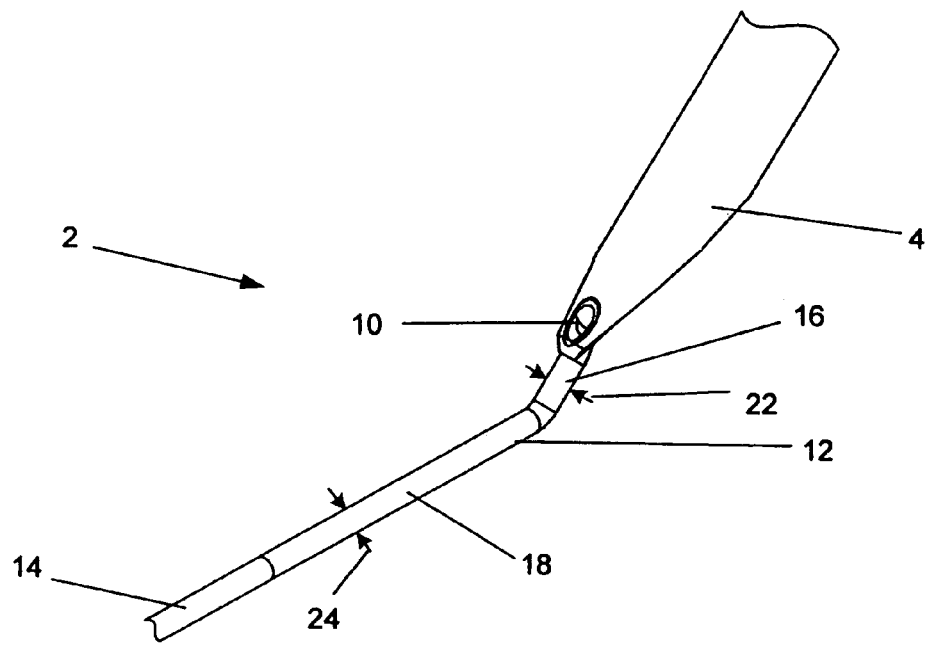
FIG. 3 is a close-up view of the arteriotomy device of FIG. 1.

FIGS. 1 through 3 illustrate a device for accessing a biological lumen, such as an arteriotomy device 2. The arteriotomy device 2 can have a delivery guide 4. The delivery guide 4 can be slidably attached to an anchor 6. The anchor 6 can be rigid, flexible or combinations thereof. The anchor 6 can be resilient, deformable or combinations thereof. The anchor 6 can be retractable and extendable from the delivery guide 4. The delivery guide 4 can have an introducer lumen 8. The introducer lumen 8 can have an introducer lumen exit port 10. The introducer lumen exit port 10 can be on the surface of the delivery guide 4.

The anchor 6 can have an anchor angle section 12. The anchor 6 can have an anchor extension section 14, for example a guide eye sheath or an attachable guidewire. The anchor extension section 14 can extend from the anchor angle section 12. The anchor extension section 14 can be separate from and attached to, or integral with, the anchor angle section 12.

The anchor angle section 12 can have an anchor angle first sub-section 16, an anchor bend 20 and an anchor angle second sub-section 18. The anchor angle first and/or second sub-sections 16 and/or 18 can be part of the anchor bend 20. The anchor bend 20 can have a sharp or gradual curve. The radius of curvature for the anchor bend 20 can be from about 0.1 mm (0.004 in.) to about 2.0 mm (0.079 in.).

The anchor angle first sub-section 16 can have an anchor angle first sub-section diameter 22 from about 0.38 mm (0.015 in.) to about 1.0 mm (0.039 in.), for example about 0.71 mm (0.028 in.). The anchor angle second sub-section 18 can have an anchor angle second sub-section diameter 24 from about 0.38 mm (0.015 in.) to about 1.0 mm (0.039 in.), for example about 0.71 mm (0.028 in.).

The anchor angle first sub-section 16 can have a delivery longitudinal axis 26. The anchor angle second sub-section 18 can have an anchor longitudinal axis 28. The intersection of the delivery longitudinal axis 26 and the anchor longitudinal axis 28 can be an anchoring angle 30. The anchoring angle 30 can be from about 20° to about 90°, more narrowly from about 30° to about 60°, for example about 45°.

Any or all elements of the arteriotomy device 2 or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polydioxanone, and pseudo-polyamino tyrosine-based acids, extruded collagen, silicone, zinc, echogenic, radioactive, radiopaque materials or combinations thereof. Examples of radiopaque materials are barium sulfate, zinc oxide, titanium, stainless steel, nickel-titanium alloys, tantalum and gold.

Any or all elements of the arteriotomy device 2, including supplemental closure devices, such as tensioners, clips, toggles, sutures, or other devices or apparatuses described herein can be or have a matrix for cell ingrowth or used with a fabric, for example a covering (not shown) that acts as a matrix for cell ingrowth. The matrix and/or fabric can be, for example, polyester (e.g., DACRON® from E. I. du Pont de Nemours and Company, Wilmington, Del.), polypropylene, PTFE, ePTFE, nylon, extruded collagen, silicone or combinations thereof.

The elements of the arteriotomy device 2 and/or the fabric can be filled and/or coated with an agent delivery matrix known to one having ordinary skill in the art and/or a therapeutic and/or diagnostic agent. The agents within these matrices can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., YIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation, Jul.* 6, 1999, 48-54; Tambiah et al, Provocation of Experimental Aortic Inflammation Mediators and *Chlamydia Pneumoniae, Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Figure 4:
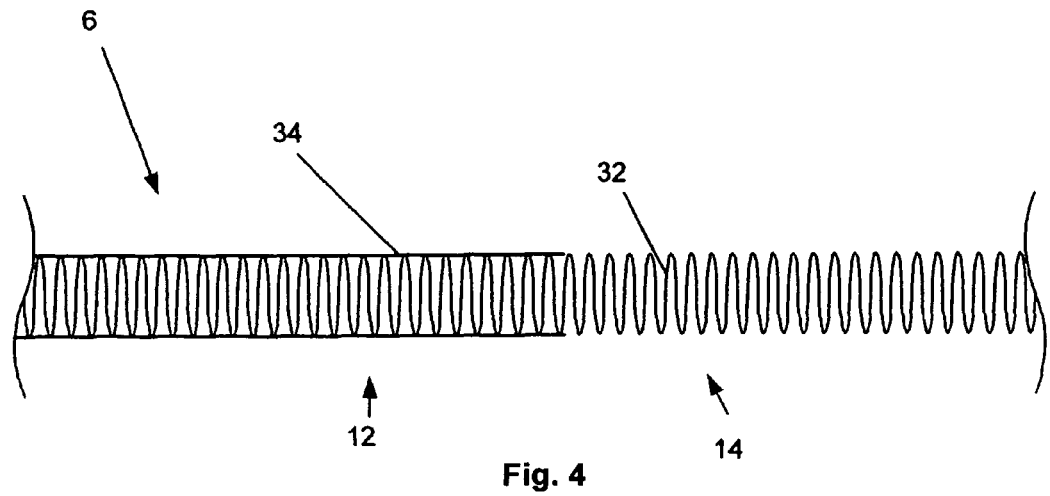
FIGS. 4 and 5 are close-up views of various embodiments of the anchor.
Figure 5:
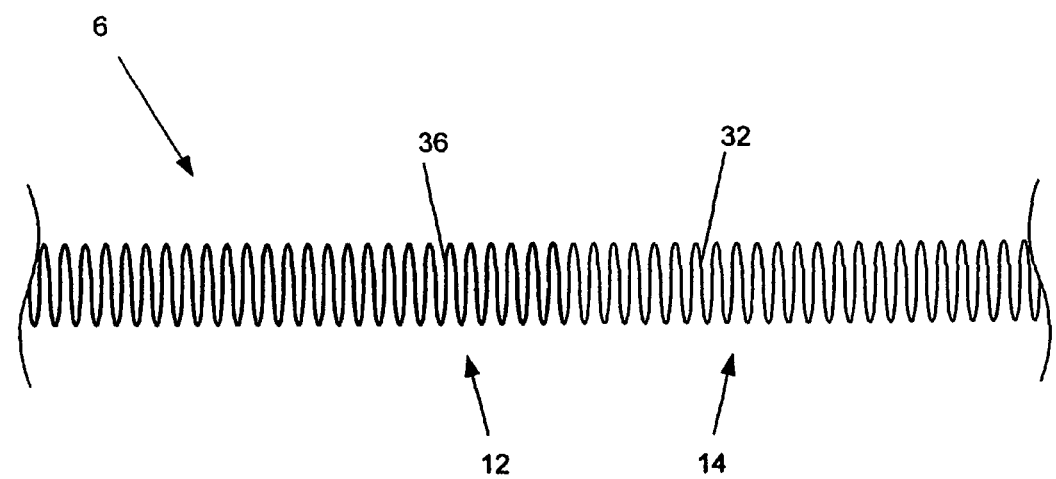

FIG. 4 illustrates that the anchor angle section 12 and the anchor extension section 14 can have a flexible elongated element. The flexible elongated element can be resilient and/or deformable. The flexible elongated element can have an integral, or multiple separate and fixedly attached, wound wire 32. The anchor angle section 12 can be in a sheath 34. FIG. 5 illustrates that the anchor angle section 12 can have a wire coating 36, for example a lubricious coating and/or a coating made from urethane.

Figure 6:
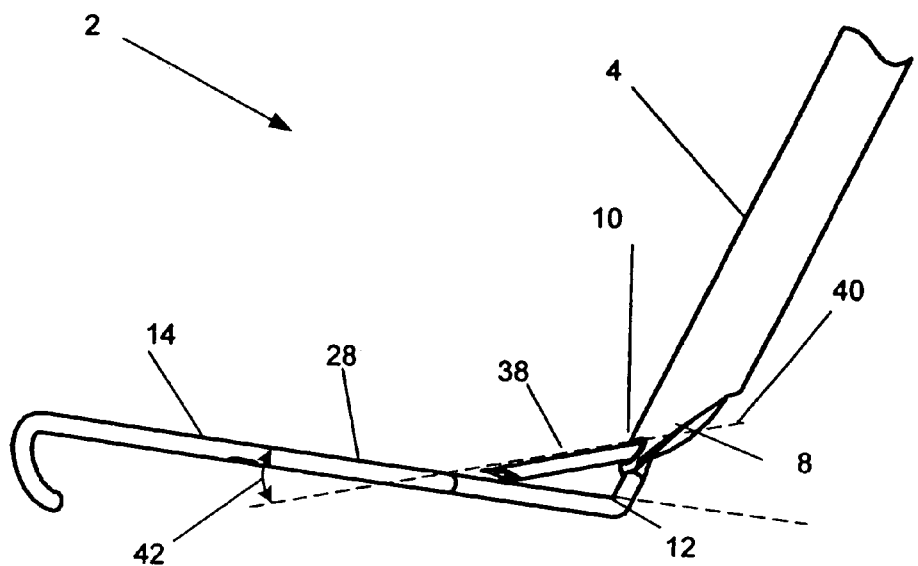
FIG. 6 is a side perspective view of an embodiment of the arteriotomy device with the introduction device deployed.
Figure 7:
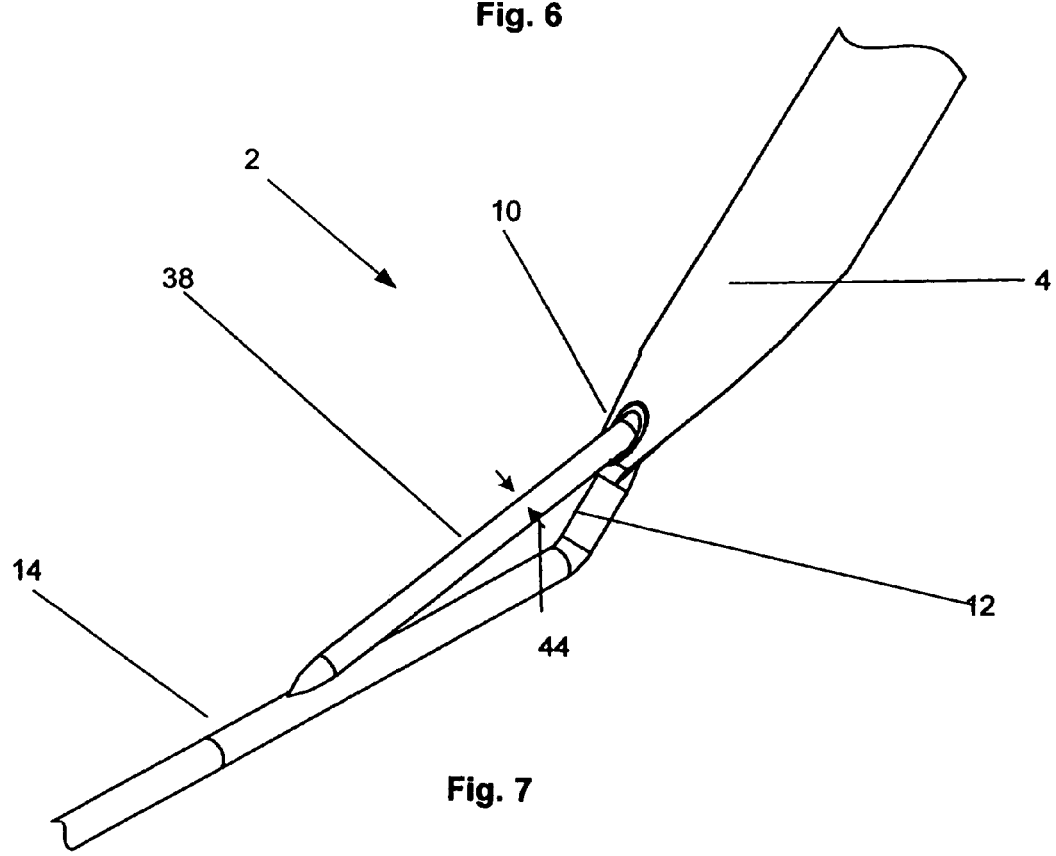
FIG. 7 is a close-up view of an embodiment of the arteriotomy device with the introduction device deployed.

FIGS. 6 and 7 illustrate that the arteriotomy device 2 can have an introduction device 38. The introduction device 38 can be slidably attached to the introducer lumen 8. The introduction device 38 can have a hollow needle (as shown in FIG. 6). The introduction device 38 can have a solid needle (as shown in FIG. 7). The introduction device 38 can have a guidewire.

The introduction device 38 can have an introduction longitudinal axis 40. The intersection of the introduction longitudinal axis 40 and the anchor longitudinal axis 28 can be an introduction angle 42. The introduction angle 42 can be less than or equal to about 19°, more narrowly less than or equal to about 15°, yet more narrowly from about 5° to about 10°, for example about °10.

The introduction device 38 can have an introduction device diameter 44. The introduction device diameter 44 can be from about 0.25 mm (0.010 in.) to about 1.0 mm (0.039 in.), for example about 0.56 mm (0.022 in.).

Figure 8:
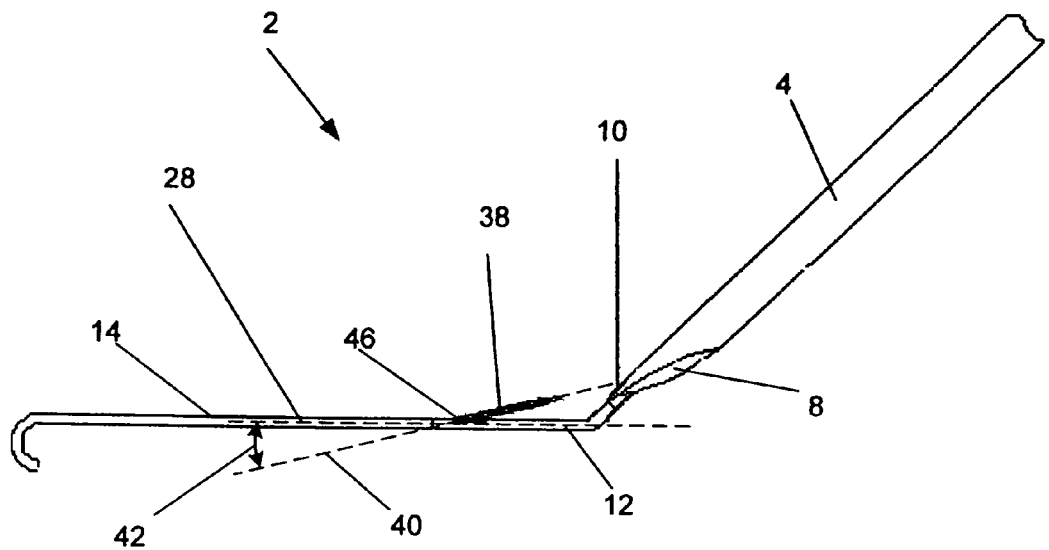
FIGS. 8 and 9 are side views of various embodiments of the arteriotomy device with the introduction devices deployed.
Figure 9:
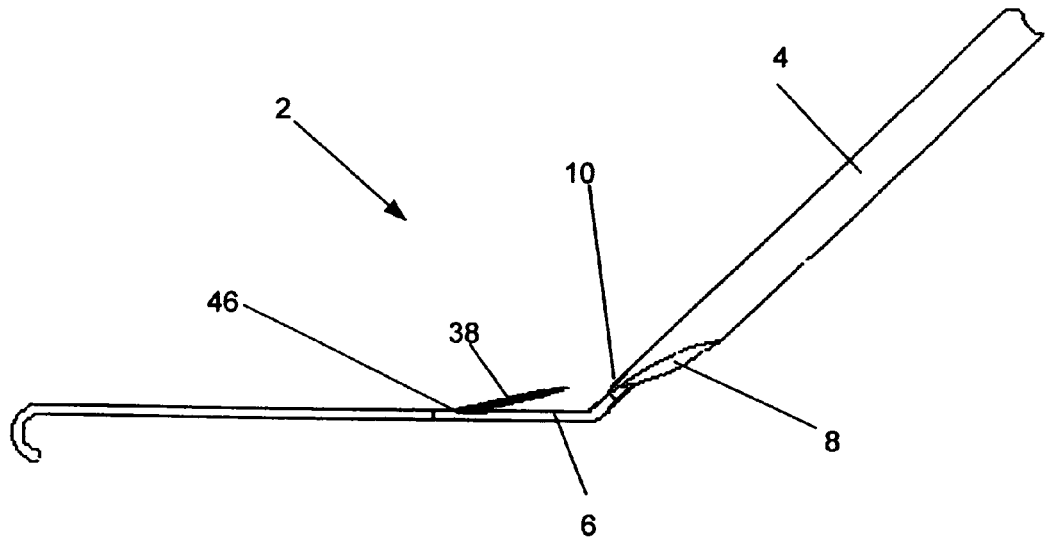

FIGS. 8 and 9 illustrate that the arteriotomy device 2 can be configured so that the introduction device 38 can be deployed from the anchor 6. The anchor 6 can have an introduction device port 46. The introduction device 38 can be a hollow needle (as shown in FIG. 8). When fully deployed, the introduction device 38 can contact the introducer lumen exit port 10. The introduction device 38 can be a channel between the introducer lumen 8 and the anchor 6. The anchor 6 can have a port (not shown) configured to communicate with the biological lumen and the introduction device 38. The introduction device 38 can be a solid needle (as shown in FIG. 9).

Figure 10:
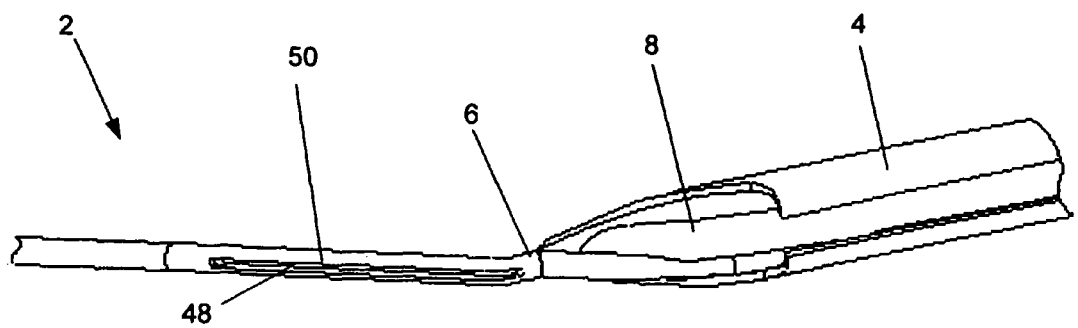
FIG. 10 is a bottom perspective view of an embodiment of the arteriotomy device.

FIG. 10 illustrates that a lumenal retainer 48 can have a first retracted configuration. The lumenal retainer 48 can be seated in a lumenal retainer port 50. The lumenal retainer port 50 can be in the anchor 6. The lumenal retainer 48 can be a wire, scaffold or stent—for example made from a deformable or resilient material, such as a shape memory alloy—an inflatable balloon, or combinations thereof. Intralumenal inflatable balloons, such as those inflated with saline solution or carbon dioxide, are known to those having ordinary skill in the art. The lumenal retainer 48 can extend into the delivery guide 4.

Figure 11:
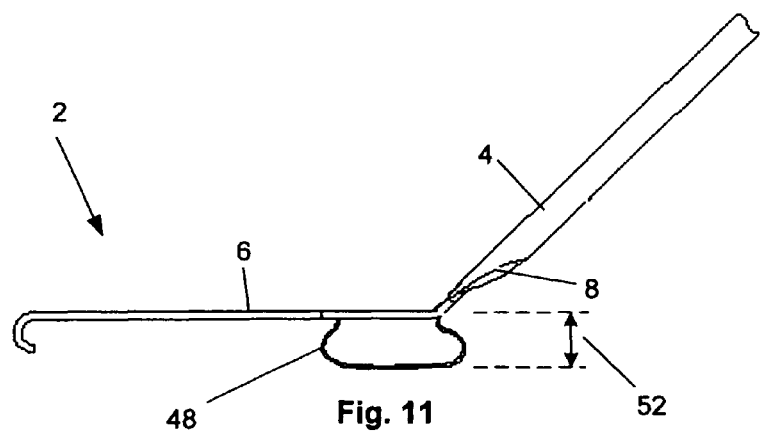
FIG. 11 is a side view of an embodiment of the arteriotomy device with the lumenal retainer deployed.
Figure 12:
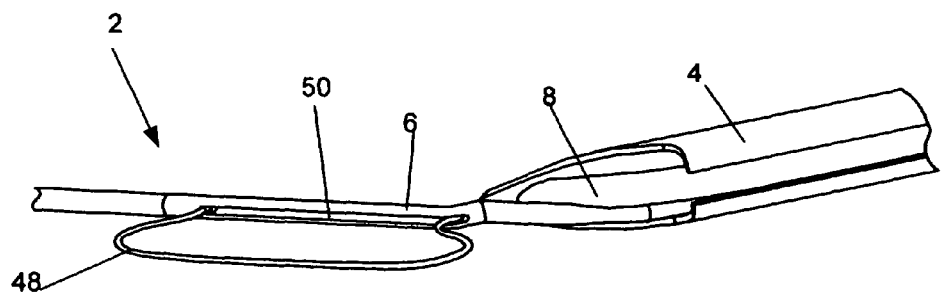
FIG. 12 is a bottom perspective view of an embodiment of the arteriotomy device with the lumenal retainer deployed.

FIGS. 11 and 12 illustrate that the lumenal retainer 48 can have a second deployed configuration. FIG. 11 shows that the lumenal retainer 48 can be a wire or balloon. FIG. 12 shows that the lumenal retainer 48 can be a wire. In the deployed configuration, the lumenal retainer 48 can deploy away from the lumenal retainer port. The lumenal retainer 48 can have a lumenal retainer deployed diameter 52. The lumenal retainer deployed diameter 52 can be from about 2.54 mm (0.100 in.) to about 10.2 mm (0.400 in.), for example about 6.35 mm (0.250 in.).

Figure 13:
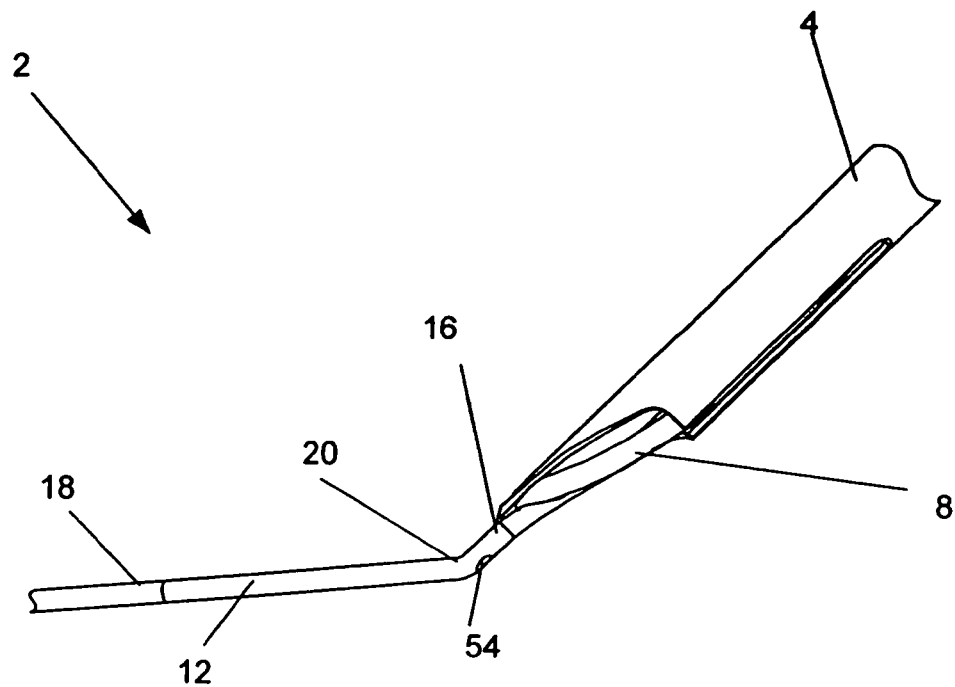
FIG. 13 is a side perspective view of an embodiment of the arteriotomy device.

FIG. 13 illustrates that the arteriotomy device 2 can have an entry wall retainer port 54. The entry wall retainer port 54 can be at or near the anchor bend 20. The entry wall retainer port 54 can be at or near the anchor angle first sub-section 16. The entry wall retainer port 54 can be in fluid communication with a sensor or port (not shown) on or near the delivery guide 4 of the arteriotomy device 2.

Figure 14:
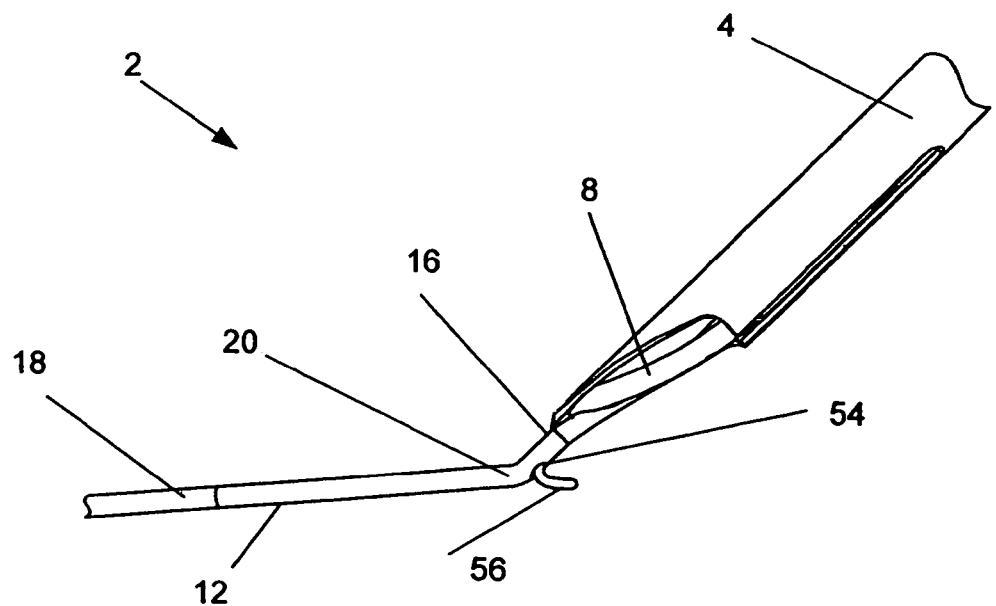
FIG. 14 is a side perspective view of an embodiment of the arteriotomy device with the entry wall retainer deployed.

FIG. 14 illustrates that an entry wall retainer 56 can be deployed through the entry wall retainer port 54. The entry wall retainer 56 can have a first retracted configuration (as shown in FIG. 13). The entry wall retainer 56 can have a second deployed configuration (as shown in FIG. 14).

FIGS. 15 through 20 illustrate various supplemental closure devices. The supplemental closure devices can be completely or partially bioabsorbable, bioresorbable, bioadsorbable or combinations thereof. The supplemental closure devices can be made from homografts, heterografts or combinations thereof. The supplemental closure devices can be made from autografts, allografts or combinations thereof.

Figure 15:
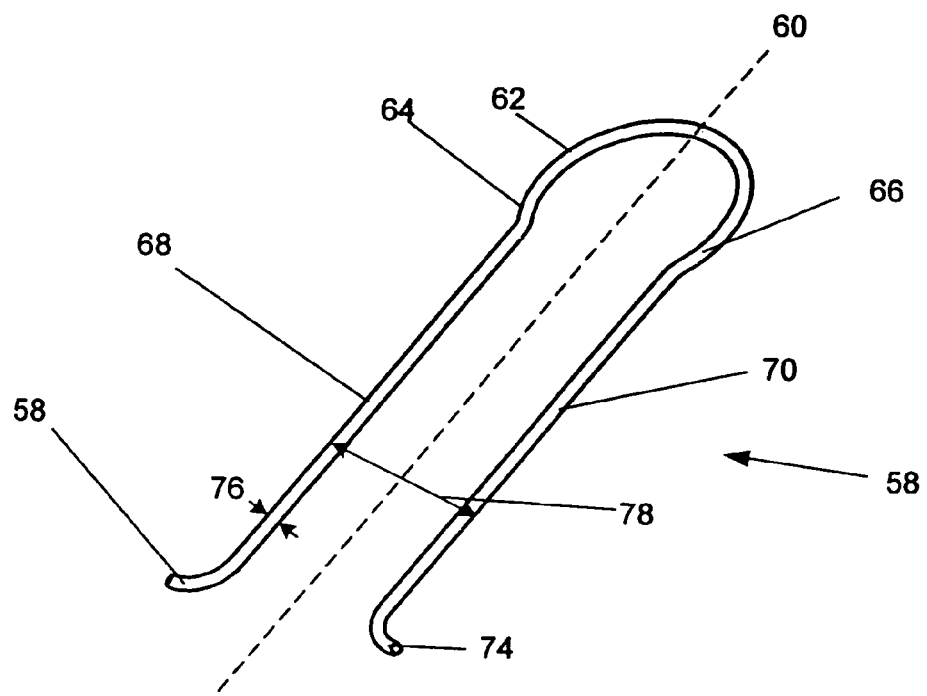
FIGS. 15 and 16 illustrate various embodiments of the tensioner.

FIG. 15 illustrates a tensioner 58. The tensioner 58 can be resilient, deformable, or combinations thereof. The tensioner 58 can have a tensioner longitudinal axis 60. The tensioner 58 can have a resilient element, such as a spring, for example a tensioner head 62. The tensioner head 62 can have a tensioner first shoulder 64. The tensioner head 62 can have a tensioner second shoulder 66. The tensioner first and second shoulders 64 and 66 can rotatably attached to a separate or integral tensioner first leg 68 and a separate or integral tensioner second leg 70, respectively. The tensioner first and second legs 68 and 70 can attach to tensioner first and second feet 72 and 74, respectively.

The tensioner legs 68 and 70 can have tensioner leg diameters 76. The tensioner leg diameters 76 can be from about 0.1 mm (0.005 in.) to about 0.76 mm (0.030 in.), for example about 0.38 mm (0.015 in.). The tensioner first and second legs 68 and 70 can have a tensioner inter-leg outer diameter 78. The tensioner inter-leg outer diameter 78 can be from about 1.3 mm (0.050 in.) to about 5.08 mm (0.200 in.), for example about 4.06 mm (0.160 in.). The tensioner shoulders 64 and/or 66 and/or the tensioner feet 72 and/or 74 can extend to a greater radius from the tensioner longitudinal axis 60 than their respective tensioner inter-leg radius.

Figure 16:
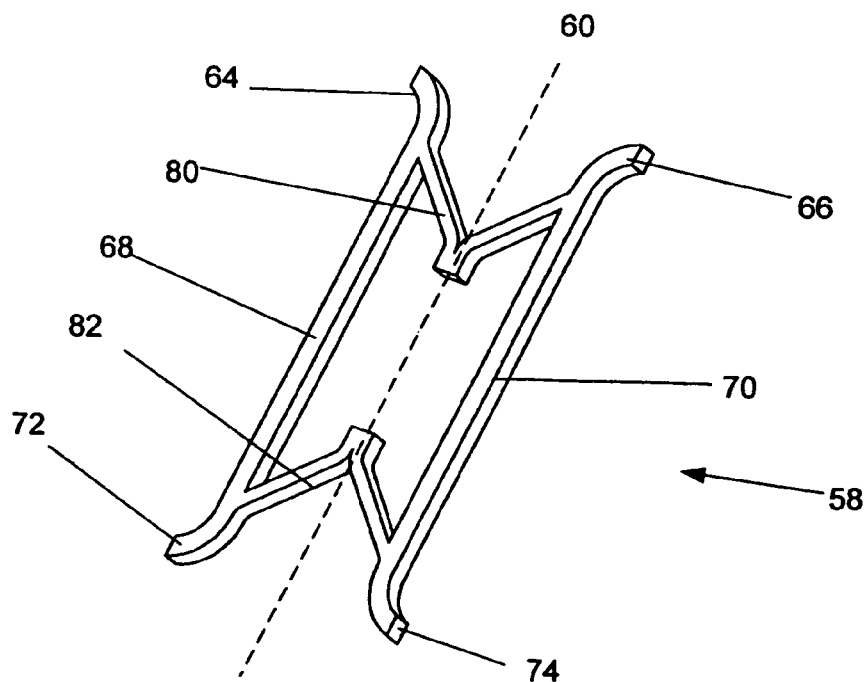

FIG. 16 illustrates a tensioner first strut 80 that can attach to the tensioner first leg 68 and the tensioner second leg 70. The tensioner first leg 68 can be resilient, deformable or combinations thereof. A tensioner second strut 82 can attach to the tensioner first leg 68 and the tensioner second leg 70. The tensioner second leg 70 can be resilient and/or deformable. The tensioner 58 can have no tensioner head 62. The tensioner 58 can have more than two tensioner struts 80 and 82.

Figure 17:
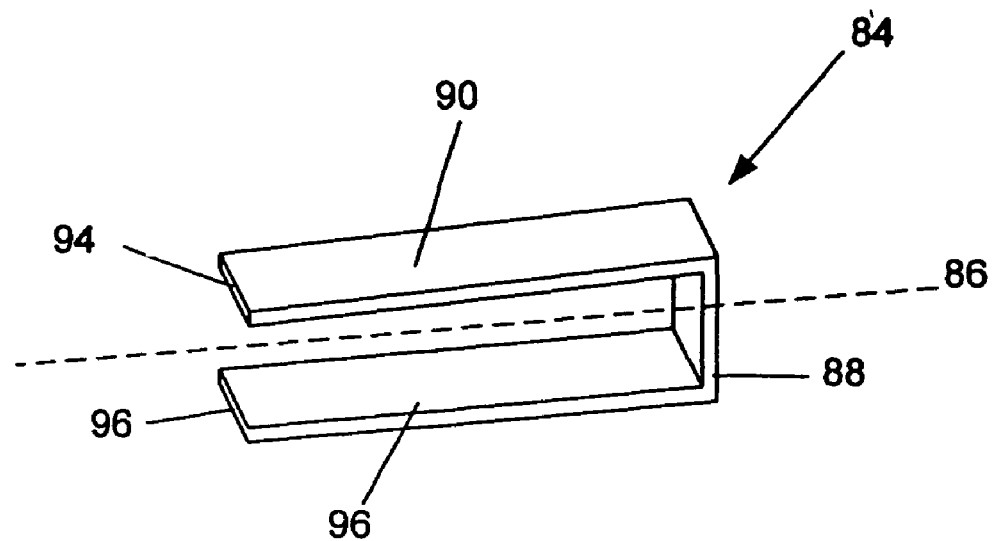
FIGS. 17 and 18 illustrate various embodiments of the pressure clip.

FIG. 17 illustrates a pressure clip 84. The pressure clip 84 can be resilient. The pressure clip 84 can be deformable. The pressure clip 84 can have a pressure clip longitudinal axis 86. The pressure clip 84 can have a pressure, clip head 88. The pressure clip head 88 can be rotatably attached to a separate or integral pressure clip first leg 90. The pressure clip head 88 can be rotatably attached to a separate or integral pressure clip second leg 92. The pressure clip can have a pressure clip first end 94 and a pressure clip second end 96. The pressure clip first leg 90 can terminate in the pressure clip first end 94. The pressure clip second leg 92 can terminate in the pressure clip second end 96. The pressure clip first leg 90 and/or the pressure clip second leg 92 can be biased toward the pressure clip longitudinal axis 86.

Figure 18:
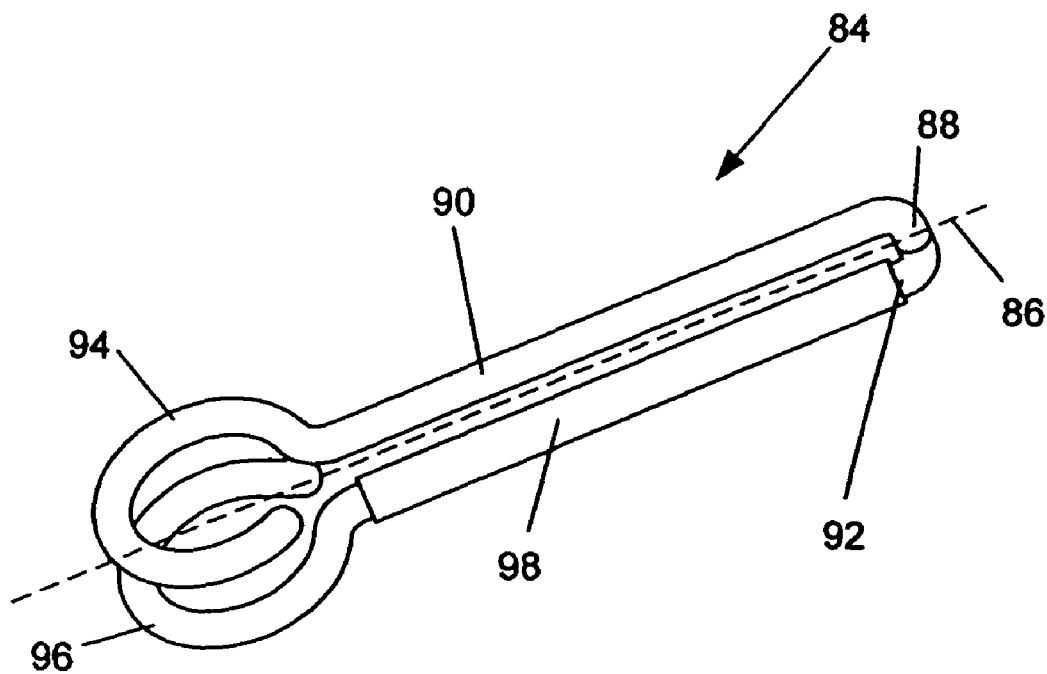

FIG. 18 illustrates the pressure clip 84 that can have a pressure clip sheath 98 slidably attached to the pressure clip second leg 92. The pressure clip first, and/or second ends 94 and/or 96 can be pressure dissipaters, such as flat and/or curved portions, for example circular loops. The pressure clip first and/or second ends 94 and/or 96 can be resilient and/or deformable. The pressure clip first leg 90 can be rotatably attached to the pressure clip second leg 92. The pressure clip first leg 90 can be attached to the pressure clip second leg 92 via a rotatable, and/or deformable, and/or flexural joint in the pressure clip head 88.

Figure 19:
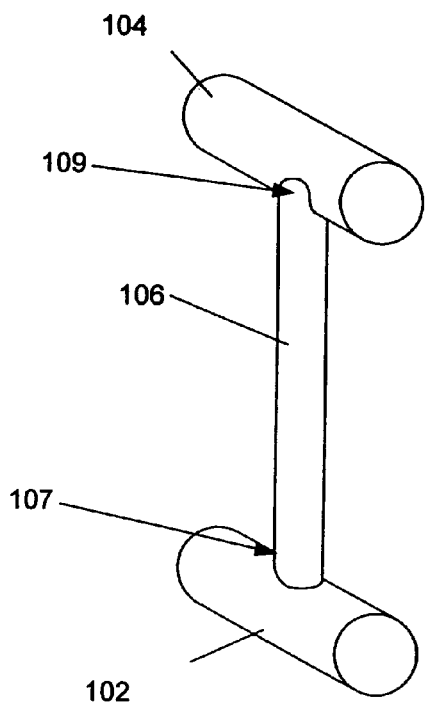
FIGS. 19 and 20 illustrate various embodiments of the toggle.

FIG. 19 illustrates a toggle 100. The toggle 100 can have a toggle first end 102. The toggle 100 can have a toggle second end 104. The toggle first and/or second ends 102 and/or 104 can be bars, dowels, rods, beams, or combinations thereof. The toggle 100 can have a filament 106. The filament 106 can be fixedly attached at a filament first end 107 to the toggle first end 102. The filament 106 can be fixedly attached at a filament second end 109 to the toggle second end 104. The filament 106 can be resilient or deformable. The filament 106 can be substantially flexible.

Figure 20:
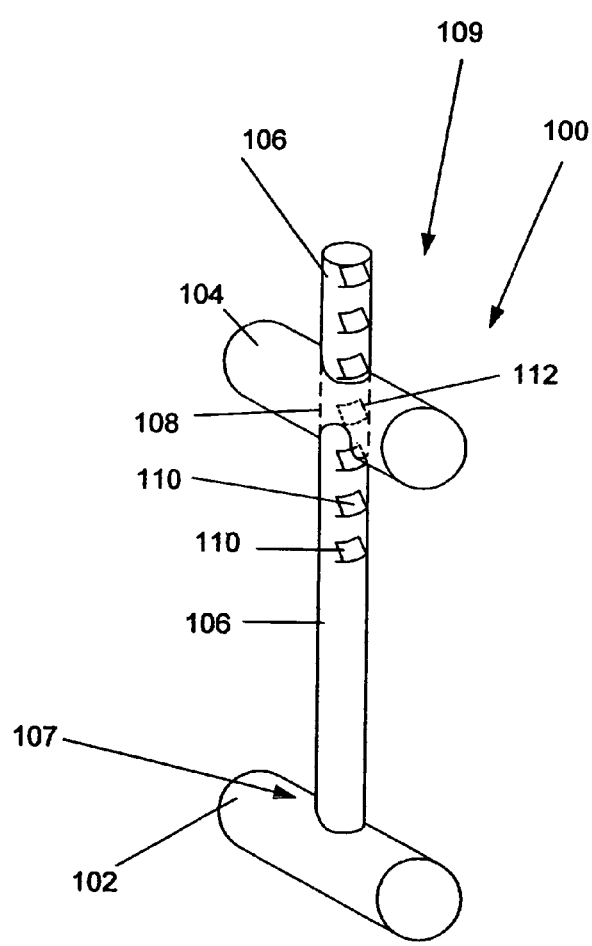

FIG. 20 illustrates the toggle 100 that can have the filament 106 that can be slidably attached to the toggle second end 104 at a hole 108. The filament 106 can frictionally fit the hole 108. The filament 106 can have no pawls 110 (not shown in FIG. 20). The filament 106 can interference fit the hole 108. The filament 106 can have one or more pawls 110. The hole 108 can have one or more notches 112. The notches 112 can be internal to the hole 108. The notches 112 and the pawls 110 can be configured to allow the toggle second end 104 to slide toward the toggle first end 102. The notches 112 and the pawls 110 can be configured to provide an interference fit when the toggle second end 104 is attempted to be moved away from the toggle first end 102.

Method of Manufacture

The elements of the arteriotomy device 2, including the supplemental closure devices, can be directly attached by, for example, melting, screwing, gluing, welding or use of an interference fit or pressure fit such as crimping, snapping, or combining methods thereof. The elements can be integrated, for example, molding, die cutting, laser cutting, electrical discharge machining (EDM) or stamping from a single piece or material. Any other methods can be used as known to those having ordinary skill in the art.

Integrated parts can be made from pre-formed resilient materials, for example resilient alloys (e.g., Nitinol, ELGILOY® that are preformed and biased into the post-deployment shape and then compressed into the deployment shape as known to those having ordinary skill in the art.

Any elements of the arteriotomy device 2, including the supplemental closure devices, or the arteriotomy device 2, including the supplemental closure devices, as a whole after assembly, can be coated by dip-coating, brush-coating or spray-coating methods known to one having ordinary skill in the art For example, these methods can be used to coat the wound wire 32 with the wire coating 36 can be spray coated, dip-coated or brushed onto the wire 32.

One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating, for example the coatings on the supplemental closure devices.

The supplemental closure devices can be covered with a fabric, for example polyester (e.g., DACRON® from E. I. du Pont de Nemours and Company, Wilmington, Del.), polypropylene, PTFE, ePTFE, nylon, extruded collagen, silicone or combinations 7 thereof. Methods of covering an implantable device with fabric are known to those having ordinary skill in the art.

Method of Use

Figure 21:
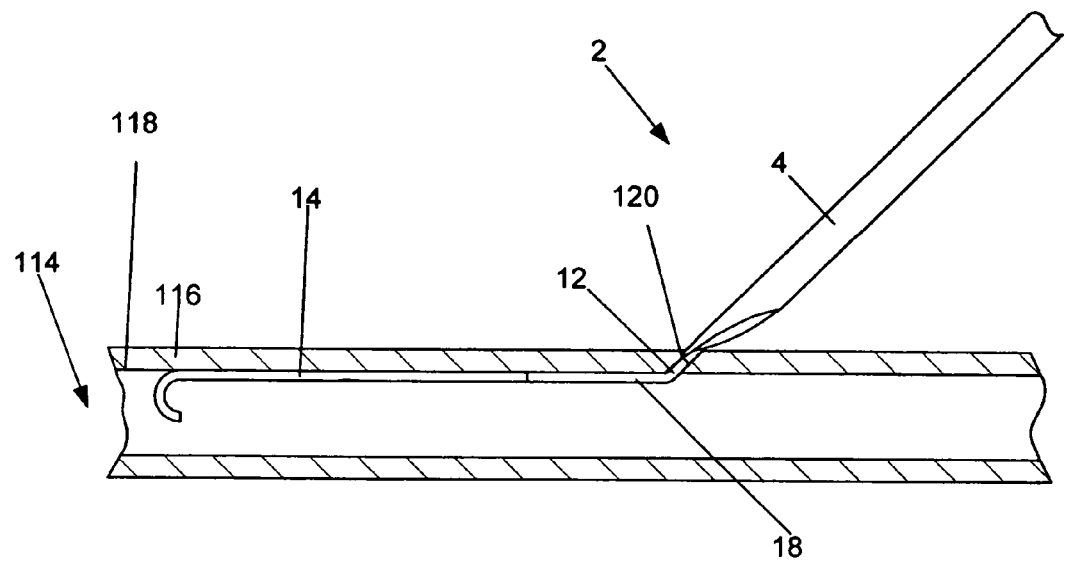
FIG. 21 illustrates a method for deploying the arteriotomy device in a cross-section of a lumen.

FIG. 21 illustrates a method of inserting the anchor 6 into a biological lumen 114, for example a blood vessel, such as a femoral artery. The biological lumen 114 can have a lumen wall 116 and a lumen wall surface 118. The anchor 6 can be inserted into the biological lumen 114 using a Seldinger technique, modified Seldinger technique, or other method known to one having ordinary skill in the art. The anchor 6 can create a first arteriotomy 120. The anchor 6 can be inserted into the lumen 114 so that the anchor angle second sub-section 18 can be substantially parallel with the lumen wall surface 118. The anchor 6 can be inserted into the lumen 114 so that the anchor angle second sub-section 18 can be substantially in contact with the lumen wall surface 118.

Figure 22:
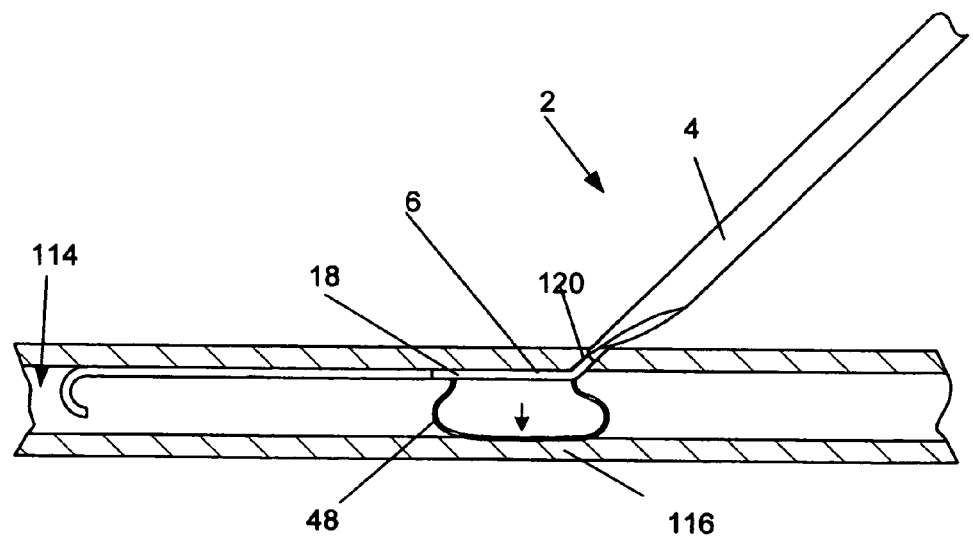
FIGS. 22 and 23 illustrate methods for deploying the retainers in a cross-section of a lumen.

FIG. 22 illustrates a method of deploying, as shown by arrow, the lumenal retainer 48 from the first retracted configuration to the second deployed configuration. The lumenal retainer 48 can be deployed by extending a wire, scaffold or stent, or by inflating a balloon. When the lumenal retainer 48 is deployed, the anchor angle second sub-section 18 can be made substantially parallel with the lumen wall surface 118. When the lumenal retainer 48 is deployed, the anchor angle second sub-section 18 can be made to be substantially in contact with the lumen wall surface 118.

Figure 23:
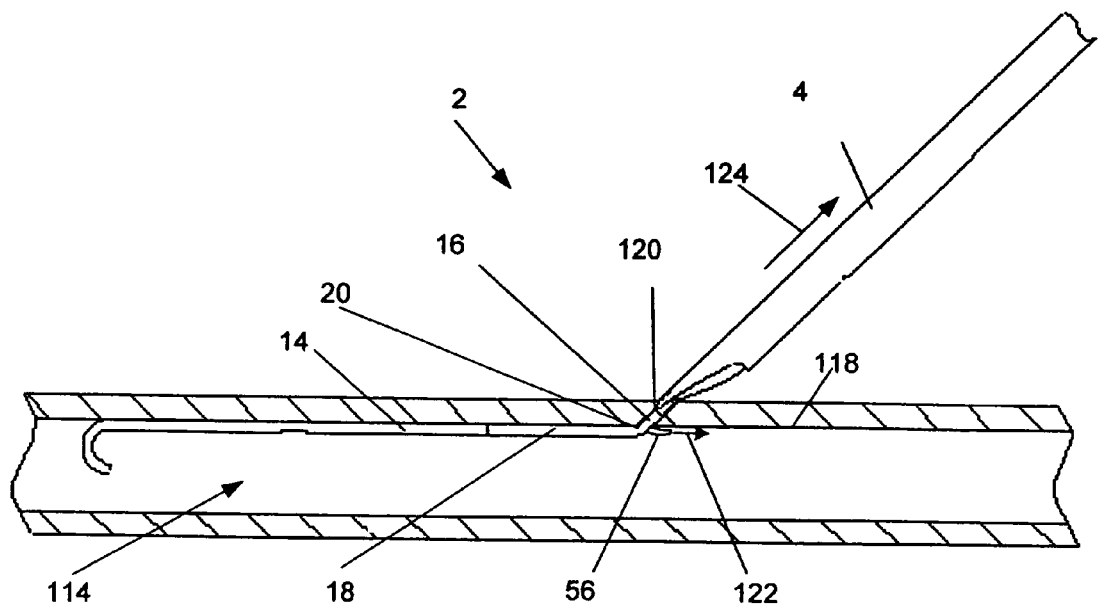

FIG. 23 illustrates a method of deploying, as shown by arrow 122, the entry wall retainer 56 from the first retracted configuration to the second deployed configuration. When the lumenal retainer is in the second deployed configuration, the lumenal retainer 48 can be substantially parallel with the lumen wall surface 118. When the lumenal retainer is in the second deployed configuration, the lumenal retainer 48 can be substantially in contact with the lumen wall surface 118.

A proximal force, as shown by arrow 124, can be applied to the anchor 6, for example by being applied to the delivery guide 4. When the proximal force is applied, the anchor angle second sub-section 18 can be made substantially parallel with the lumen wall surface 118. When the proximal force is applied, the anchor angle second sub-section 18 can be made to be substantially in contact with the lumen wall surface 118.

Figure 24:
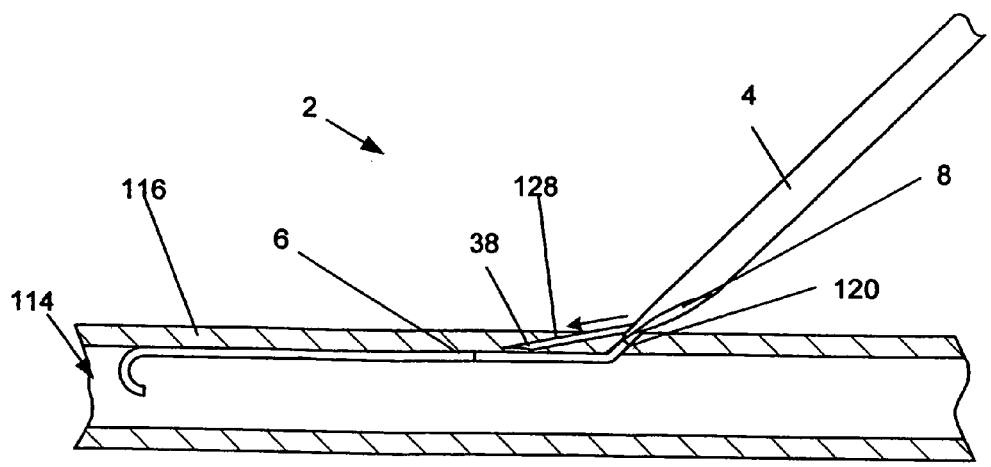
FIGS. 24 and 25 illustrate a method for deploying the introduction device in a cross-section of a lumen.
Figure 25:
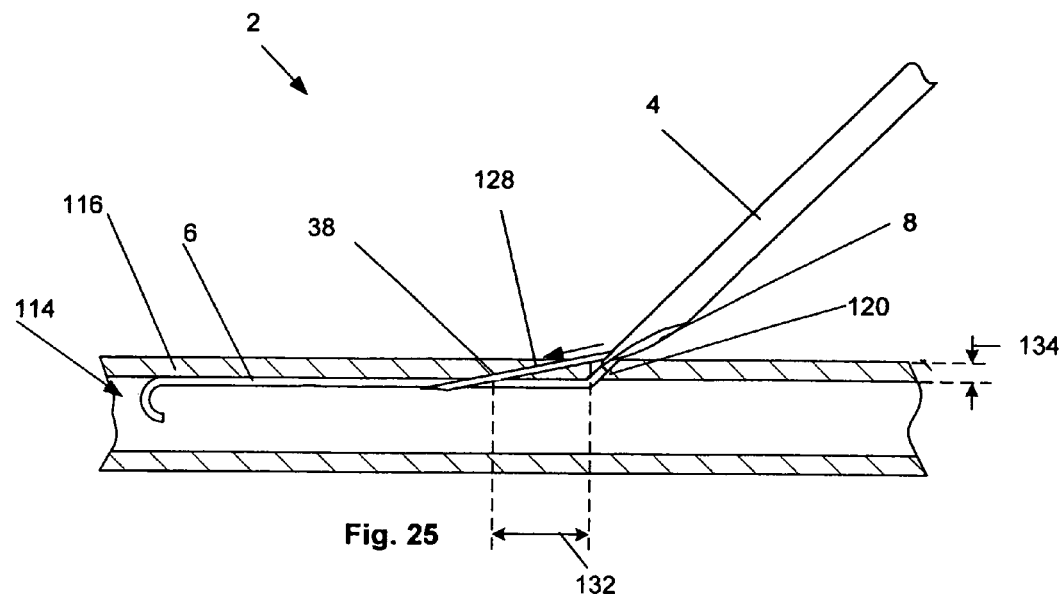

FIGS. 24 and 25 illustrate a method for deploying the introduction device 38. The introduction device 38 can egress from the introducer lumen 8 and the introducer lumen exit port 10. As shown in FIG. 24, the introduction device 38 can be pushed, as shown by arrow, into and through the lumen wall 116. The introduction device 38 can form a second arteriotomy 128. As shown in FIG. 25, the introduction device 38 can be pushed, as shown by arrow, adjacent to or through the anchor 6. The anchor 6 can be configured to have ports suitable to allow the introduction device 38 to pass through the anchor 6. A tip of the introduction device 38 can enter the lumen 114.

The introduction device 38 can pass through an introduction run 132 and an introduction rise 134. The introduction run 132 can be the component of the length of the introduction device 38 in the lumen wall 116 that is parallel to the lumen wall 116. The introduction run 132 can be the component of the length parallel to the lumen wall 116 between the opening of the second arteriotomy 128 on the outside of the lumen wall 116 and the opening of the second arteriotomy 128 on the inside lumen wall surface 118. The introduction run 132 can be from about 0.10 cm (0.010 in.) to about 3.810 cm (1.500 in.), for example about 0.64 cm (0.25 in.).

The introduction rise 134 can be the component of the length of the introduction device 38 in the lumen wall 116 that is perpendicular to the lumen wall 116. The introduction rise 134 can be the component of the length perpendicular to the lumen wall 116 between the opening of the second arteriotomy 128 on the outside of the lumen wall 116 and the opening of the second arteriotomy 128 on the inside lumen wall surface 118. The introduction rise 134 can be from about 0.51 mm (0.020 in.) to about 5.08 mm (0.200 in.), for example about 1.0 mm (0.040 in.). An introduction slope can be the ratio of the introduction rise 134 to the introduction run 132. The introduction slope can be from about ½ to about ¹⁄₄₀ or less, for example about ⅙, also for example about ⅓. The introduction slope can be, for examples, equal to or less than about ½ or ⅓, more narrowly equal to or less than about ⅓ or ¼, yet more narrowly equal to or less than about ⅕ or ⅙, even still more narrowly than about equal to or less than about ¹⁄₁₀.

The introduction rise 134 and the introduction run 132 can be components of an introduction vector. The introduction run 132 can be the component of the introduction vector parallel to the lumen wall 116. The introduction rise 134 can be the component of the introduction vector perpendicular to the lumen wall 116. The introduction vector can be a vector from an outer opening 136 to an inner opening 138. The outer opening 136 can be a temporary or permanent opening on the outside of the lumen wall 116 formed by the introduction device 38. The inner opening 138 can be a temporary or permanent opening on the inside of the vessel wall.

Figure 26:
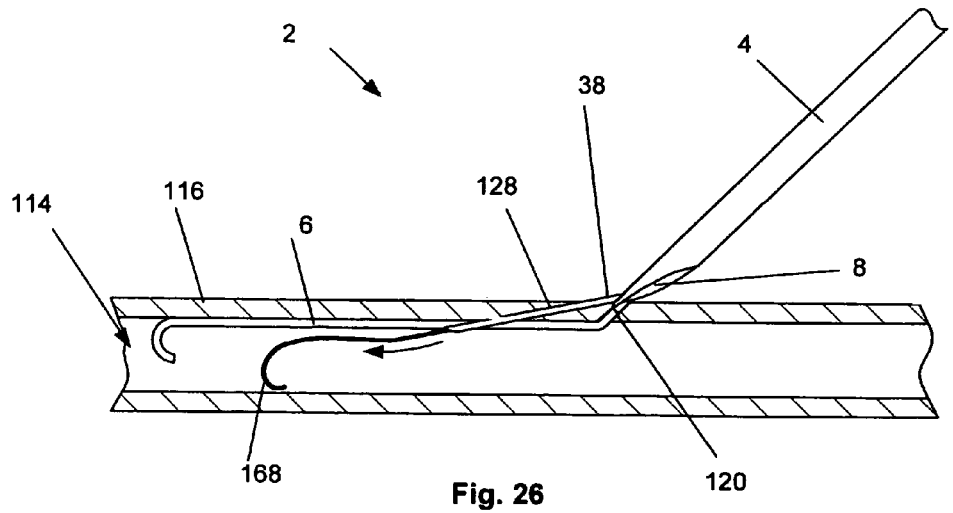
FIG. 26 illustrates a method for deploying a guidewire in a cross-section of a lumen.

FIG. 26 illustrates that the introduction-device 38, for example a hollow needle, can act as a pathway for a lumenal tool, for example tools such as a guidewire 168, to be deployed, as shown by arrow, into the lumen 114. The introduction device 38, for example a solid needle, can be removed from the second arteriotomy 128 and the lumenal tool can be deployed through, for example, the introducer lumen exit port 10, and the second arteriotomy 128. The introduction device 38 can be the lumenal tool, for example a guidewire. The introduction device 38 can be further deployed and used as a lumenal tool after passing through the lumen wall 116.

Figure 27:
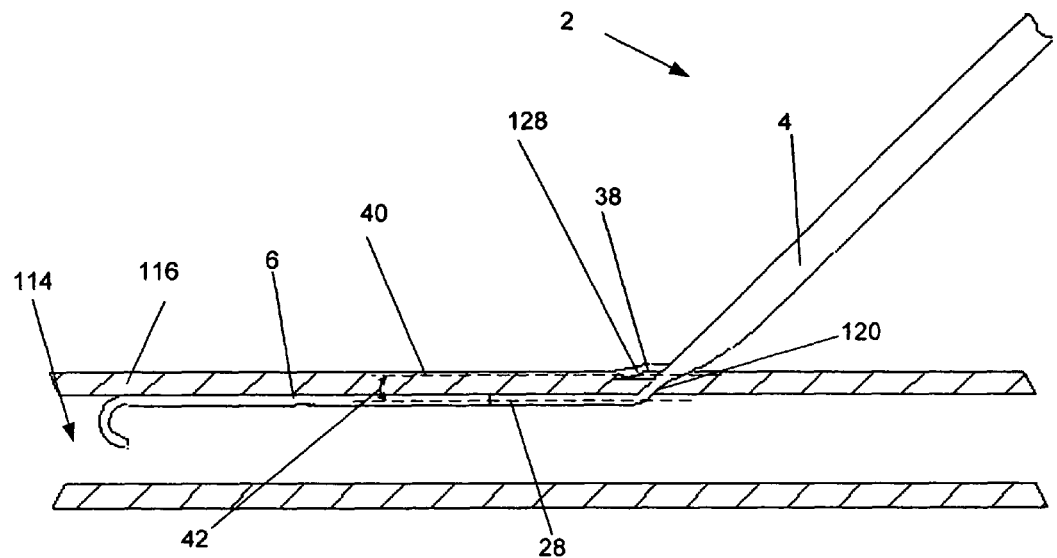
FIGS. 27-30 illustrate a method for deploying the introduction device in a cross-section of a lumen.

FIGS. 27 through 30 illustrates a method of deploying the introduction device 38 that can have a pre-formed bend. As shown in FIG. 27, the arteriotomy device 2 can be configured to deploy the introduction device 38 at the introduction angle 42 from about 0° to about 5°, for example about 0°.

Figure 28:
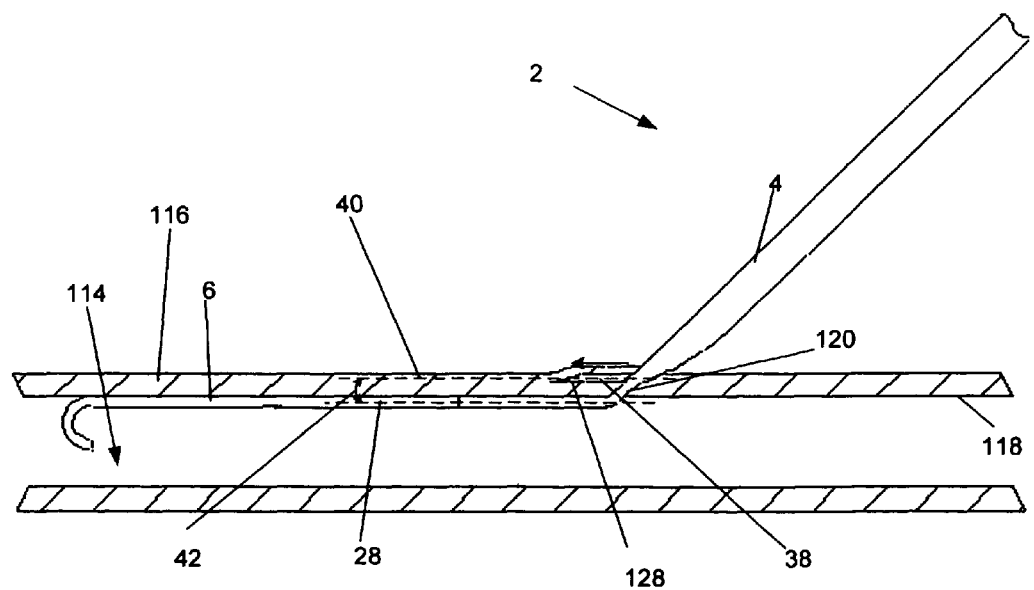

As shown in FIG. 28, the introduction device 38 can be pushed, as shown by arrow, through the lumen wall 116. The introduction device 38 can cleave a plane in the lumen wall 116. The plane can be substantially parallel with the lumen wall surface 118. The introduction device 38 can be adjacent to the adventitia in a blood vessel. The introduction device 38 can be advanced along the subintimal or submedial cleavage plane in a blood vessel. Once the lumen wall has been cleaved, a subintimal angioplasty can be performed as known to one having ordinary skill in the art. Once the lumen wall has been cleaved, a remote endarterectomy can be performed as known to one having ordinary skill in the art. Bent and straight introduction devices 38 can be swapped during use to selectively cleave the lumen wall 116. Tools, such as guidewires, can be inserted through hollow introduction devices 38 to selectively cleave the lumen wall 116.

Figure 29:
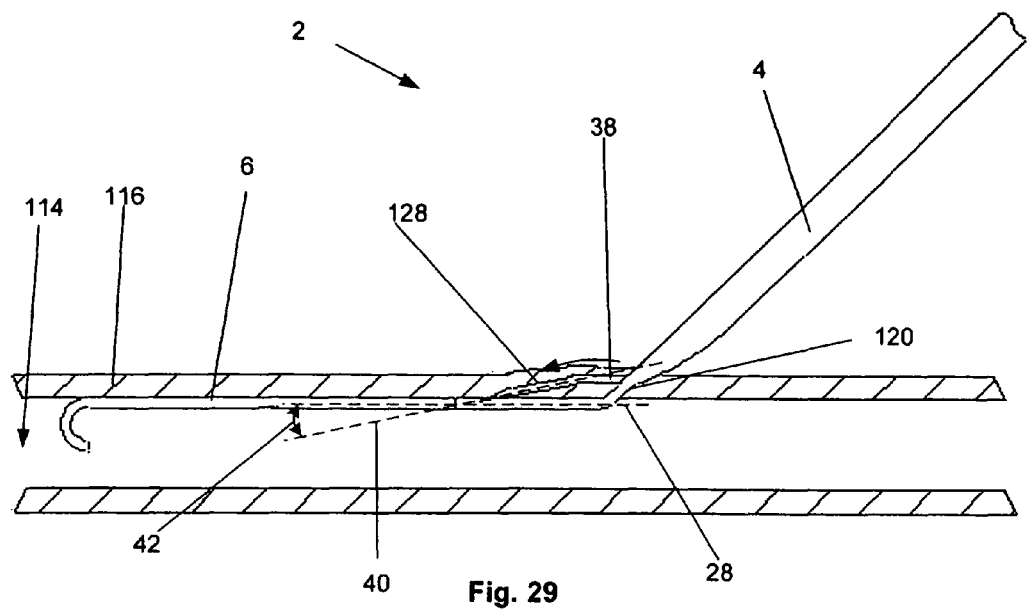
Figure 30:
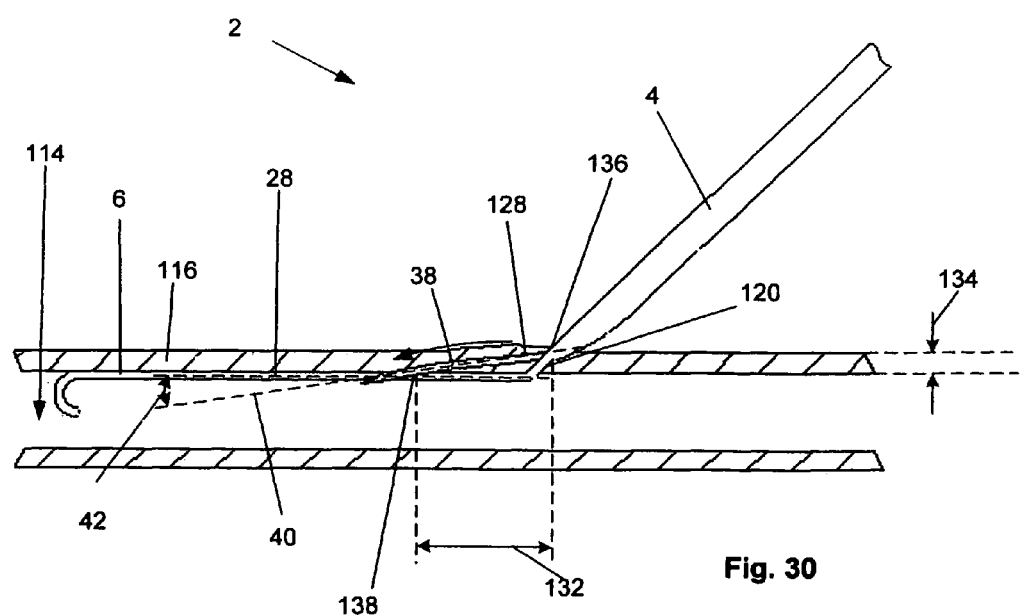
Figure 31:
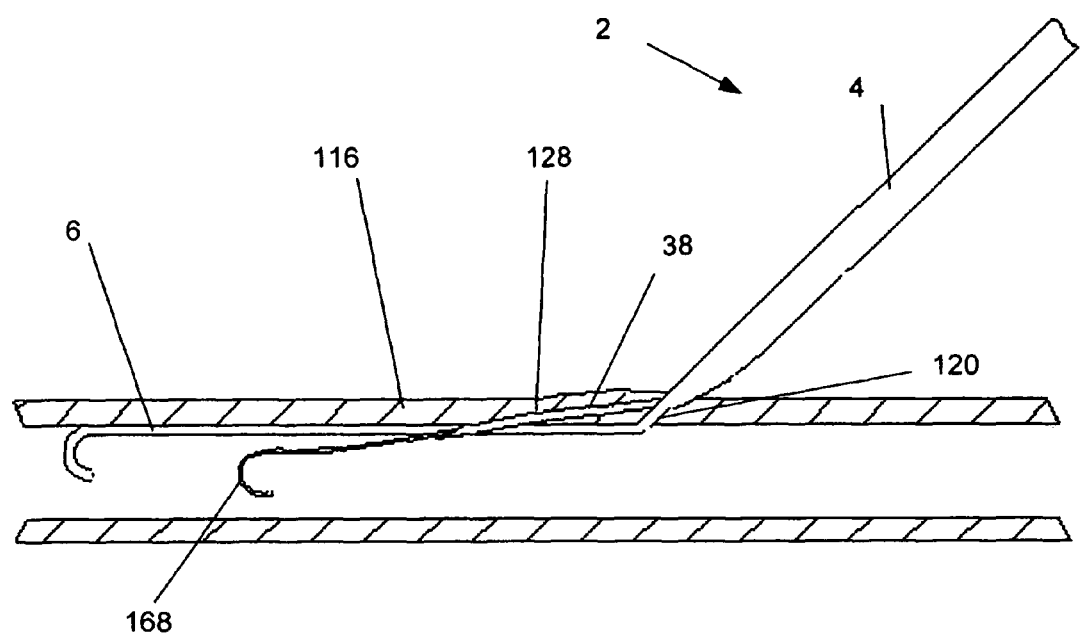
FIG. 31 illustrates a method for deploying a guidewire in a cross-section of a lumen.

As shown in FIG. 29, when the bend in the introduction device 38 moves into the lumen wall 116, the introduction device 38 can rotate, as shown by arrow, toward the biological lumen 114. As shown in FIG. 30, the bend in the introduction device 38 can continue to rotate the introduction device 38 toward the biological lumen 114. As described infra, the introduction device 38 can enter the lumen 114. FIG. 31 illustrates that the introduction device 38 that can have the bend can act as a pathway for a lumenal tool, as described infra.

An introducer sheath can be inserted over the guidewire 168 and/or the introduction device 38. The introducer sheath can be less than about 22 French (7.3 mm, 0.29 in. diameter) or less than the diameter of the lumen to which the introducer sheath is introduced. The introducer sheath can be, for examples, about 6 French (2.3 mm, 0.092 in. diameter), and about 8 French (2.67 mm, 0.105 in. diameter). The introducer sheath can be known to one having ordinary skill in the art, for example the introducer sheath described in U.S. Pat. No. 5,183,464 to Dubrul, et al.

The introducer sheath can be inserted into the second arteriotomy 128. The introducer sheath can expand the second arteriotomy 128 to a workable size. The introducer sheath can be inserted into the second arteriotomy 128 before and/or after and/or concurrently with the supplemental closure device is deployed and/or other closure method is used.

Figure 32:
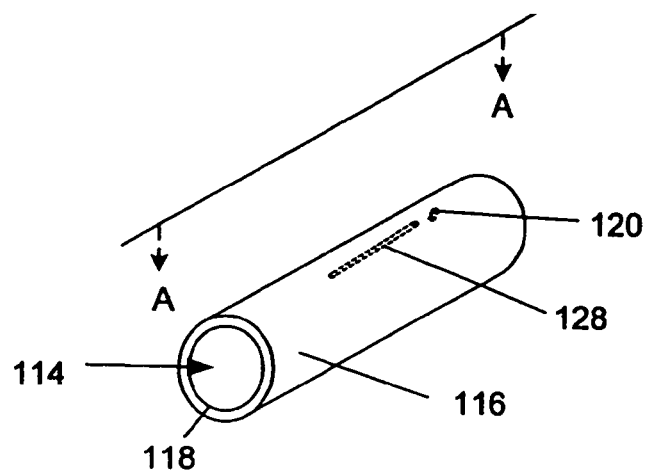
FIG. 32 illustrates a portion of an arteriotomized lumen.
Figure 33:
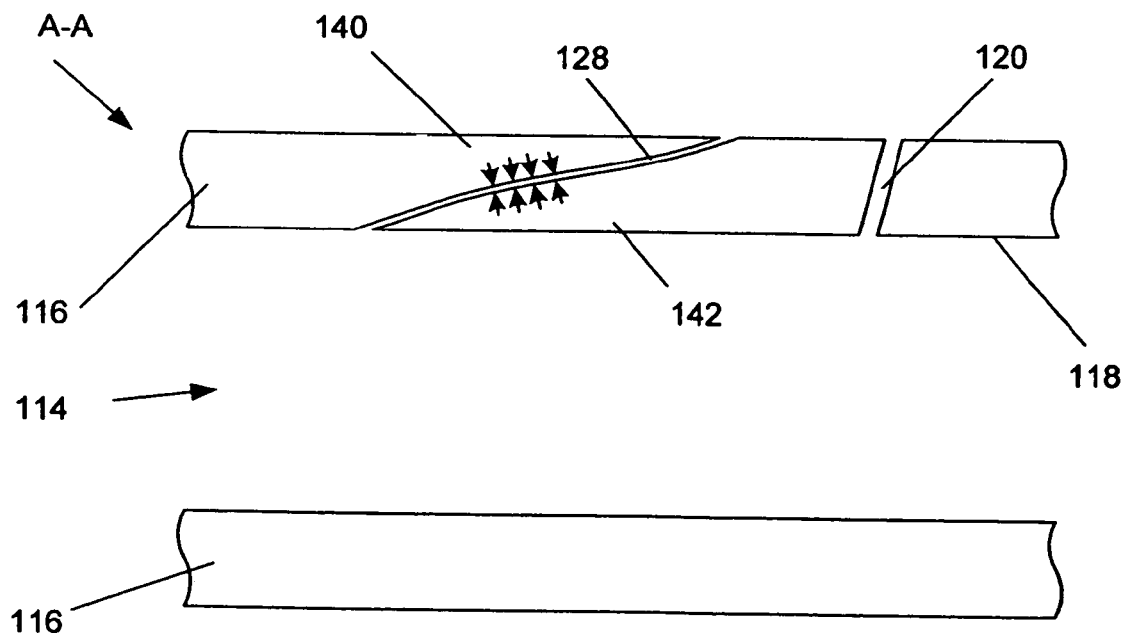
FIG. 33 illustrates section A-A of FIG. 28.

FIGS. 32 and 33 illustrate an exemplary biological lumen 114 after the arteriotomy device 2 has been deployed to, and removed from, the biological lumen 114. The biological lumen 114 can have the first and second arteriotomies 120 and 128. The biological lumen 114 can have a second arteriotomy 128. The biological lumen 114 can have a first web 140 on one side of the arteriotomy (shown for the second arteriotomy 128), and a second web 142 on the opposite side of the arteriotomy 120 or 128. The natural pressure, shown by arrows, from the first and second webs 140 and 142 can self-seal the arteriotomy 120 or 128.

One or more supplemental closure devices can be deployed to the first and/or second arteriotomies 120 and/or 128. The supplemental closure devices can provide a force or restraint to aid hemostasis. The supplemental closure devices can be permanently or temporarily deployed. The supplemental closure devices can biodissolve after hemostasis is achieved and/or after the relevant arteriotomy 120 or 128 is substantially or completely healed. The force from the supplemental closure device can be maintained from about 15 minutes to about 24 hours or more, for example about 120 minutes.

Figure 34:
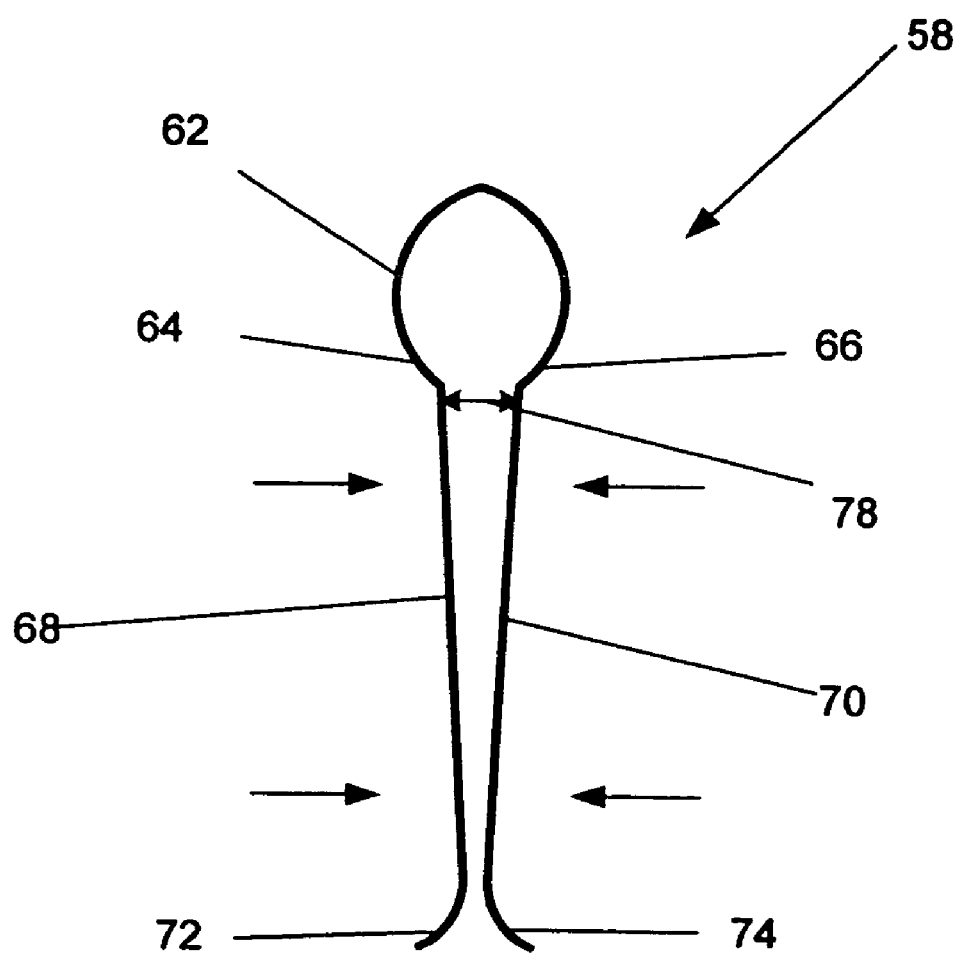
FIGS. 34-36 illustrate a method for deploying a tensioner in a see-through portion of lumen wall.

FIG. 34 illustrates a tensioner 58 in a compressed configuration. Compressive forces, shown by arrows, can compress the tensioner first and second legs 68 and 70. In a compressed configuration, the tensioner inter-leg outer diameter 78 can be from about 0.51 mm (0.020 in.) to about 2.54 mm (0.100 in.), for example about 1.5 mm (0.060 in.).

Figure 35:
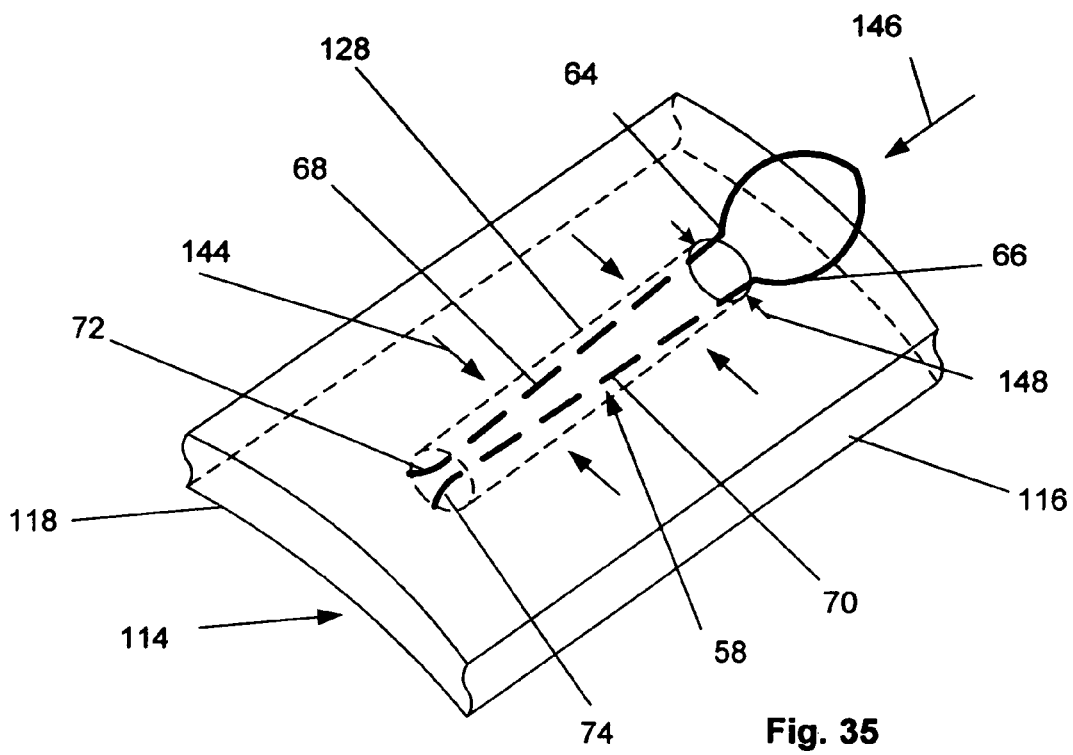
Figure 36:
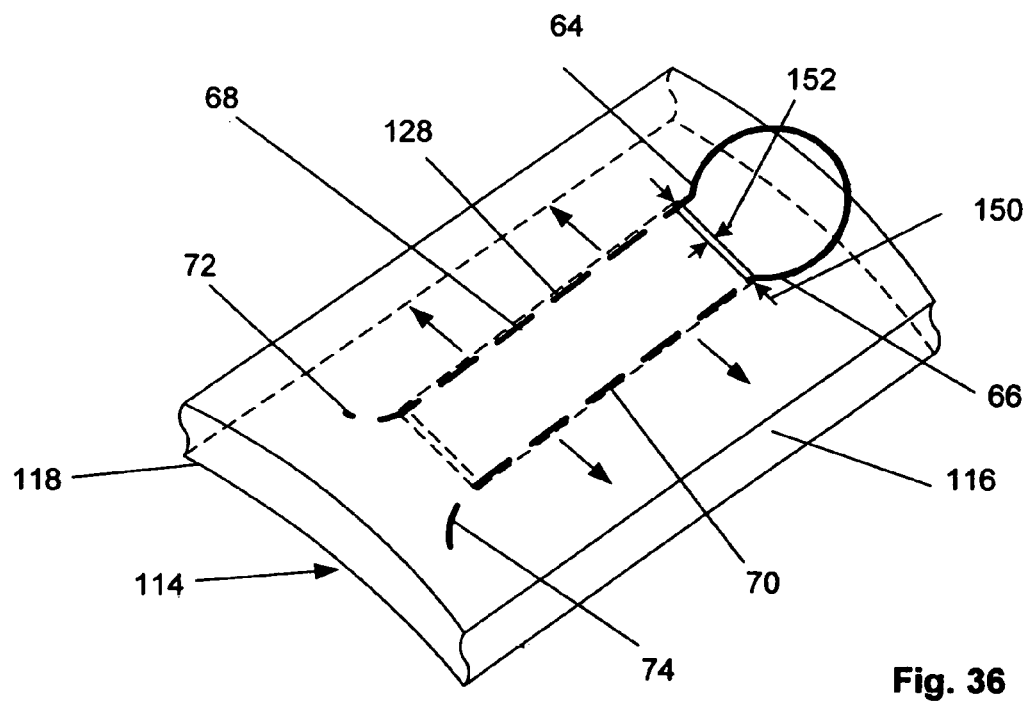

FIGS. 35 and 36 illustrate a method of deploying the tensioner 58. As shown in FIG. 35, the tensioner 58 can be in a compressed configuration. The tensioner 58 can be exposed to the compressive forces, as shown by arrows 144. The compressive forces can be applied by a retractable sheath, clamps, other methods known to one having ordinary skill in the art, or combinations thereof. A deployment force, shown by arrow 146, can deploy the tensioner 58 into the arteriotomy 120 or 128.

The arteriotomy 120 or 128 can have an arteriotomy diameter 148. The arteriotomy diameter 148 can be from about 0.5 mm (0.020 in.) to about 400 mm (15 in.), yet a narrower range from about 1.0 mm (0.040 in.) to about 10.2 mm (0.400 in.), for example about 2.54 mm (0.100 in.). When in the compressed configuration, the tensioner inter-leg outer diameter 78 can be smaller than the arteriotomy diameter 148. The tensioner first and second shoulders 64 and 66 can be wide enough to interference fit with the arteriotomy 120 or 128. The tensioner first and second shoulders 64 and 66 can dissipate force on the lumen wall surface 118.

As shown in FIG. 36, the compressive forces can be removed from the tensioner 58. The tensioner first and second leg 68 and 70 can expand, as shown by arrows. The tensioner 58 can force the arteriotomy 120 or 128 into a substantially or completely flat and/or closed and/or stretched configuration. The walls of the arteriotomy 120 or 128 can come into close contact.

The arteriotomy 120 or 128 can have an arteriotomy width 150 and an arteriotomy height 152. The arteriotomy width 150 can be about half the circumference of the arteriotomy 120 or 128. The arteriotomy width 150 can be from about 1.0 mm (0.040 in.) to about 10.2 mm (0.400 in.), for example about 4.06 mm (0.160 in.).

The arteriotomy height 152 can be about the tensioner leg diameter 76. The arteriotomy height 152 can be less than about 0.51 mm (0.020 in.), more narrowly, less than about 0.38 mm (0.015 in.); The arteriotomy height 152 can be from about 0.25 mm (0.010 in.) to about 1.3 mm (0.050 in.), for example about 0.38 mm (0.015 in.). The arteriotomy height 152 can be small enough to enable cell growth, blood clotting, acoustic sealing, heat sealing, gluing, enhanced self-sealing and combinations thereof across the arteriotomy 120 or 128.

The tensioner first and second shoulders 64 and 66 can be wide enough to interference fit with the arteriotomy 120 or 128. The tensioner first and second feet 72 and 74 can be wide enough to interference fit with the arteriotomy 120 or 128. The tensioner first and second feet 72 and 74 can dissipate force on the lumen wall surface 118.

The arteriotomy 120 or 128 can be plugged, and/or packed, and/or tamponed before, and/or concurrent with, and/or after using any of any of the supplemental closure devices infra and/or supra, the self-sealing closure method, or combinations thereof. The plug, pack, tampon, or combinations thereof (not shown) can be made from gelfoam, collagen, other implantable and biocompatible tampon materials known to those having ordinary skill in the art, or combinations thereof.

Figure 37:
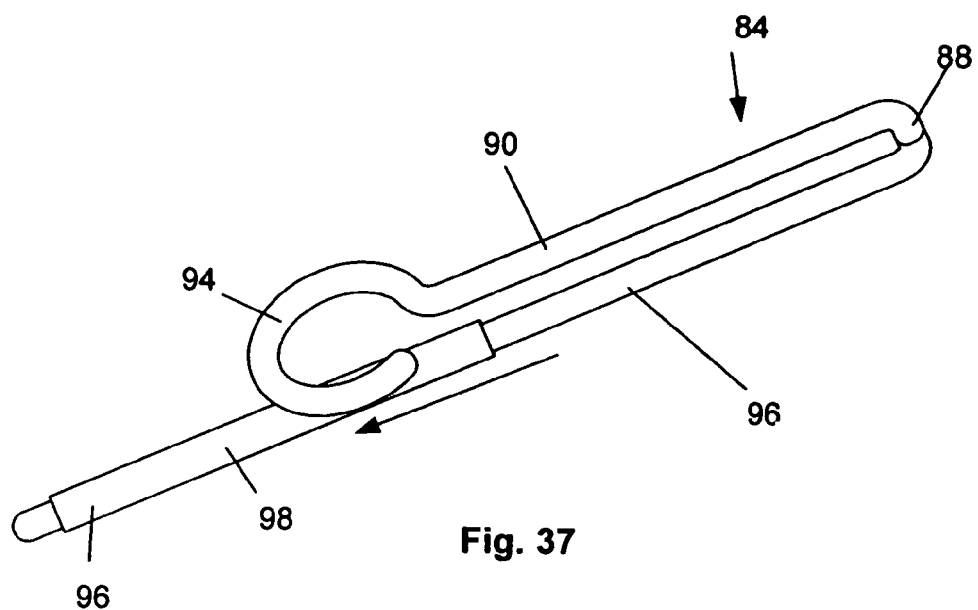
FIGS. 37-40 illustrate methods for deploying various embodiments of the pressure clip in a cross-section of a lumen.

FIGS. 37 through 40 illustrate deploying the pressure clip 84 to the arteriotomy 120 or 128. FIG. 37 illustrates extending, and/or thinning, and/or straightening, and/or tensioning the pressure clip second end 96. The pressure clip sheath 98 can be translated, as shown by arrow, along the pressure clip second leg 92 and onto the pressure clip second end 96. The pressure clip 84 can be deployed to the arteriotomy after the pressure clip second end 96 is extended, and/or thinned, and/or straightened, and/or tensioned.

Figure 38:
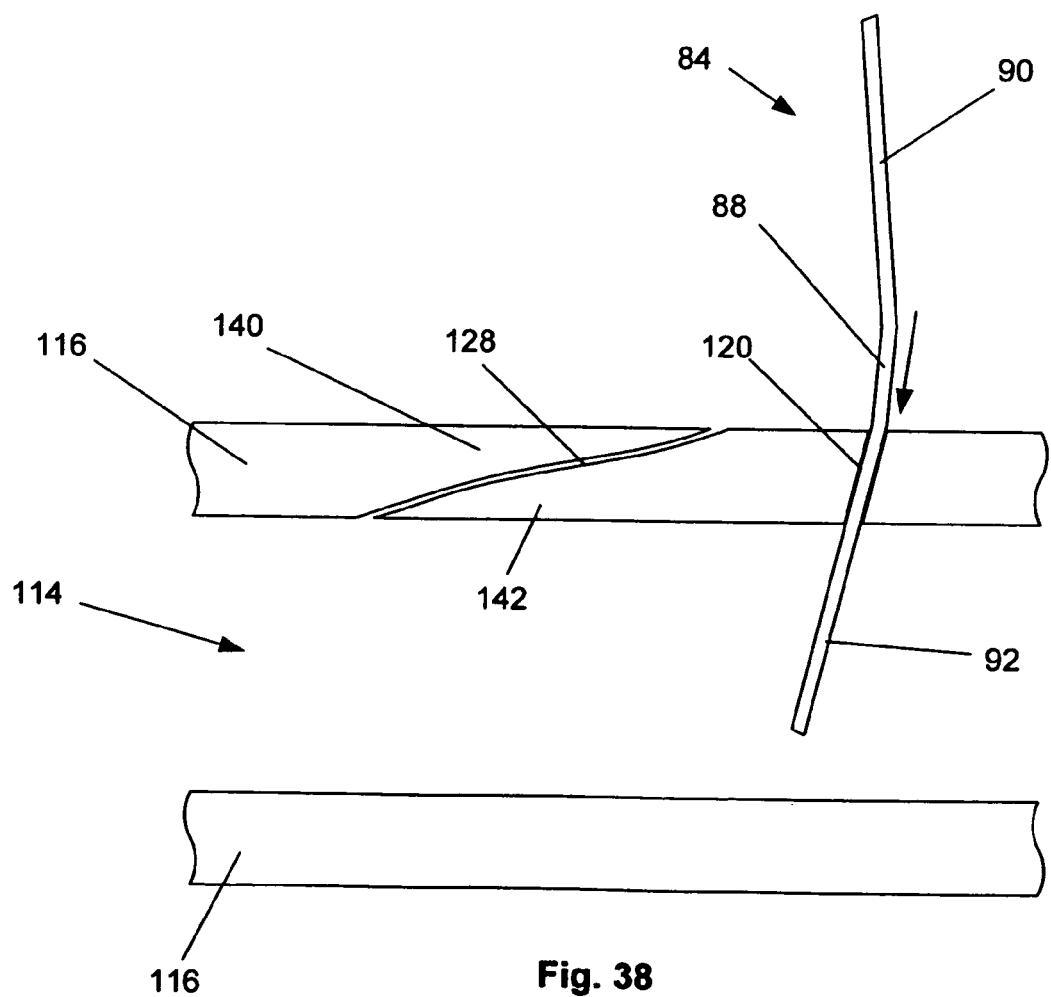

As shown in FIG. 38, the pressure clip second leg 92 can be rotated with respect to the pressure clip head 88, so that the pressure clip second leg 92 and the pressure clip head 88 are substantially aligned. The pressure clip second leg 92 can be deployed, as shown by the arrow, through the first arteriotomy 120. The pressure clip second leg 92 can be deployed through the lumen wall 116 (e.g., if there is no existing first arteriotomy 120, if the first arteriotomy 120 is not suitably located with respect to the second arteriotomy 128).

Figure 39:
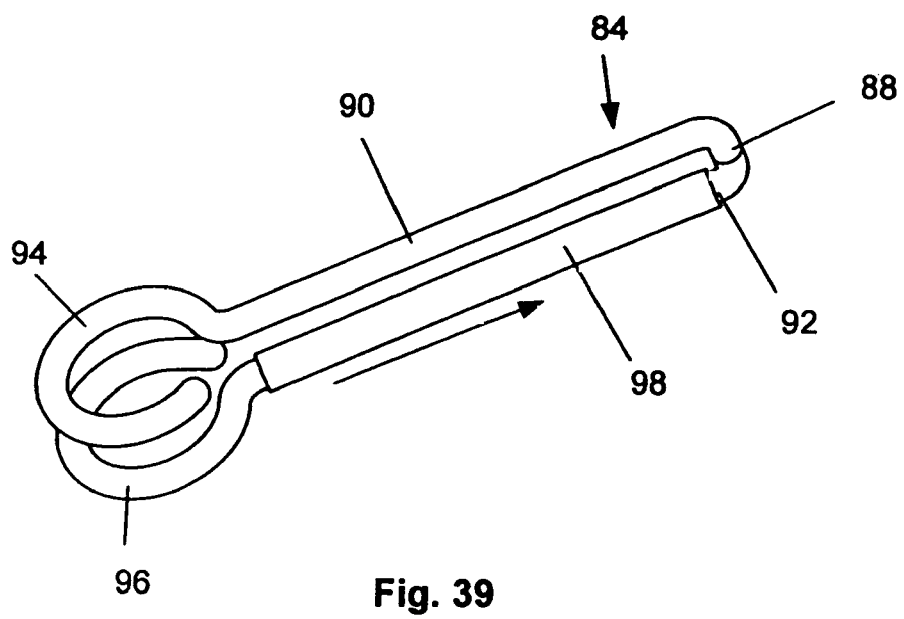

FIG. 39 illustrates contracting, and/or widening, and/or releasing and/or relaxing the pressure clip second end 96. The pressure clip sheath 98 can be translated, as shown by arrow, along the pressure clip second leg 92 and off of the pressure clip second end 96. The pressure clip second end 96 can be contracted, and/or widened, and/or released and/or relaxed after the pressure clip 84 is deployed to the arteriotomy.

Figure 40:
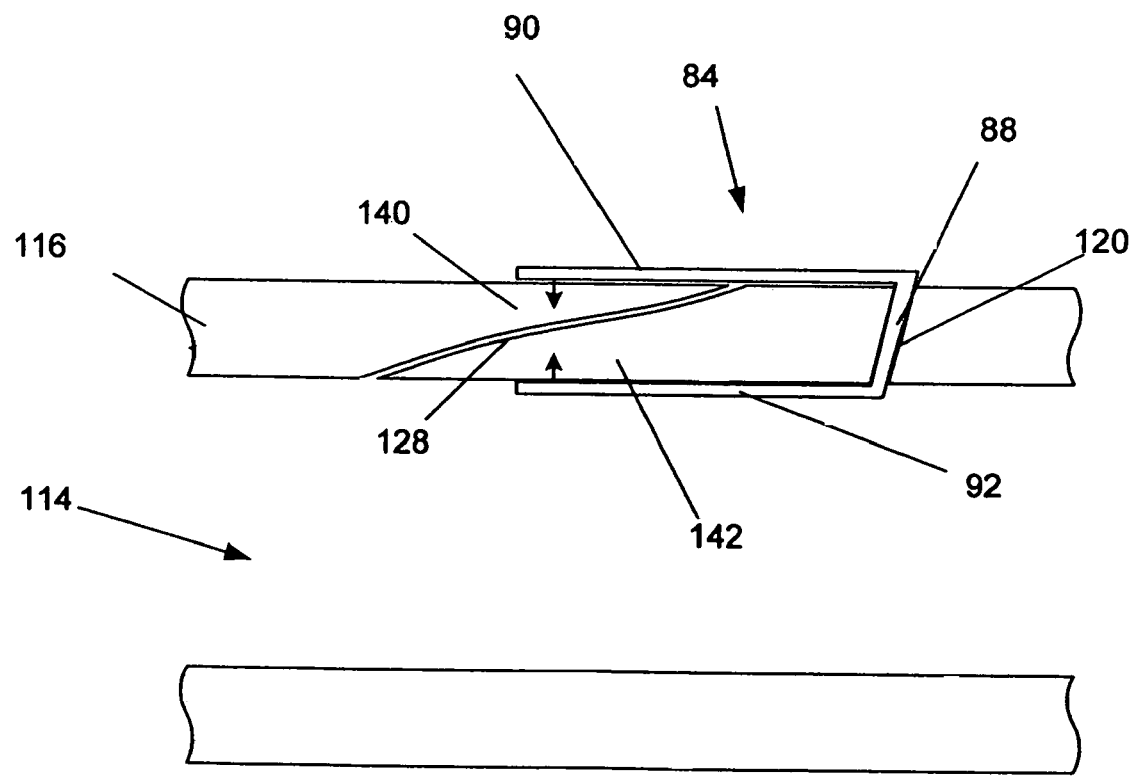

As shown in FIG. 40, after the pressure clip second leg 92 is deployed through the first arteriotomy 120, the pressure clip second leg 92 can be released or deformed so as to rotate with respect to the pressure clip head 88. The pressure clip head 88 can seat in the first arteriotomy 120. The pressure clip first and second legs 90 and 92 can apply force, as shown by arrows, to the first and second webs 140 and 142, respectively.

Figure 41:
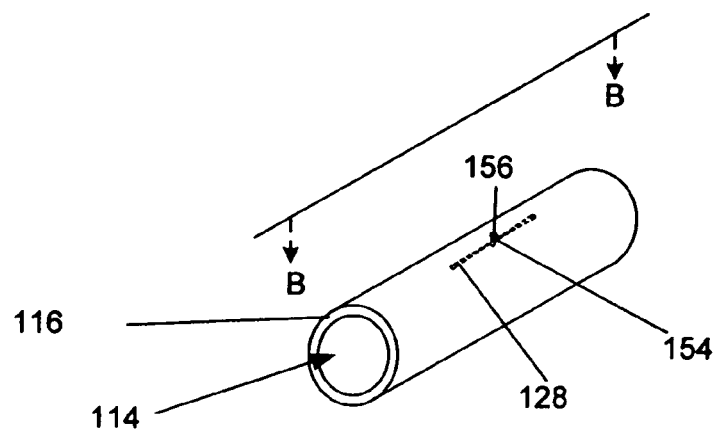
FIG. 41 illustrates a method of using a suture on a portion of an arteriotomized lumen.
Figure 42:
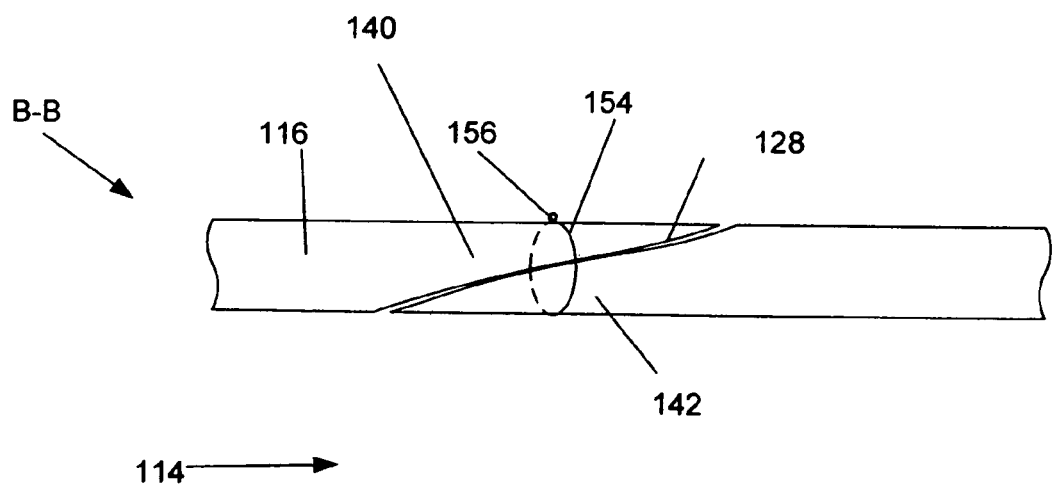
FIG. 42 illustrates section B-B of FIG. 41 with the out-of-section suture.

FIGS. 41 and 42 illustrate a method of deploying a stitch 154 surrounding and/or through the arteriotomy 120 or 128. The stitch 154 can be tightened to apply additional pressure to the arteriotomy 120 or 128. The stitch 154 can have a knot 156, or other tying configuration or device, for example a pledget or clamp.

Figure 43:
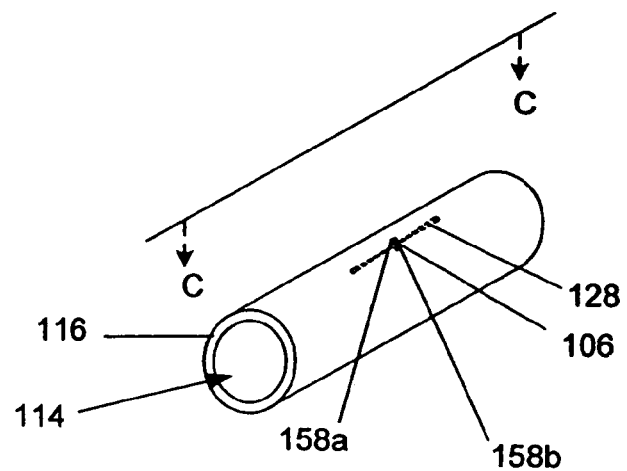
FIG. 43 illustrates a method of using pledgets on a portion of an arteriotomized lumen.
Figure 44:
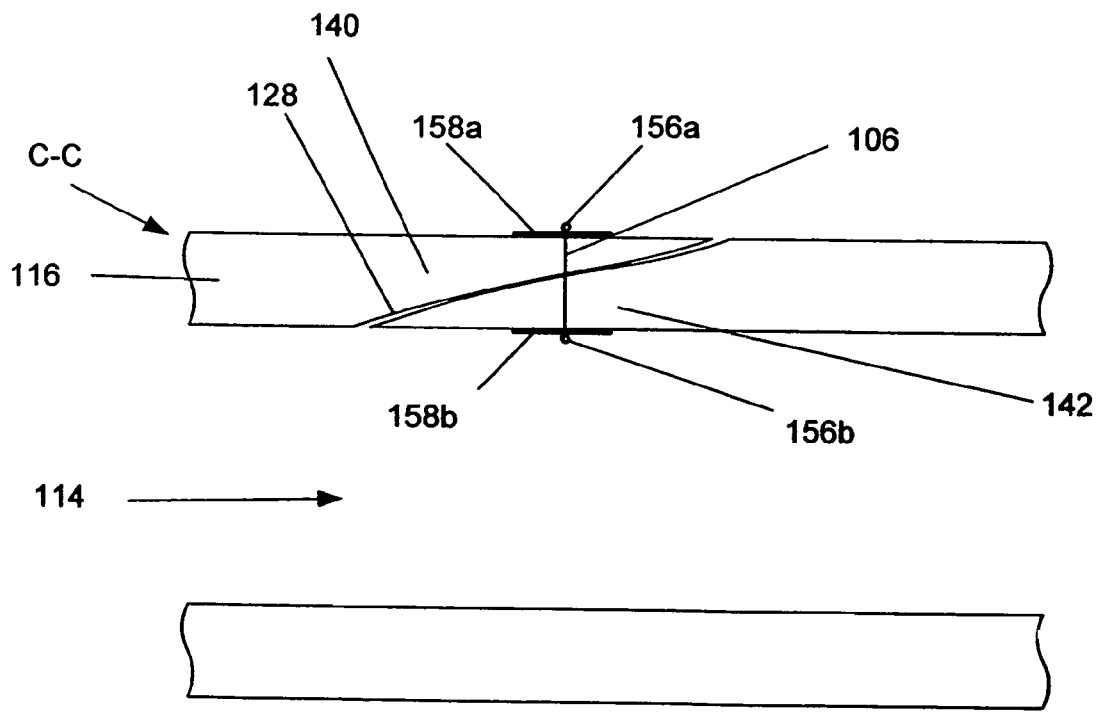
FIG. 44 illustrates section C-C of FIG. 43.

FIGS. 43 and 44 illustrate a method of deploying the filament 106 adjacent to and/or through the arteriotomy 120 or 128. The filament 106 can be attached to a first pledget 158a by a first knot 156a or other tying configuration or device. The filament 106 can be attached to a second pledget 158b by a second knot 156b or other tying configuration or device. The first and second pledgets 158a and 158b can be other pressure diffusers known to one having ordinary skill in the art, such as the toggles 100 described infra and supra.

Figure 45:
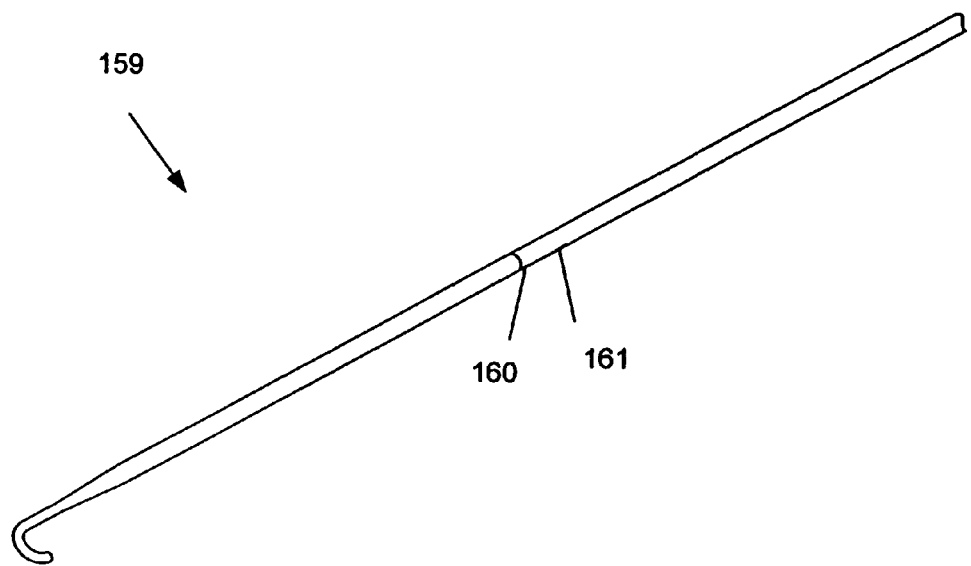
FIG. 45 illustrates an embodiment of the toggle deployment device in a first configuration.
Figure 46:
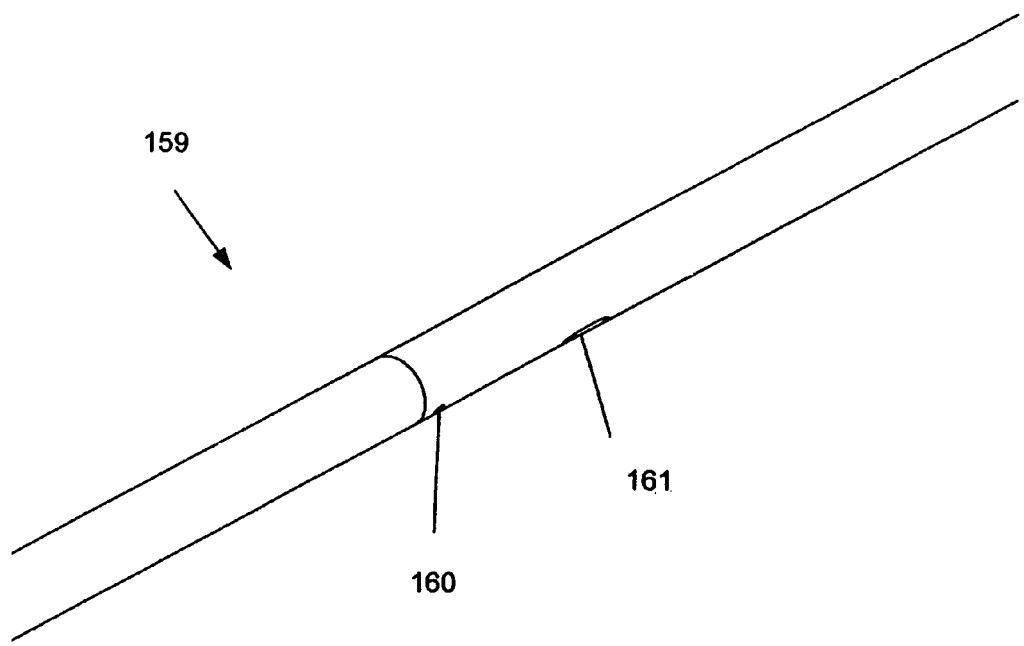
FIG. 46 is a close-up view of FIG. 45.

FIGS. 45 and 46 illustrate a toggle deployment device 159 that can be in a first retracted configuration. The toggle deployment device 159 can have a pressure check port 160. The pressure check port 160 can be in fluid communication with a sensor or port on or near the handle (not shown) of the toggle deployment device 159, such as an external lumen where blood flow can be observed, for example from flow from the end of an external tube or port and/or through a transparent or translucent window. The pressure check port 160 can facilitate deployment of the toggle deployment device 159 to a location where the pressure check port 160 is introduced to pressure, for example when the pressure check port 160 enters the biological lumen 114. The sensor or port on or near the handle of the toggle deployment device 159 will signal that the pressure check port 160 has been placed into the biological lumen 114 (e.g., by displaying a small amount of blood flow). The pressure check port 160 can be deployed into the biological lumen 114 and then withdrawn from the biological lumen 114 to the point where the lumen wall 116 just stops the pressure in the pressure check port 160. The entry wall retainer port 54 can additionally perform the function as described herein for the pressure check port 160. The toggle deployment device 159 can have a delivery needle port 161.

Figure 47:
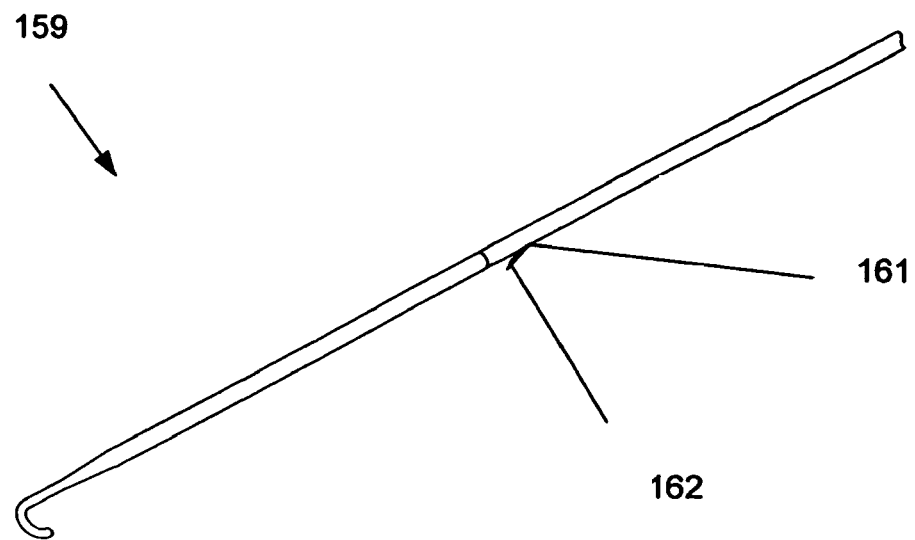
FIG. 47 illustrates an embodiment of the toggle deployment device in a second configuration.
Figure 48:
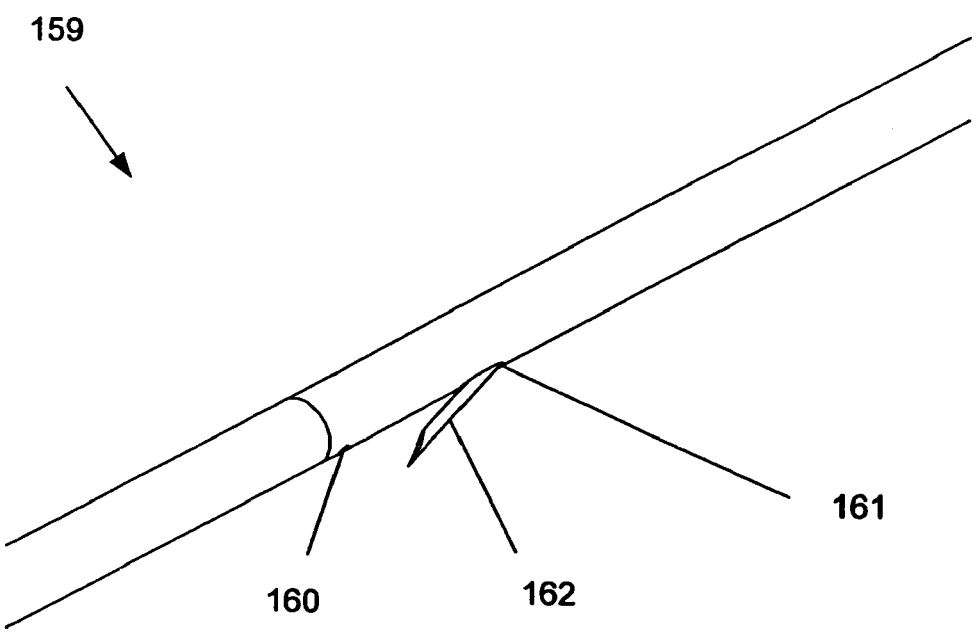
FIG. 48 is a close-up view of FIG. 47.

FIGS. 47 and 48 illustrate the toggle deployment device 159 that can be in a second delivery configuration. A delivery needle 162 can be slidably attached to the toggle deployment device 159. The delivery needle 162 can egress from the delivery needle port 161 when the toggle deployment device 159 is in the second delivery configuration.

Figure 49:
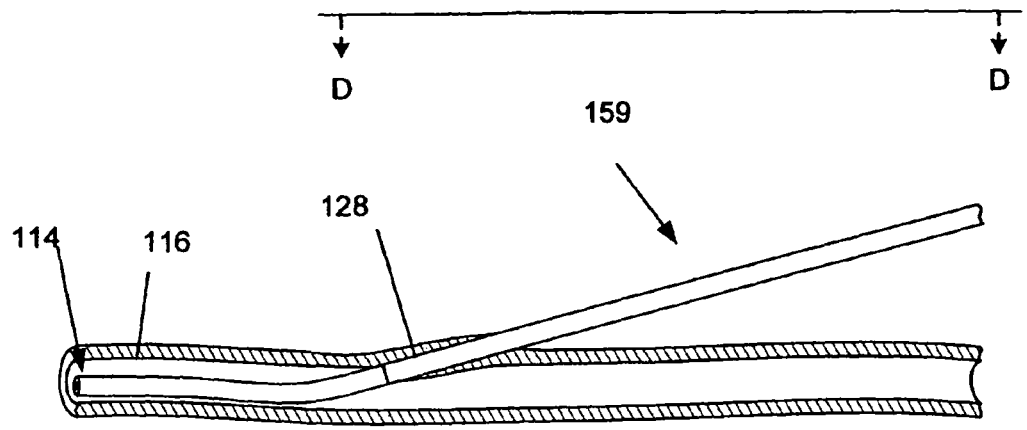
FIG. 49 illustrates a method of using the toggle deployment device in a cross-section of a lumen.
Figure 50:
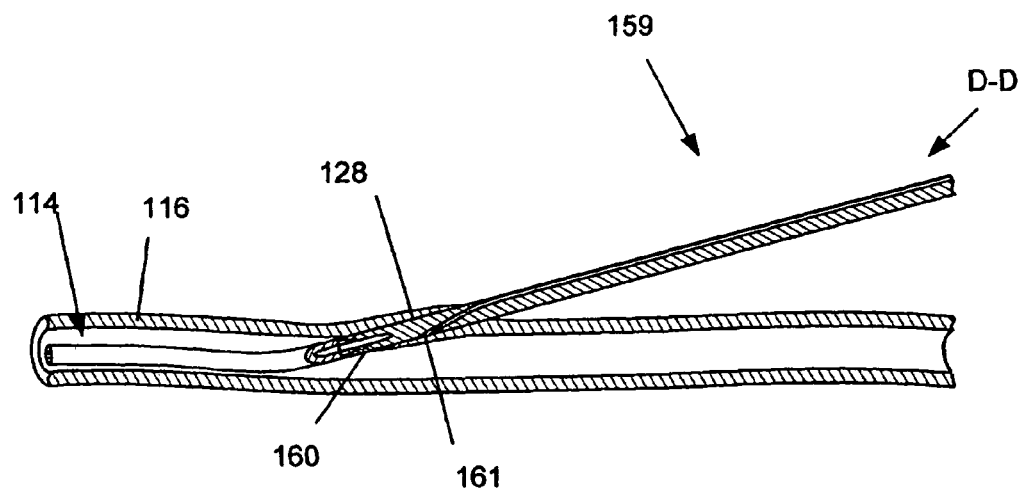
FIG. 50 illustrates FIG. 49 with a portion of the toggle deployment device shown in section D-D.

FIGS. 49 and 50 illustrate that the toggle deployment device 159 can be deployed into the arteriotomy 120 or 128 at a location where the pressure check port 160 can be located in the biological lumen 114. The delivery needle port 161 can be in, or adjacent to, the lumen wall 116.

Figure 51:
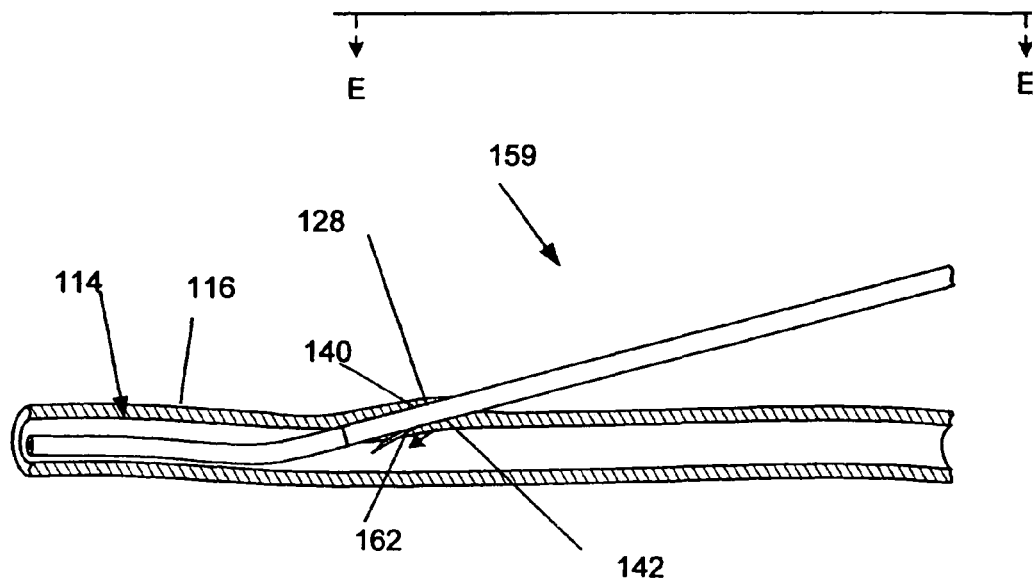
FIG. 51 illustrates a method of using the toggle deployment device in a cross-section of a lumen.
Figure 52:
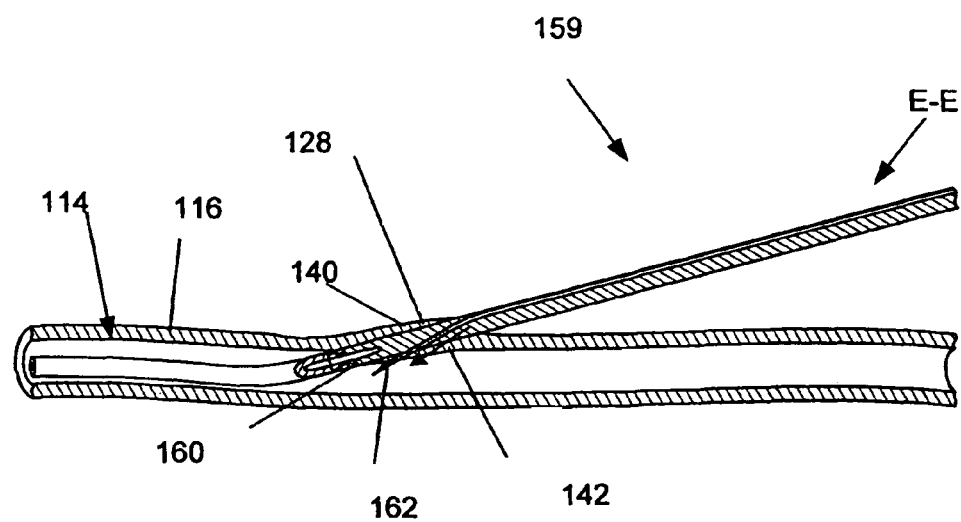
FIG. 52 illustrates FIG. 51 with a portion of the toggle deployment device shown in section E-E.

FIGS. 51 and 52 illustrate that the toggle deployment device 159 can be placed in the second delivery configuration. If the delivery needle port is in, or adjacent to, the lumen wall 116 when the toggle deployment device 159 is placed in the second delivery configuration, the delivery needle 162 can enter the lumen wall 116. For example, the delivery needle 162 can enter the second web 142. The delivery needle 162 can exit the second web 142 and enter, as shown by arrows, the biological lumen 114.

Figure 53:
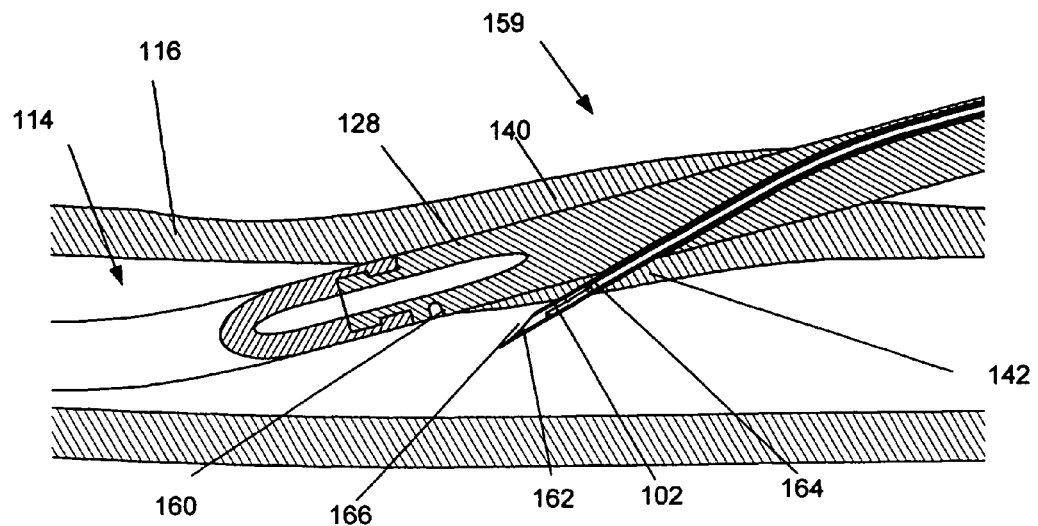
FIGS. 53-55 illustrate a method of using the toggle deployment device in a cross-section of a lumen.

FIG. 53 illustrates that a pusher 164 can be slidably attached to the delivery needle 162. The delivery needle 162 can have a needle tip port 166. The toggle 100 can be in the delivery needle 162. The toggle 100 can be configured in the delivery needle 162 such that the toggle first end 102 can be located on the needle tip port 166—side of the pusher 164.

Figure 54:
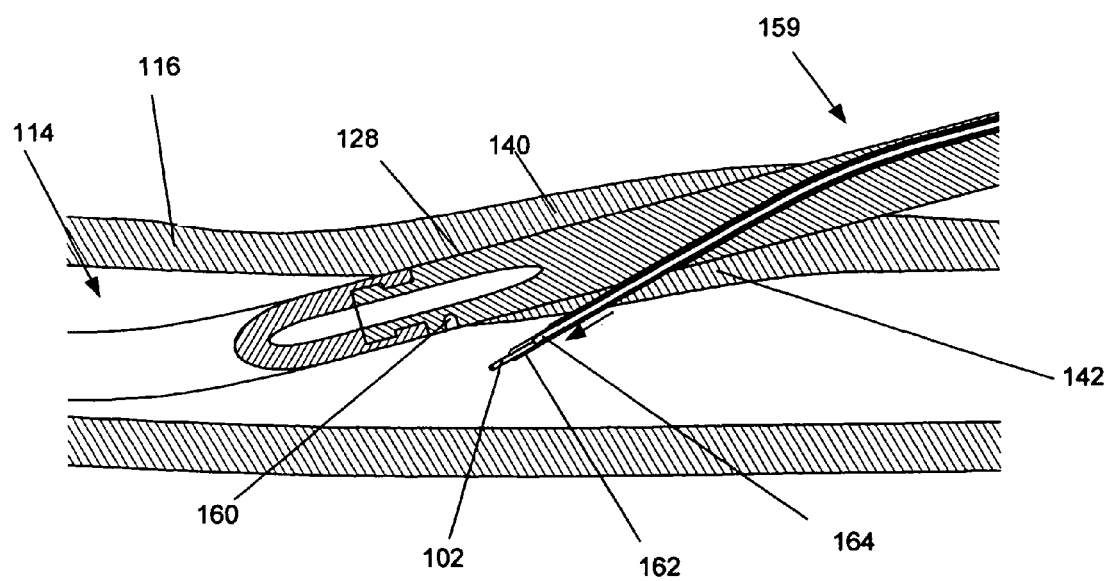

FIG. 54 illustrates that the pusher 164 can be moved, as shown by arrow, toward the needle tip port 166. The delivery needle 162 can be moved back relative to the pusher 164, the pusher 164 can be moved forward relative to the delivery needle 162, or combinations thereof. The pusher 164 can push the toggle first end 102 out of the delivery needle 162. The pusher 164 can push the toggle first end 102 into the biological lumen 114.

Figure 55:
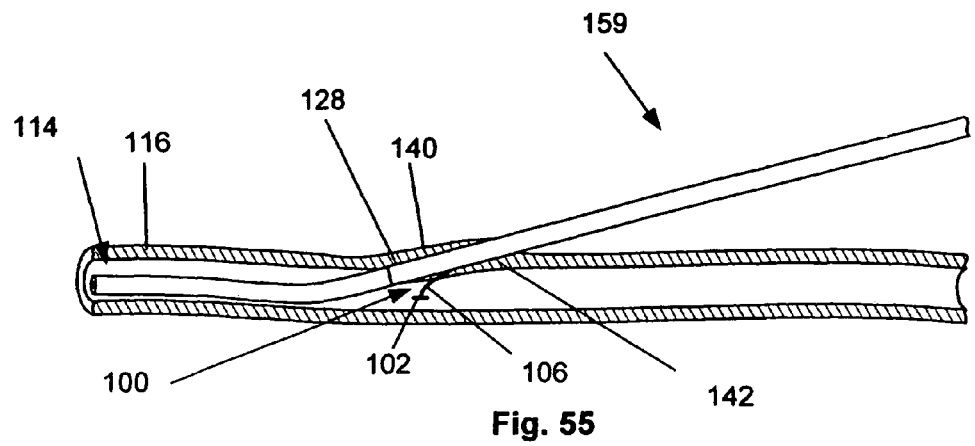
Figure 56:
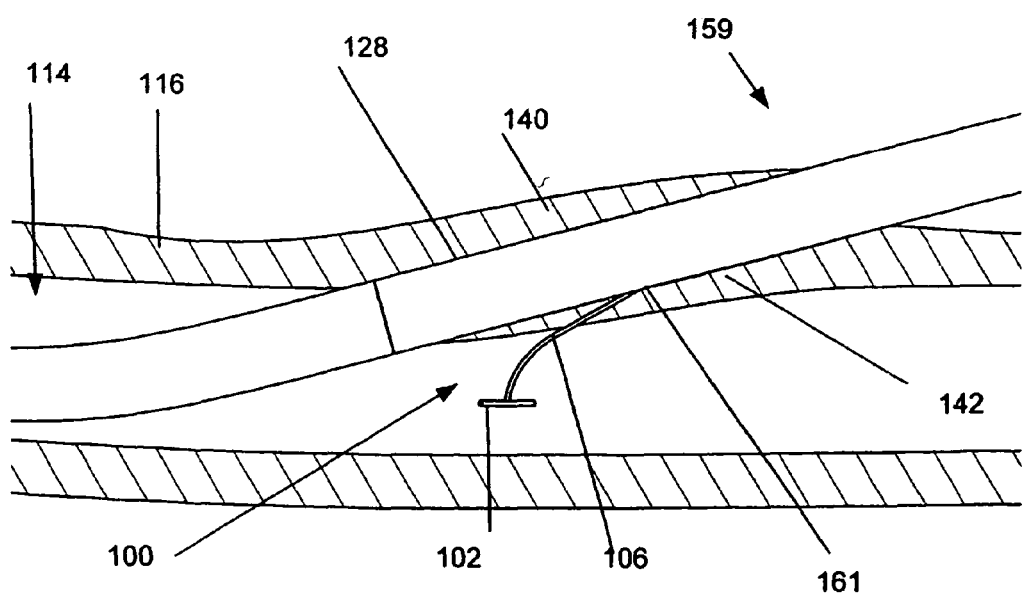
FIG. 56 is a close-up view of FIG. 55.

FIGS. 55 and 56 illustrate that the toggle deployment device 159 can be in a first retracted configuration after deploying the toggle first end 102 into the biological lumen 114. When the delivery needle 162 retracts into the toggle deployment device 159, the toggle second end 104 can be in the toggle deployment device 159. The filament 106 can extend though the delivery needle port 161.

Figure 57:
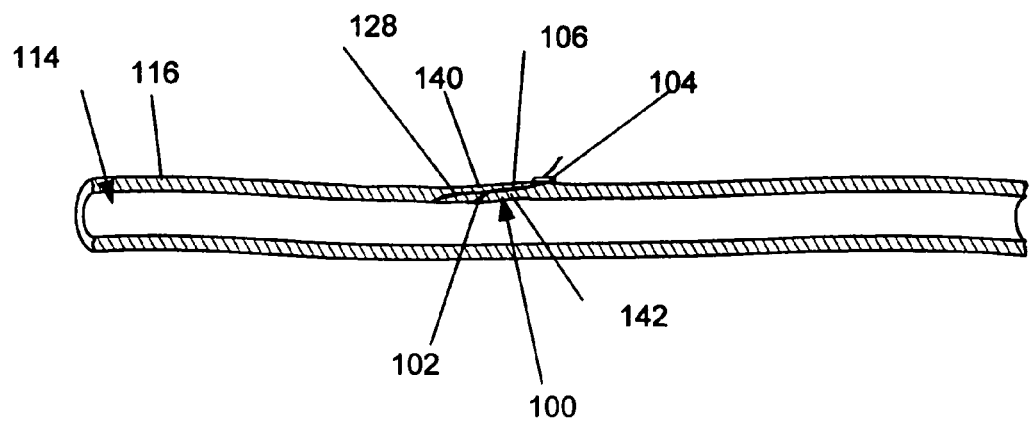
FIG. 57 illustrates an embodiment of a deployed toggle in a cross-section of a lumen.
Figure 58:
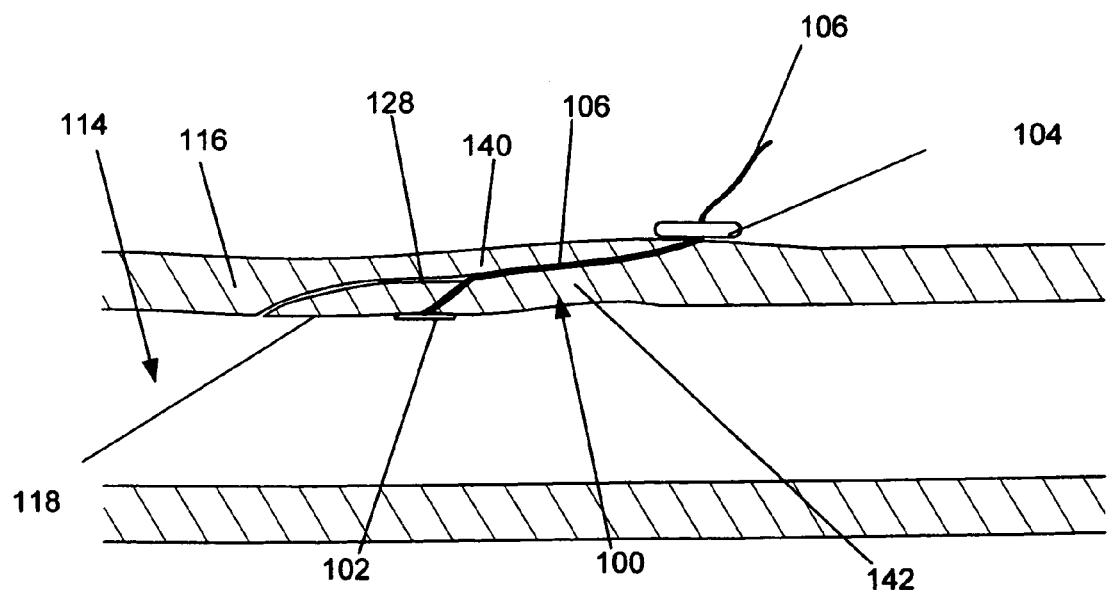
FIG. 58 is a close-up view of FIG. 59.
Figure 59:
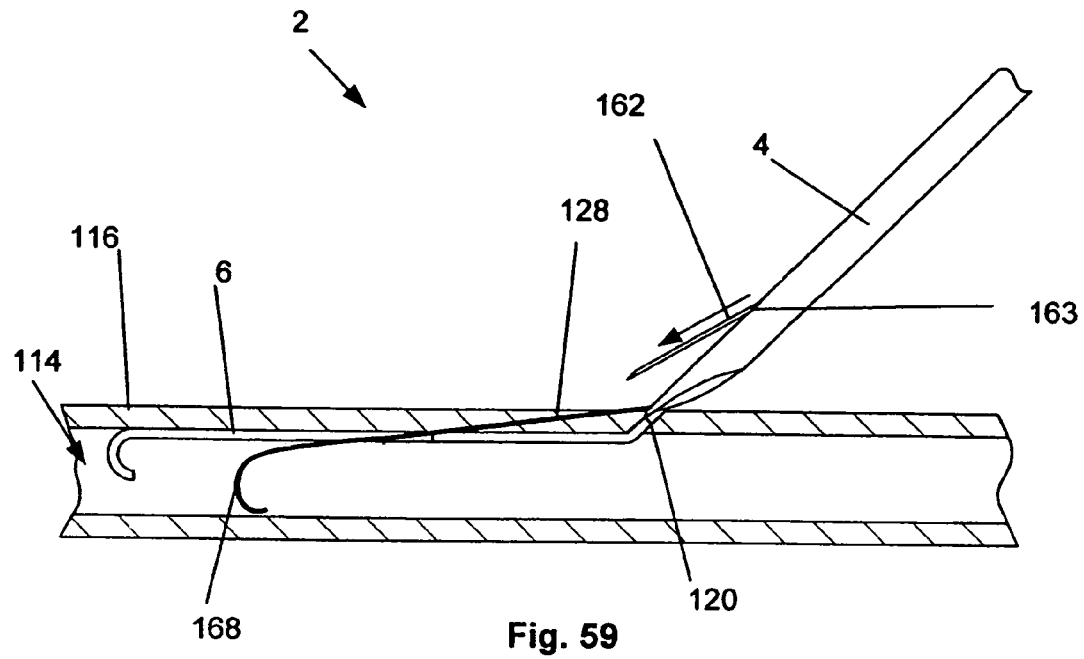
FIGS. 59-61 illustrate a method for deploying a toggle in a cross-section of a lumen.

FIGS. 57 and 58 illustrate that the toggle 100 can be deployed across the lumen wall. When the toggle deployment device 159 is removed from the arteriotomy, the toggle second end 104 can deploy on the outside of the lumen wall 116 from the delivery needle port 161. The toggle first end 102 can form an interference fit with the lumen wall surface 118. The toggle second end 104 can form an interference fit with the outside of the lumen wall 116 or the surrounding tissue, such as subcutaneous tissue. The toggle second end 104 can be slidably translated along the filament 106 toward the lumen wall 116, for example for the toggle 100 illustrated in FIG. 20. The length of the filament 106 on the opposite side of toggle second end 104 from the toggle first end 102 can be cut, snapped, torn or otherwise removed.

FIGS. 59 through 63 illustrate a method for deploying the toggle 100. The delivery needle 162 can egress, as shown by arrow, from a toggle deployment delivery port 163. The toggle deployment delivery port 163 can be in the delivery guide 4. The delivery needle 162' can be advanced toward the lumen 114.

Figure 60:
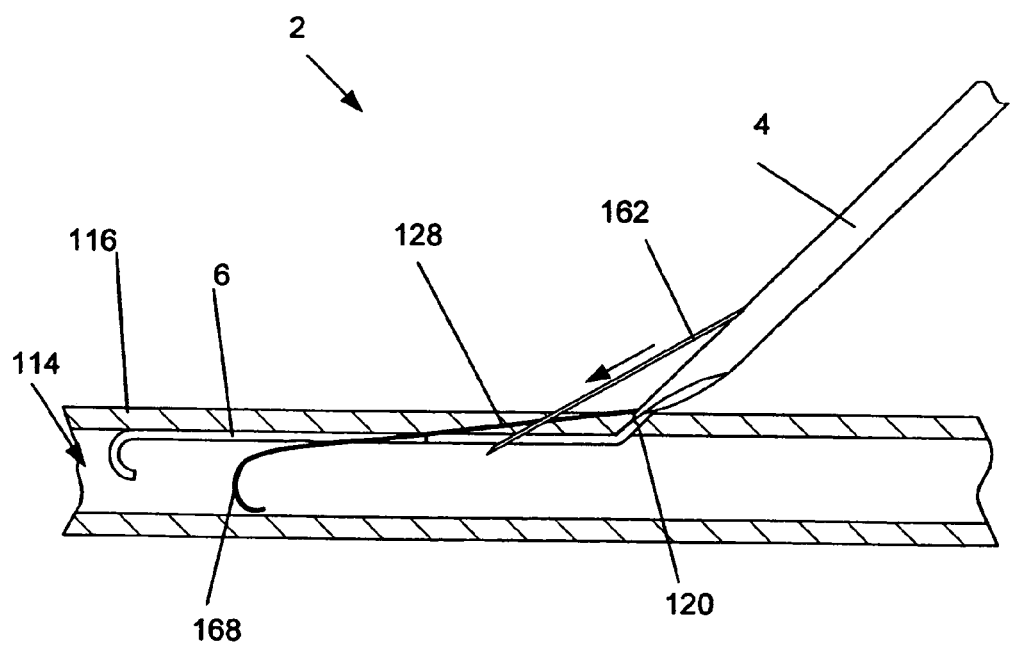

FIG. 60 illustrates that the delivery needle 162 can be deployed through the lumen wall. When the delivery needle 162 is deployed through the lumen wall 116, the delivery needle can intersect, or pass adjacent to, the second arteriotomy.

Figure 61:
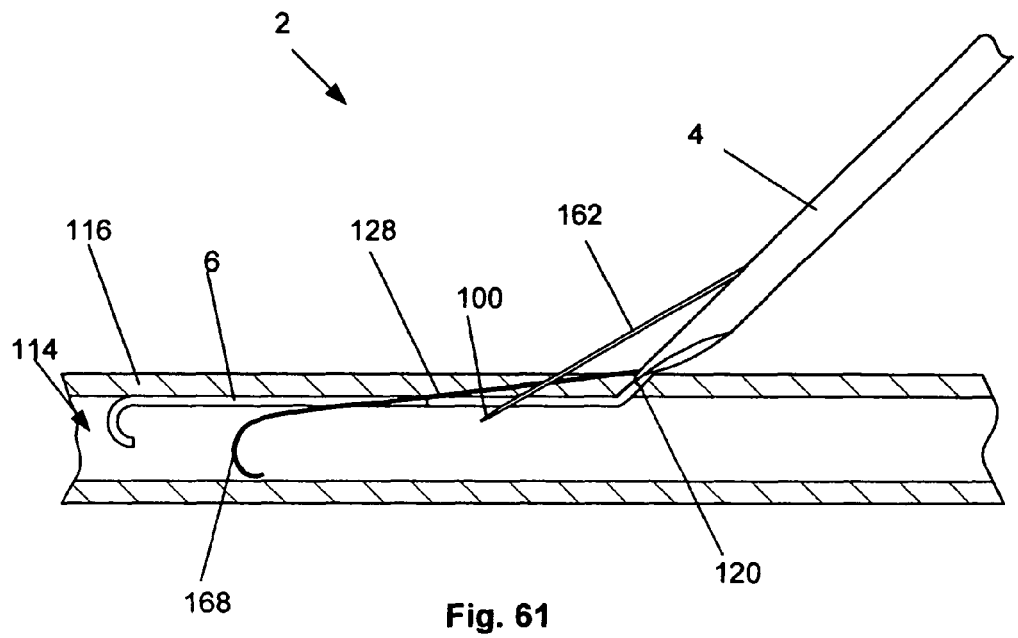
Figure 62:
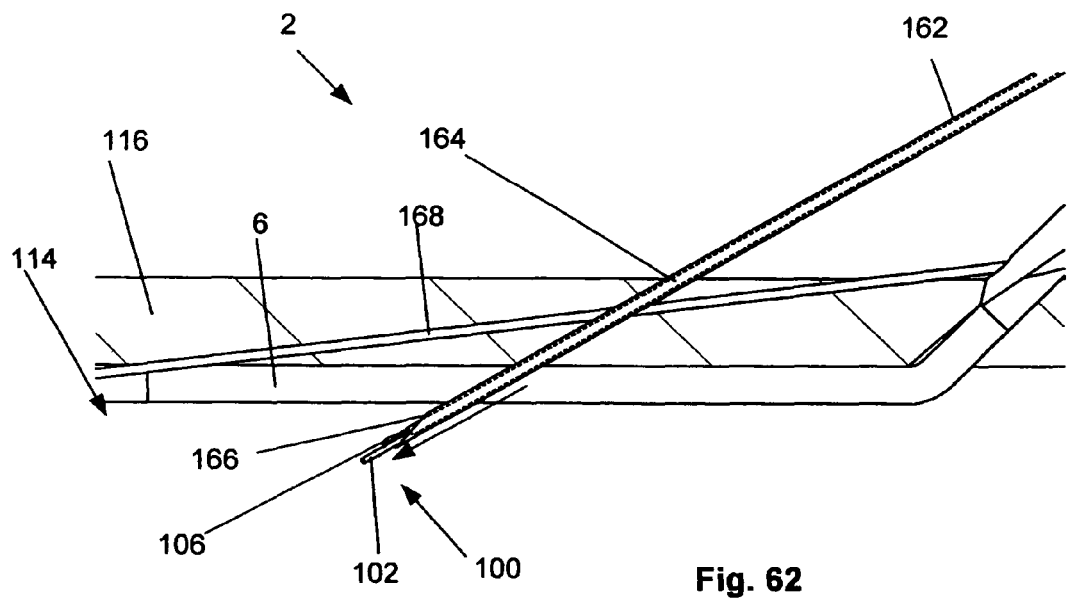
FIG. 62 is a close-up view of FIG. 61.

FIGS. 61 and 62 illustrate that the pusher 164 can be advanced, as shown by arrow, through the delivery needle 162. The toggle first end 102 can egress from the needle tip port 166. The toggle first end 102 can deploy into the lumen 114.

Figure 63:
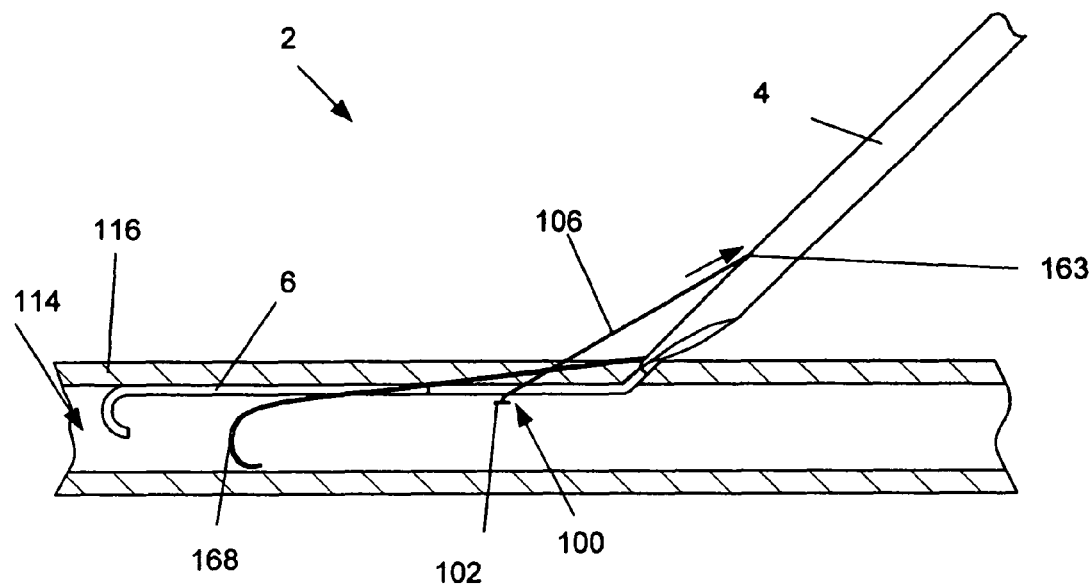
FIG. 63 illustrates a method for deploying a toggle in a cross-section of a lumen.

FIG. 63 illustrates that the delivery needle 162 can be retracted into the delivery guide 4 and/or the filament 106 can be pulled taught, both shown by arrow. The toggle first end 102 can form an interference fit with the lumen wall surface 118. The toggle second end 104 (not shown in FIG. 63) can be slidably translated on the filament 106 down to, and form an interference fit with, the outside of the lumen wall 116. The length of the filament 106 on the opposite side of toggle second end 104 from the toggle first end 102 can be cut, snapped, torn or otherwise removed.

Figure 64:
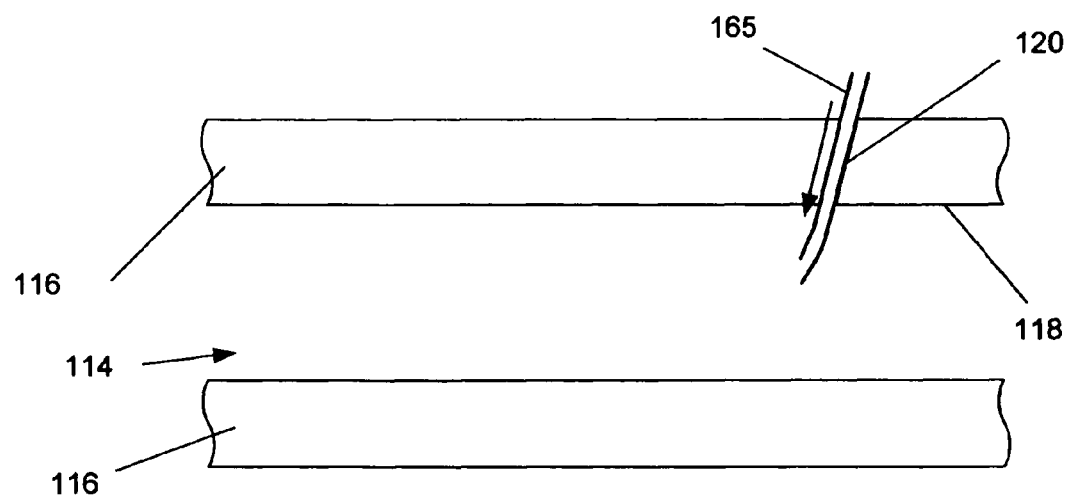
FIGS. 64-66 shown, in cross-section, a method for deploying the guidewire through an arteriotomy.
Figure 65:
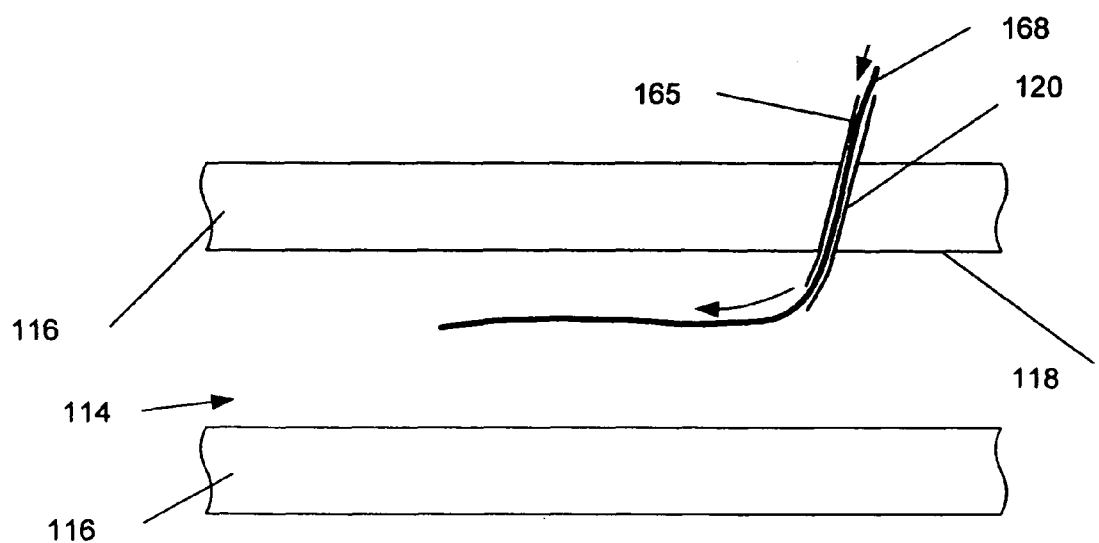

FIG. 64 illustrates an introducer needle 165 that can have an end inserted, as shown by arrow, through the lumen wall 116 and into the lumen 114, for example by using the Seldinger technique. The introducer needle 165 can be hollow and/or have a longitudinal channel. FIG. 65 illustrates that the guidewire 168 can be deployed, shown by arrows, through the hollow and/or longitudinal channel of the introducer needle 165.

Figure 66:
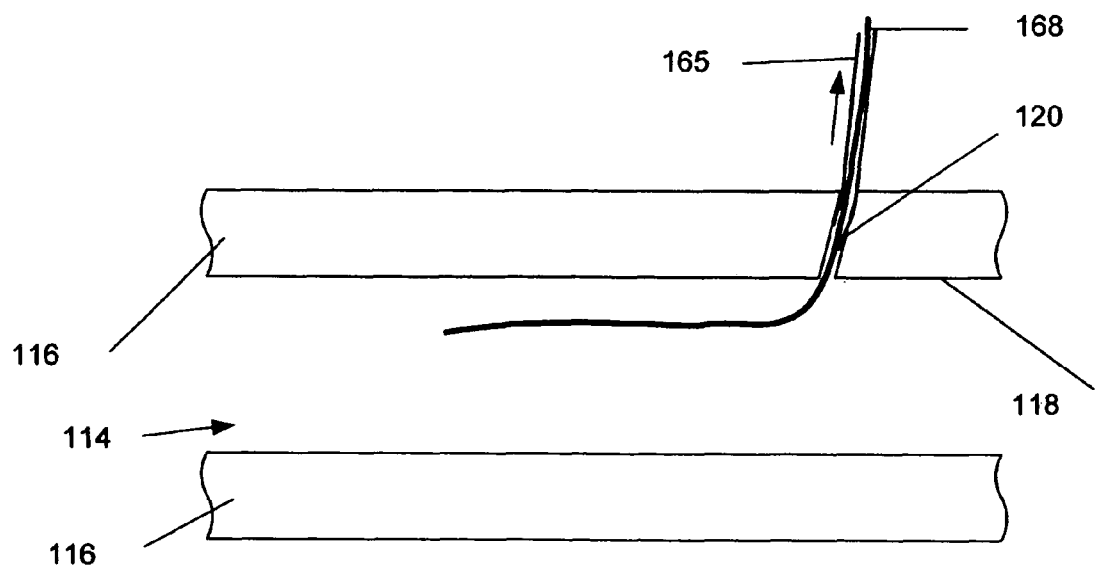

FIG. 66 illustrates that the introducer needle 165 can be removed, as shown by arrow, from the lumen wall 116. The guidewire 168 can remain substantially in place. After the introducer needle 165 is removed, a portion of the guidewire 168 can be outside the lumen 114 and another portion of the guidewire 168 can be inside the lumen 114.

Figure 67:
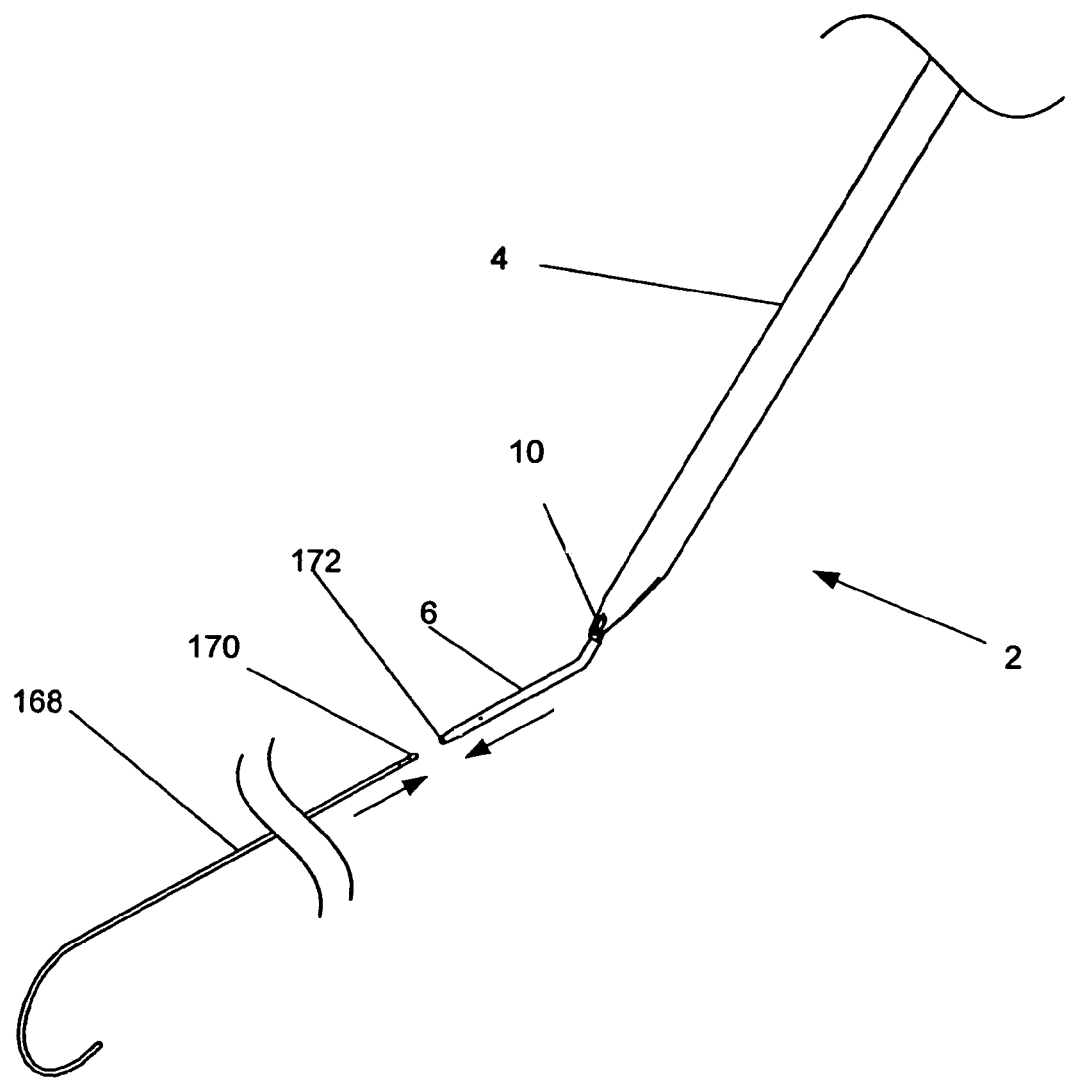
FIGS. 67 and 68 illustrate a method for attaching guidewire to the anchor.
Figure 68:
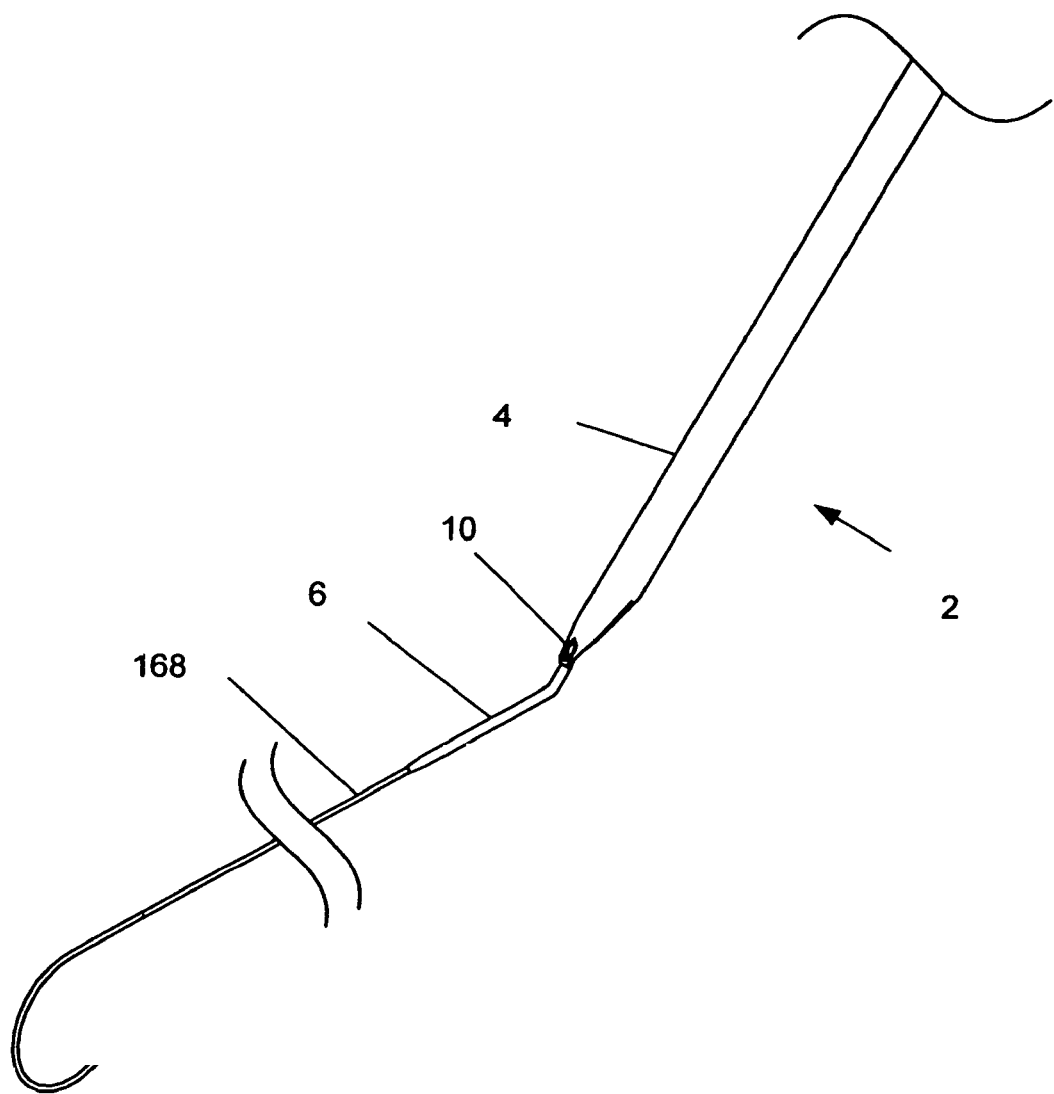

FIG. 67 illustrates a method of fixedly or slidably attaching the guidewire 168 to the anchor 6. A guidewire proximal end 170 can be placed in proximity to an anchor distal end 172. The guidewire proximal end 170 can then be attached, as shown by arrows, to the anchor distal end 172. The guidewire proximal end 170 can be attached to the anchor distal end 172 while some or all of the guidewire 168 is in the lumen 114. The guidewire proximal end 170 can be configured to snap-fit, interference fit, slidably attach or combinations thereof, to the anchor 6. When the guidewire 168 is attached to the anchor 6, the guidewire 168 can act as the anchor extension section 14 and/or the lumenal tool. FIG. 68 illustrates the guidewire 168 attached to the anchor 6.

Where applicable, the methods described supra for deploying any supplemental closure device can be used for deploying any of the other supplementary deployment device. It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

I claim:

1. A method for creating a self-sealing tract in a blood vessel using a device comprising a first introducer and a second introducer, the method comprising:
   a. advancing the first introducer into the vessel wall through a first arteriotomy that has a first angle with respect to the vessel wall;
   b. applying a force to the first introducer to position a portion of the vessel wall adjacent the first introducer in a desired configuration relative to the first introducer;
   c. while maintaining the vessel wall portion in the desired configuration with the first introducer, advancing the second introducer through a proximal extension of the first introducer and through a blood vessel wall to create a substantially diagonal tract through the vessel wall wherein a distal portion of the tract defines a second angle with respect to the vessel wall, wherein the first angle is larger than the second angle, and wherein the tract is defined between overlapping tissue portions of the vessel wall; and
   d. expanding the tract with a sheath so that a procedure may be performed therethrough, wherein after the procedure has been performed and the device and sheath have been withdrawn from the tract, blood pressure acting on the vessel causes the overlapping tissue portions to collapse and self-seal.

2. The method of claim 1 wherein the method comprises:
   advancing the first introducer through the vessel wall into a lumen of the vessel, wherein at least a portion of the first introducer is used to locate an inner surface of a lumen wall; and
   advancing the second introducer through the vessel wall above the inner surface of the lumen wall, to create the tract.

3. The method of claim 2 further comprising delivering a drug within the lumen of vessel.

4. The method of claim 1 further comprising delivering a drug within the vessel wall.

5. The method of claim 1 wherein the vessel wall comprises intima, media, adventitia, or a combination thereof.

6. The method of claim 2 wherein at least one of the first or second introducers comprises a lumen and wherein the method further comprises introducing a guidewire through the lumen of the first or second introducer.

7. The method of claim 1 wherein the tract comprises at least two distinct segments.

8. The method of claim 1 wherein the tract has a diameter of about 1.0 mm to about 10.2 mm.

9. The method of claim 1 further comprising advancing the second introducer into a lumen of the vessel.

10. The method of claim 9 wherein the first angle and the second angle form an introduction angle relative to each other.

11. The method of claim 10 wherein when the second introducer enters the lumen, the introduction angle is less than or equal to about 19°.

12. The method of claim 10 wherein when the second introducer enters the lumen, the introduction angle is less than or equal to about 15°.

13. The method of claim 10 wherein when the second introducer enters the lumen, the introduction angle is from about 5° to about 10°.

* * * * *